(12) United States Patent
Gray

(10) Patent No.: US 11,980,605 B1
(45) Date of Patent: May 14, 2024

(54) 5-METHOXY-N,N-DIMETHYLTRYPTAMINE (5-MeO-DMT) FORMULATIONS

(71) Applicant: Beckley Psytech Limited, Oxford (GB)

(72) Inventor: Jason Gray, Oxford (GB)

(73) Assignee: Beckley Psytech Limited, Oxford (GB)

( * ) Notice: Subject to any disclaimer, the term of this patent is extended or adjusted under 35 U.S.C. 154(b) by 0 days.

(21) Appl. No.: 18/229,041

(22) Filed: Aug. 1, 2023

(30) Foreign Application Priority Data

Jun. 13, 2023 (GB) ..................................... 2308830

(51) Int. Cl.
*A61K 31/4045* (2006.01)
*A61K 9/16* (2006.01)

(52) U.S. Cl.
CPC ........ *A61K 31/4045* (2013.01); *A61K 9/1652* (2013.01); *A61K 9/1694* (2013.01)

(58) Field of Classification Search
CPC .................................................. A61K 31/4045
See application file for complete search history.

(56) References Cited

U.S. PATENT DOCUMENTS

| 11,773,063 B1 | 10/2023 | Gray et al. |
| 2022/0062238 A1 | 3/2022 | Layzell et al. |

FOREIGN PATENT DOCUMENTS

| WO | 2022/246572 A1 * | 12/2022 |
| WO | WO-2022/246572 A1 | 12/2022 |
| WO | WO-2023/186834 A1 | 10/2023 |

OTHER PUBLICATIONS

Berge et al., "Pharmaceutical salts," J Pharm Sci. 66(1):1-19 (1977).
Registry No. 2761182-82-3, File Registry on STN, entered STN: Mar. 3, 2022 (2 pages).

* cited by examiner

*Primary Examiner* — Carlos A Azpuru
(74) *Attorney, Agent, or Firm* — Clark & Elbing LLP

(57) ABSTRACT

The present invention provides a dry powder formulation of 5-MeO-DMT or a pharmaceutically acceptable salt thereof, and one or more pharmaceutically acceptable carriers or excipients. The formulations described herein may be used to treat a disease or condition, such as depression or alcohol use disorder in a subject in need thereof.

16 Claims, 49 Drawing Sheets

5-METHOXY-N,N-DIMETHYLTRYPTAMINE (5-MeO-DMT) FORMULATIONS

FIELD OF THE INVENTION

This invention relates to 5-methoxy-N,N-dimethyltryptamine (5-MeO-DMT) formulations, more particularly intranasal formulations of pharmaceutically acceptable salts of 5-MeO-DMT, and methods of administration and treatment using the same.

BACKGROUND OF THE INVENTION 5-methoxy-N,N-dimethyltryptamine is a pharmacologically active compound of the tryptamine class and has the chemical formula:

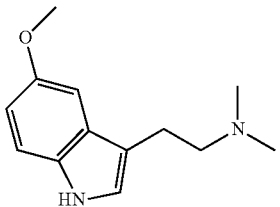 [SMILES: COc1ccc2[nH]cc(CCN(C)C)c2c1]

5-MeO-DMT is a psychoactive/psychedelic substance found in nature. Man-made salts of 5-MeO-DMT are also known in the art e.g. Sherwood, Alexander M., et al. "Synthesis and Characterization of 5-MeO-DMT succinate for clinical use." ACS omega 5.49 (2020): 32067-32075 discloses the hydrochloride salt of 5-MeO-DMT. However, 5-MeO-DMT, and salts thereof, are not well understood and methods of administration, in particular intranasal methods of administration of dry powder formulations of this compound, and the salts thereof, have not been well explored.

For example, it has been found that liquid intranasal formulations of the hydrochloride salt of 5-MeO-DMT experience issues relating to stability, discolouration and a reduction in desirable pharmacokinetic properties. For the sake of brevity, the term '5-MeO-DMT' used herein, may also be understood to be referring to the salts of 5-MeO-DMT.

5-MeO-DMT is not suitable for oral delivery and so other methods of administration have been considered. Other methods of administration are possible e.g. intravenous and inhalation by smoking. Intranasal administration, e.g. nasal liquid spray formulation, is also another way of providing systemic drug delivery across the blood brain barrier, in particular when oral administration is not effective.

There remains a need in the art for improved formulations, in particular intranasal formulations, comprising 5-MeO-DMT and the salts thereof, and methods of administration and treatment using the same.

SUMMARY OF THE INVENTION

Herein disclosed, there is provided a dry powder formulation, produced by spray drying, lyophilisation or hot melt extrusion, wherein the formulation comprises 5-MeO-DMT, or a pharmaceutically acceptable salt thereof, and one or more pharmaceutically acceptable carriers or excipients. Beneficially, spray drying, lyophilisation or hot melt extrusion provide an intimate mix of the 5-MeO-DMT salt with any of the carriers, excipients or any other additives.

In a first aspect, there is provided a state-stable amorphous dry powder formulation comprising 5-MeO-DMT HBr (the hydrobromide salt of 5-MeO-DMT) and one or more pharmaceutically acceptable carriers or excipients. Beneficially, the amorphous state does not revert to a crystalline form, and so the nature of the formulation is well understood.

In an embodiment, the formulation is a spray dried formulation. In an embodiment, no more than 80% of the 5-MeO-DMT is released from the formulation by 4 minutes in water at 37° C. In an embodiment, no more than 80% of the 5-MeO-DMT is released from the formulation by 5, 6, 7, 8, 9 or 10 minutes in water at 37° C. In an embodiment, no more than 80% of the 5-MeO-DMT is released from the formulation by 5, 6, 7, 8, 9 or 10 minutes in a simulated nasal fluid. Beneficially, the 5-MeO-DMT is not released immediately, and indeed released relatively slowly. Beneficially, the person being treated receives the active substance over a duration of time. On some occasions, receiving the active substance, a psychoactive substance, over a very short period of time can be quite intense.

In an embodiment, at least 95% of the particles of the formulation are larger than 10 microns in size. Beneficially, the formulation does not substantially contain respirable fines (undesirable particles that could enter the lungs).

In an embodiment, the 5-MeO-DMT HBr is non-hygroscopic. In an embodiment, the formulation comprises below about 5% moisture content by weight of the formulation. In an embodiment, the formulation is a free flowing formulation. Beneficially, non-hygroscopic salts are easy to handle and formulate, these tend to be free-flowing, and are less prone to decomposition.

In an embodiment, greater than 70% (w/w) of the 5-MeO-DMT HBr in the formulation is in an amorphous form. In an embodiment, the formulation comprises at least about 10%, 20%, 30%, 40%, 50%, 60%, 70%, 80%, 90%, 95% or 99% by weight 5-MeO-DMT HBr.

In an embodiment, upon administration to a nasal cavity of a subject the formulation exhibits a residence time. In an embodiment, the length of time a substance is present in nasal cavity, for example along the nasal cilia and mucus layer, in the nasal cavity of at least 10, 15, 20, 25 or 30 minutes. Beneficially, the person being treated receives the active substance over a duration of time. On some occasions, receiving the active substance, a psychoactive substance, over a very short period of time can be quite intense.

In an embodiment, the formulation comprises a cellulose like/based excipient; optionally HPMC, further optionally a high viscosity HPMC, still further optionally a high viscosity HPMC. In an embodiment, the formulation comprises a low viscosity HPMC and a high viscosity HPMC. In an embodiment, wherein the ratio of the low viscosity HPMC to high viscosity HPMC is in the ratio of 1:10 to 10:1, optionally 1:4 to 4:1 and further optionally 1:2 to 2:1. In an embodiment, the ratio of the low viscosity HPMC to high viscosity HPMC is in the ratio of 50:50, 45:55, 40:60, 35:65, 30:70 or 25:75. In an embodiment, the high viscosity HPMC has a viscosity greater or equal to about 20, 30, 40, 50 or 60 megaPascals, optionally where the HPMC is a HPMC containing about 7.0-12.0% hydroxypropyl content, about 28.0-30.0% methoxy content, and a viscosity of about 50 mPas. In an embodiment, the low viscosity HPMC has a viscosity less than about 20, 15, 10, 5, 1 megaPascals, optionally where the HPMC is a HPMC containing about 7.0-12.0% hydroxypropyl content, about 28.0-30.0% methoxy content, and a viscosity of about 4.8-7.2 mPas. In an embodiment, the formulation comprises a polyol, optionally the polyol is mannitol, xylitol, sorbitol, maltitol, erythritol, lactitol or isomalt, further optionally the polyol is sorbitol. In an embodiment, the formulation comprises about 1-10%, 2-5% or 3% polyol by weight, optionally about 3% sorbitol by weight.

In an embodiment, there is provided a nasal delivery device comprising the formulation. In an embodiment, the proportion of the active substance (5-MeO-DMT), in the active substance salt is greater than about 65, 70 or 80% (i.e. using a counter ion of smaller relative molecular mass). Beneficially, in a device with a small delivery chamber, a high proportion of active in the salt is desirable. Similarly, the higher the proportion of the salt in the particles is desirable.

In an embodiment, there is provided a method of treating depression and/or alcohol use disorder in a subject in need thereof, the method comprising intranasally administering to the subject the formulation in an amount sufficient to treat the depression and/or alcohol use disorder. In an embodiment, there is provided a method of making the formulation, the method comprising (i) mixing the components of the formulation with a liquid to form a mixture and spray drying the mixture to form a solid; and (ii) following following step (i), further drying the solid to form the formulation and optionally wherein the drying step is performed at between 45 and 15° C. and between 85% to 65% relative humidity (RH); between 35 and 20° C. and between 80% to 70% RH; and further optionally at 25° C. and 75% RH.

In an embodiment, the formulation comprises about:
40-60% by weight 5-MeO-DMT HBr;
30-40% by weight a HPMC containing about 7.0-12.0% hydroxypropyl content, about 28.0-30.0% methoxy content, and a viscosity of about 4.8-7.2 mPas;
7-15% by weight a HPMC containing about 7.0-12.0% hydroxypropyl content, about 28.0-30.0% methoxy content, and a viscosity of about 50 mPas; and
0-5% by weight sorbitol.

In an embodiment, the 5-MeO-DMT, or a pharmaceutically acceptable salt thereof, is in an amorphous (non-crystalline) form. In an embodiment, the formulation is a stable free flowing formulation.

In an embodiment, the formulation is a state-stable free flowing formulation. In an embodiment, the formulation comprises at least about 10%, 20%, 30%, 40%, 50%, 60%, 70%, 80%, 90%, 95% or 99% by weight 5-MeO-DMT, or a pharmaceutically acceptable salt thereof. In an embodiment, the formulation exhibits an extended release profile, optionally having a residence time in the nasal cavity of at least 10, 15, 20, 25 or 30 minutes. In an embodiment, the formulation exhibits an extended release profile, wherein 80% of the 5-MeO-DMT active agent is released over a period of time of about 2 to 40, optionally 3 to 30, further optionally 4 to 15 minutes.

In an embodiment, the formulation comprises a cellulose like/based excipient; optionally HPMC, further optionally a high viscosity HPMC, still further optionally a high viscosity HPMC. In an embodiment, the formulation exhibits an extended release profile. In an embodiment, the formulation comprises a cellulose like/based excipient; optionally HPMC, further optionally a high viscosity HPMC, still further optionally a high viscosity HPMC, and wherein the formulation exhibits an extended release profile. In an embodiment, the formulation exhibits an extended release profile when compared with a formulation without the cellulose like/based excipient. In an embodiment, the formulation comprises a low viscosity HPMC and a high viscosity HPMC. In an embodiment, the formulation exhibits an extended release profile.

In an embodiment, the formulation comprises a low viscosity HPMC and a high viscosity HPMC, and wherein the formulation exhibits an extended release profile. In an embodiment, the ratio of the low viscosity HPMC to high viscosity HPMC is in the ratio of 1:10 to 10:1, optionally 1:4 to 4:1 and further optionally 1:2 to 2:1. In an embodiment, the ratio of the low viscosity HPMC to high viscosity HPMC is in the ratio of 50:50, 45:55, 40:60, 35:65, 30:70 or 25:75. In an embodiment, the ratio of the low viscosity HPMC to high viscosity HPMC is in the ratio of 50:50, 45:55, 40:60, 35:65, 30:70 or 25:75 and wherein the formulation exhibits an extended release profile. In an embodiment, wherein the high viscosity HPMC has a viscosity greater or equal to about 20, 30, 40, 50 or 60 megaPascals, optionally where the HPMC is metolose 60SH50.

In an embodiment, the low viscosity HPMC has a viscosity less than about 20, 15, 10, 5, 1 megaPascals, optionally where the HPMC is pharmacoat 606. In an embodiment, the formulation comprises a polyol, optionally the polyol is mannitol, xylitol, sorbitol, maltitol, erythritol, lactitol or isomalt, further optionally the polyol is sorbitol. In an embodiment, the formulation comprises about 1-10%, 2-5% or 3% polyol by weight, optionally about 3% sorbitol by weight.

In an embodiment, the formulation comprises 5-MeO-DMT hydrochloride, optionally the salt is in an amorphous form, further optionally a state-stable amorphous form. In an embodiment, the formulation comprises 5-MeO-DMT hydrobromide, optionally the salt is in an amorphous form, further optionally a state-stable amorphous form. In an embodiment, the formulation comprises 5-MeO-DMT benzoate, optionally the salt is in an amorphous form, further optionally a state-stable amorphous form. In an embodiment, the formulation comprises 5-MeO-DMT oxalate, optionally the salt is in an amorphous form, further optionally a state-stable amorphous form. In an embodiment, the formulation comprises 5-MeO-DMT phosphate, optionally the salt is in an amorphous form, further optionally a state-stable amorphous form. In an embodiment, the formulation comprises 5-MeO-DMT fumarate, optionally the salt is in an amorphous form, further optionally a state-stable amorphous form.

In an embodiment, the formulation comprises a non-hydroscopic 5-MeO-DMT salt, optionally the salt is in an amorphous form, further optionally a state-stable amorphous form. In a further aspect of the invention, there is provided a nasal delivery device comprising the formulations herein described, and/or in any aspect or embodiment of the invention. In an embodiment, the device is single use. In an embodiment, the device contains a single dose of the formulation. In an embodiment, the formulation or nasal delivery device is for use as a medicament.

In an embodiment, the formulation or nasal delivery device is for use in a method of treatment of depression and/or alcohol use disorder. In an embodiment, the formulation is produced by spray drying and wherein following the spray drying of the formulation, an additional drying step is performed to condition the formulation. In an embodiment, the drying step is performed at between 45 and 15° C. and between 85% to 65% relative humidity (RH); optionally between 35 and 20° C. and between 80% to 70% RH; and further optionally at 25° C. and 75% RH.

In an embodiment, there is provided a dry powder formulation, produced by a method of spray drying, wherein the formulation comprises about:
50% by weight 5-MeO-DMT, or a pharmaceutically acceptable salt thereof;

35% by weight HPMC 606;
12% by weight Metolose 60 SH 50; and
3% by weight sorbitol.

Liquid intranasal administration is one way of providing systemic drug delivery across the blood brain barrier. However, one of the challenges faced with these liquid formulations is the limited residence time in the nasal cavity. The mucociliary clearance mechanism is responsible for this limited residence time, the movement of the nasal cilia leads the upper gel-like mucus layer in the epithelia to move with a velocity of about 6 mm/min towards the nasopharynx and throat. As such, such liquid formulations are rapidly removed from the nasal cavity. In addition, some liquid intranasal formulations of 5-MeO-DMT, can have stability issues, e.g. discolouration and/or a reduction in desirable pharmacokinetic properties.

Some attempts have been made to develop dry powder formulations for intranasal administration which overcome the problems associated with liquid formulations. However, this has proved challenging. The first intranasal dry powder formulations were approved by the Food and Drug Administration in 2016 and 2019 for Onzentra (containing Sumatriptan) and Baqsimi (containing Glucagon) respectively. Onzentra uses a passive administration device and Baqsimi uses an active device; and so work was needed to find a formulation and device that in each case would work well in concert.

In addition, some 5-MeO-DMT salts have been found to be very soluble in water (e.g. some crystalline forms of the halide salts of 5-MeO-DMT have a solubility of >400 mg/ml in water) and have very rapid dissolution profiles. While these properties can be desirable in solid oral or intravenous dosage formulations, they are not necessarily beneficial for intranasal formulations of 5-MeO-DMT.

This is because 5-MeO-DMT can provide a very intense Mystical Experience in a subject. So, for a highly soluble intranasal formulation that rapidly crosses the blood brain barrier (e.g. 80% of the dose of the active agent in under about 4 minutes) the Mystical Experience generated may happen very quickly, and can be quite intense, cause irritation, and this may be unsettling for some users.

The applicant has beneficially found that dry powder formulations of 5-MeO-DMT (and the salts described herein), in particular amorphous dry powder formulations of the same, address and/or ameliorate the problems encountered in the prior art as discussed further herein below.

The applicant has beneficially found that the following factors (not necessary listed in the order of importance) provide beneficial properties when making dry powder formulations of 5-MeO-DMT: amorphous (non-crystalline) form/state; moderate/lower solubility forms; excipients/agents that slow/retard the dissolution of the active agent across the nasal blood brain barrier (e.g. in particular cellulose like/based excipients like HMPC and (methyl)cellulose). As such, the applicant has sought to increase the residency time of the active agent (5-MeO-DMT) in the nasal cavity. Other modifications have not proved effective and indeed in some case have lessened the residency time in the nasal cavity. Also, when matching the formulation to a dry powdered delivery device, the proportion of the active agent in the formulation should be relatively high (so a smaller formula weight counter ion can be beneficial, as is a low proportion of any excipient/additives), e.g. to maximize the proportion of the active agent in the delivery vehicle, which may need to fit within a relatively small delivery chamber in the delivery vehicle (e.g. holding a volume of less than about 0.05 ml). Also, beneficially, the amorphous (non-crystalline) form/state should be state-stable e.g. it should not (re)crystalize, in particular upon storage. More beneficially, the amorphous (non-crystalline) form/state should be state-stable at or above room temperature e.g. it should not (re)crystalize when stored at about above 0, 5, 10, 15, 20, 25, 30 or 35° C. Also, the cellulose like/based excipients may have a viscosity to suit need, e.g. high, moderate or low viscosity or contain a mixture of these with different viscosities (e.g. a high and low viscosity). Without being bound by theory, it is possible that the 5-MeO-DMT is preferentially soluble in the cellulose like/based excipients, and this delays/retards the API (i.e. 5-MeO-DMT) travelling across the nasal blood brain barrier. Advantageously, the formulation should be free from respirable API fines (e.g. which may enter the lungs) and/or significant amounts of any aggregation. Respirable fines are particles which are 10 microns or less. In an embodiment, the formulation comprises particles which are larger than 10 microns. In an embodiment, the formulation is substantially free of respirable fines. In an embodiment, 75, 80, 90, 95, 98, 99, 99.5, 99.8 or 99.9% of the particles of the formulation are larger than 10 microns.

In an embodiment the formulation comprises particles having a median diameter of less than 2000 μm, 1000 μm, 500 μm, 250 μm, 100 μm, 50 μm, or 1 μm. In an embodiment, the particles have a median diameter of greater than 500 μm, 250 μm, 100 μm, 50 μm, 40 μm, 30 μm, 25 μm, 20 μm, 15 μm, 10 μm, 5 μm, 1 μm or 0.5 μm. In an embodiment formulation has a particle size distribution of d10=20-60 μm, and/or d50=80-120 μm, and/or d90=130-300 μm.

It is considered that a formulation could be prepared that contained a slow release element/portion and a standard release element/portion (e.g. a mixture of amorphous and partially crystalline 5-MeO-DMT (the API)), such that there is an initial release of the API (e.g. a lower amount), followed by a slower release of the API (e.g. a larger amount).

In an embodiment, the formulation comprises crystalline API dry blended with SDD comprising API/HPMC. Beneficially, this may provide for higher drug loadings within a single device.

Herein disclosed, the formulation is free from the one or more pharmaceutically acceptable carriers or excipients.

DESCRIPTION OF THE INVENTION

In an embodiment, there is provided a dry powder formulation comprising 5-MeO-DMT, or a pharmaceutically acceptable salt thereof, and polyvinylpyrrolidone (PVP).

Herein disclosed, there is provided a method of production of a formulation of 5-MeO-DMT comprising the steps of:
  a. Atomisation of a liquid mixture comprising 5-MeO-DMT to produce droplets;
  b. Contact between a hot gas and the droplets to dry the droplets;
  c. Optionally, the separation of the dried product from the drying medium; and
  d. Conditioning of the dried product.

In an embodiment, the conditioning step comprises exposing the dried product to between 15 to 45° C. and between 65% to 85% relative humidity (RH); optionally between 20 and 35° C. and between 70 to 80% RH; and further optionally 25° C. and 75% RH.

In an embodiment, the conditioning step takes place for between 1 day and several weeks. In an embodiment, the conditioning step takes place for between 1 day and 1 week.

In an embodiment, the conditioning step takes place for between 1 day and 3 days. In an embodiment, the conditioning step takes place for less than 1 day.

In an embodiment, there is provided a formulation as described previously or subsequently. In an embodiment, the formulation is produced by spray drying, lyophilisation and/or hot melt extrusion.

Unless otherwise stated herein all X-ray powder diffractograms (XRPD) were generated using an X-ray wavelength of 1.5406 Å; all modulated differential scanning calorimetry (DSC) thermograms were generated using a 2° C./min heating rate.

The applicant has beneficially found that in order to slow the dissolution rate, and therefore increase the residency time in the nasal cavity, the dry powder formulation should optionally include one or more suitable excipient.

Hydroxypropyl methylcellulose (HPMC) or hypromellose refers to soluble methylcellulose ethers and is approved as an inactive ingredient. Without being bound by theory, HPMC is believed to act as a viscosity enhancer, and delays/slows mucociliary clearance. HPMC polymers for fabricating hydrophilic matrix systems are available in various viscosity grades ranging from 4000-100,000 mPas. The polymer chain length, size and degree of branching determine the viscosity of the polymer in solution.

Different grades of HPMC (with lower viscosities than that above) are also available according to their particle size distribution, viscosity, molecular weights, and substitution of methoxy and hydroxypropyl groups.

For the purposes of this application a high viscosity HPMC would generally be considered to be one with a viscosity grade of 20 mPas or above.

For the purposes of this application a low viscosity HPMC would generally be considered to be one with a viscosity grade of less than 20 mPas.

HPMC 2910 has an average content of methoxy groups of 29% and hydropropoxy groups of 10% (hence the nomenclature of 2910). Pharmacoat is a brand of low viscosity HPMC 2910, with Pharmacoat 606 (as commercially available in the UK as of 1 Jun. 2023) has a viscosity of 6 mPas. Metolose is a brand of high viscosity HPMC 2910 and methyl cellulose. Metoloso 60SH50 606 (as commercially available in the UK as of 1 Jun. 2023) has a viscosity of 50 mPas Dry Blending Dry blending (giving a solid dispersion matrix) of cellulose based excipients, such as HPMC 2910, with the API at high concentrations up to approximately 95% wt:wt (excipient to 5-MeO-DMT) in the blend, beneficially slowed the dissolution release rate of the API relative to an unblended formulation.

Care is needed when making dry blends to ensure blend uniformity and monitoring of any aggregation/agglomeration may be needed. Also, the nature of the blend needs to be assessed to ensure the physical properties work well with the delivery device and with scale up, e.g. if the resultant blend is prone to static charge build up, then the blend can be difficult to load into the delivery device without losses.

The applicant also found that an intimate mix formulations of the API with excipients gave beneficial properties. Intimate mix formulation (e.g. spray drying, lyophilisation and/or hot melt extrusion with one or more suitable pharmaceutical excipients or carriers) are considered further below. These techniques are best known for generating amorphous solid dispersions with improved bioavailability and increased solubility. In the present case, with the intense Mystical Experiences associated with the API, this would not on the face of it appear beneficial. Typically such dispersions comprise API loading of around 20% wt:wt (e.g. 5-MeO-DMT to excipients) or below.

Lyophilisation Formulations

Amorphous 5-MeO-DMT salt formulations have been produced via lyophilisation processes. It is noted that in some cases these have low glass transition temperatures. Conversion to a crystalline form may therefore occur, perhaps rapidly. Solubility studies utilising a lyophilised amorphous form of 5-MeO-DMT benzoate showed an almost instantaneous dissolution rate, which would have applications where this was a desirable property.

Hot-Melt Formulations

Hot melt extrusion may be utilised to produce 5-MeO-DMT formulations according to the current invention and/or any embodiments thereof. Hot melt extrusion is the processing of polymeric materials above their glass transition temperature (Tg) in order to effect molecular level mixing of thermoplastic binders and/or polymers and active compounds.

Spray Dried Dispersions

Spray drying typically involves injecting a liquid composition of material into a chamber for contact with a drying fluid which is concurrently flowed through the chamber. The injected wet material in the form of droplets contacts the stream of drying fluid so that the liquid passes from the droplets to the drying fluid stream, producing a spray dried product that is discharged from the drying chamber, and drying fluid effluent that likewise is discharged from the drying chamber.

Advantageously, and unexpectedly, the applicant discovered that spray dried dispersions of 5-MeO-DMT gave products with lower/reduced dissolution rates. This was unexpected because spray dried dispersions are generally developed to improve the solubility of low solubility products. The expectation was that the small particles produced by spray drying would have a larger surface area, which allows them to dissolve more easily in the body.

That said, there is a limit to the amount of product that can be administered to the nasal cavity through a medical device, typically below 50 mg (approximately 0.05 ml in volume). In the case of 5-MeO-DMT dry powder formulations, it is envisaged that single doses of up to 20 mg or above API may be needed, which may require an API loading of for example 50% wt:wt, levels which are not typically seen in spray dried solid dispersions.

Below, more specific sprayed dried formulations are considered.

5-MeO-DMT Benzoate|Spray Dried Powder Formulation

Spray dried powder formulations containing excipient(s) and the benzoate salt of 5-MeO-DMT were produced, which contained dried particles of suitable size for intranasal administration and surprisingly, a reduced dissolution rate as compared to the amorphous form of 5-MeO-DMT salts.

Respirable particles, particles which can penetrate beyond the terminal bronchioles into the gas-exchange region of the lungs are undesirable as they can, for example, trigger bronchoconstriction in asthmatics. In addition, uncontrolled recrystallisation over time within the spray dried dispersion particles may also lead to aggregation of the particles.

With this benzoate salt, the applicant has found that storage at 2-8° C., and protection from moisture, prevents recrystallisation and aggregation. In this case, it was found that a post spray drying step (conditioning the spray dried dispersion particles) at 25° C./75% RH produced a stable crystalline spray dried dispersion particle with no respirable API fines or significant aggregation.

It was also discovered that producing a spray dried dispersion with reduced amount of the benzoate salt loading (e.g. API loading to approximately 20% wt:wt) produced an amorphous dispersion with no sign of the crystalline benzoate salt.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion.

5-MeO-DMT Oxalate|Spray Dried Powder Formulation

A spray dried powder formulation of 5-MeO-DMT oxalate (50% API loading) and excipient(s) was produced and yielded partially crystalline particles (see Example 2). Without being bound by theory, it is believed that lowering the API content (as was the case with the Benzoate salt) could produce an amorphous dispersion with no sign of the crystalline salt.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion.

5-MeO-DMT Hydrobromide|Spray Dried Powder Formulation

A spray dried powder formulation of 5-MeO-DMT hydrobromide (50% API loading) and excipient(s) was produced. Surprisingly, this formulation was found to be a stable amorphous dispersion without the need for any additional drying step post spray drying. It was also state-stable when stored at above the temperature range 2-8° C.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion. In an embodiment, the formulation is non-hygroscopic.

Extended Release Formulations of the Salts of 5-MeO-DMT

Recent clinical trials undertaken by the applicant have identified the desirability of an extended release formulation of 5-MeO-DMT (or salts thereof) suitable for intranasal administration. The applicant has surprisingly discovered that the use of higher viscosity excipients, within a spray dried dispersion as described previously or subsequently, can suitably extend the release window of the API 5-MeO-DMT.

More viscous HPMCs, such as HPMC metolose 60SH50, are not typically suitable for spray drying due to the high viscosity solutions produced as feed stock. Unexpectedly, it has been found that spray drying 5-MeO-DMT with a mixture of a high viscosity HPMC and a lower viscosity HPMC (such as pharmacoat 606) produces spray dried dispersion droplets in which the dissolution of the API from the formulation is slowed.

Various ratios of high viscosity HPMC to low viscosity HPMC have been investigated and it was discovered that the dissolution rate of the API did not significantly differ between a ratio of 50:50 high:low HPMC and a ratio of 25:75 high:low HPMC. The formulations comprising a lower amount overall of high viscosity HPMC are more amenable to the spray drying process (e.g. lower viscosity feed stock).

It was noted that the products obtained with a single HPMC had yields that were higher than products obtained with mixed HPMC products in the spray drying process described above. Further investigation found that, beneficially, that the addition of a polyol to the formulation with the mixed HPMCs, improved the resultant yields (e.g. by as much as about 18% compared with a formulation lacking the polyol). Beneficially and unexpectedly, the addition of the polyol has no appreciable effect on the dissolution rate of the API in the formulation.

In an embodiment an additive such as a polyol or surfactant etc. is added to the formulation prior to spray drying. In an embodiment, the formulation comprises two (or more) different HPMCs. In an embodiment, the formulation comprises two (or more) different HPMCs where these have different viscosities. In an embodiment, the formulation comprises two (or more) different HPMCs. In an embodiment, the formulation comprises two (or more) different HPMCs where these have different viscosities, and wherein the net viscosity of the mixture is spray dryable. In an embodiment, the formulation comprises two (or more) different HPMCs where these have different viscosities, wherein the net viscosity of the mixture is spray dryable, and wherein at least one of the HPMCs alone would not be readily suitable for spray drying.

In an embodiment, there is provided an extended release dry powder formulation of 5-MeO-DMT comprising a mixture of a high viscosity HPMC and a low viscosity HPMC. In an embodiment, the extended release dry powder formulation comprises a ratio of 1:1 of the high and low HPMC. In an embodiment, the ratio is 1:2 of high to low HPMC. In an embodiment, the ratio is 1:3 of high to low HPMC.

In an embodiment, the formulation further comprises a polyol (e.g. an organic compound, e.g. 4 to 12 carbon atoms, and containing multiple hydroxyl groups (—OH)). Optionally containing 4 to 6 carbon atoms. Some of these are polyether, polyester, polycarbonate and also acrylic polyols. Polyether polyols may be further subdivided and classified as polyethylene oxide or polyethylene glycol (PEG), polypropylene glycol (PPG) and Polytetrahydrofuran or PTMEG. These have 2, 3 and 4 carbons respectively per oxygen atom in the repeat unit. Polycaprolactone polyols are also available. Polyols may be biobased and hence renewable.

In an embodiment, the polyol is selected from mannitol, xylitol, sorbitol, maltitol, erythritol, lactitol or isomalt.

In an embodiment, the polyol is sorbitol. In an embodiment, the formulation comprises by weight 3% sorbitol.

In an embodiment, the extended release dry powder formulation is produced by spray drying In an embodiment, the production method comprises addition of a polyol e.g. sorbitol or mannitol or combinations of both (e.g. isomalt).

Low Crystalline Content Spray Dried Dispersions

Beneficially, the applicant has discovered that reducing the relative 5-MeO-DMT salt loading of the spray dried dispersion formulation leads to a reduction in salt crystalline content (and hence an overall increase in the amorphous content present in the dispersion). The level of crystalline content was determined using a higher than normal heating rate DSC method and the crystalline content was comparable to that of the low viscosity HPMC formulations. The increased amorphous API content in these formulations surprisingly led to a reduction in the dissolution rate of the formulation. This is contrary to the expected result, wherein amorphous solid dispersions are manufactured with the aim of enhancing the solubility and dissolution of the formulation.

In an embodiment, the dry powder formulation has a moisture content of below about 1%, about 2%, about 3%, about 4%, about 5%, about 6%, about 7%, about 8%, about 9%, about 10% by weight of the formulation.

Non-Hygroscopic 5-MeO-DMT Hydrobromide

In an embodiment, the formulation is non-hygroscopic. It has been surprisingly found that the hydrobromide salt of 5-MeO-DMT is non-hygroscopic. Hygroscopicity is the phenomenon of attracting and holding water molecules via either adsorption or absorption from the surrounding environment. Pharmaceuticals that pick up less than 0.2% moisture at 80% RH are considered non hygroscopic. Pharmaceuticals that pick up between 0.2% and 2.0% moisture at 80% RH are considered slightly hygroscopic. Pharmaceuticals that pick up between 2.0% and 15.0% moisture at 80% RH are considered moderately hygroscopic. Pharmaceuticals that pick up more than 15.0% moisture at 80% RH are considered very hygroscopic. Hygroscopic substances are difficult to handle and costly and burdensome measures must be taken in order to ensure they are not exposed to moisture during process and formulation. Exposed to moisture, hygroscopic substances can take on water and convert to a hydrous form. This presents several disadvantages. First, the hydrous forms may have the disadvantage of being less bioavailable and less dissoluble than the anhydrous forms. Second, the variation in the amount of hydrous versus anhydrous substance from batch to batch could fail to meet specifications set by drug regulatory agencies. Third, processes like milling may cause the drug substance to adhere to manufacturing equipment which may further result in processing delay, increased operator involvement, increased cost, increased maintenance and lower production yield. Fourth, in addition to problems caused by introduction of moisture during the processing of these hygroscopic substances, the potential for absorbance of moisture during storage and handling would adversely affect the dissolubility of the drug substance. Thus shelf-life of the product could be significantly decreased and/or packaging costs could be significantly increased.

Beneficially, the non-hygroscopic properties of the 5-MeO-DMT hydrobromide additionally make it a good salt form for a dry powder formulation.

Nasal Delivery Devices

In an embodiment, there is provided a nasal powder dispenser device having a reservoir containing at least one dose of powder comprising 5-MeO-DMT, or a pharmaceutically acceptable salt thereof (inclusive of any of the aspects and/or embodiments of the invention and/or formulations as described herein). Further, the embodiment may comprise one or more of: a nasal dispenser head for inserting into a user's nostril, the nasal dispenser head including a dispenser orifice; and an air expeller that, during actuation of the nasal powder dispenser device, generates a flow of compressed air so as to dispense a dose of powder into the nostril through the dispenser orifice. In an embodiment, the air expeller has an air chamber and a piston that slides in airtight manner in the air chamber so as to compress the air contained in the air chamber. In an embodiment, in the nasal powder dispenser device, a pressure of the flow of compressed air generated by the air expeller is higher than 0.7 bar; and a volume of the air chamber is greater than about 1700 $mm^3$ (corresponding to a volume of about 12×12×12 mm).

In an embodiment, there is provided a nasal powder delivery device having a container comprising a dose of powder comprising at least particles of 5-MeO-DMT or a pharmaceutically acceptable salt thereof, a nasal delivery head, and an air discharge system generating a flow of compressed air for delivering a dose of powder into the nostril. In an embodiment, the air chamber is arranged in a skirt, and a piston sealingly slides in the air chamber to compress the air. In an embodiment, the piston is connected to an actuating member, in which, before actuation, at least one breakable bridge is provided between the skirt and the actuating member, wherein each breakable bridge is formed on the skirt and cooperates with a radial projection formed on the actuating member. In an embodiment, each radial projection has an axial extension greater than that of the respective breakable bridge and forms an inclined axial ramp on either side.

In an embodiment the device is an Aptar device (UDS—Unidose Solid) as commercially available in the UK as of 1 Jun. 2023.

Dry powder devices described in WO21005308; WO22123128; WO22171969; and WO22208014 are incorporated herein by reference.

In an embodiment, the counter ion (anion) of the 5-MeO-DMT salt is a benzoate, hydrobromide, hydrochloride, phosphate, fumarate, oxalate, tartrate, benzenesulfonate, tosylate, glycolate, ketoglutarate, malate, saccharinate or succinate salt.

In an embodiment, the formulation may contain two salts of 5-MeO-DMT, wherein the second salt of 5-MeO-DMT salt is a benzoate, hydrobromide, hydrochloride, phosphate, fumarate, oxalate, tartrate, benzenesulfonate, tosylate, glycolate, ketoglutarate, malate, saccharinate or succinate salt. The salt type can be selected by the medical practitioner or formulator to suit need and the particular circumstance of the patient being treated or the physical requirements of the formulation needed. In an embodiment one, or both salts, comprise or consist of an amorphous (non-crystalline) state. In an embodiment one, or both salts, comprise or consist of a state-stable amorphous (non-crystalline) state.

In an embodiment (one or both of) the 5-MeO-DMT salt is 5-MeO-DMT benzoate. Advantageously, the benzoate salt has shown good irritation tolerability, in particular when compared to the better known chloride salt, and has a good stability profile. In an embodiment, the 5-MeO-DMT benzoate is not crystalline. In an embodiment, the crystalline 5-MeO-DMT benzoate is characterised by one or more peaks in an X-ray powder diffraction (XRPD) diffractogram at a 2θ value of 17.5°±0.1°, 17.7°±0.1° and 21.0°±0.1° using an X-ray wavelength of 1.5406 Å.

In an embodiment (one or both of) the 5-MeO-DMT salt is 5-MeO-DMT hydrobromide, and wherein the formulation comprises substantially the same dosage amount of the active 5-MeO-DMT cation. Advantageously, the hydrobromide salt is substantially non-hygroscopic.

It should be appreciated that different salts of 5-MeO-DMT will have different formula weights. For example the hydrochloride, hydrobromide and benzoate have respectively formula weights of about 254.8 g/mol, 299.2 g/mol, 340.4 g/mol and the free base of 5-MeO-DMT 218.3 g/mol. So, this is the amount of substance that is required to give 1 mol of the active agent. So, for example for the salt, the dosage amount may be the equivalent amount of the free base delivered when the salt is taken. So 100 mg dosage amount of 5-MeO-DMT corresponds to 117 mg of the hydrochloride salt (i.e. both providing the same molar amount of the active substance). The greater mass of the salt needed is due to the larger formula weight of the hydrogen chloride salt (i.e. 218.3 g/mol for the free base as compared to 254.8 g/mol for the salt). Similarly, for a deuterated or triturated version of 5-MeO-DMT (also considered within the scope of the invention), a slight increase in mass can be expected due to the increased formula weight of these isotopic compounds. Unless stated otherwise, the mass (mg) of 5-MeO-DMT refers to the mass of benzoate salt (and so the equivalent molar amount of the 5-MeO-DMT active agent). Accordingly, with reference to the other salts mentioned herein, the appropriate mass of the other salt can be scaled accordingly using ratios of the formula weights. These masses of salts are normally rounded up or down to suit need. This rounding may be to the nearest whole, half, quarter or tenth of a milligram (mg). For example, splitting of a combined dose will typically be done to whole numbers so 3.5 and 6.5 mg (combined total of 10 mg) may be formulated to 3 and 7 mg respectively.

In an embodiment, the composition comprises the hydrochloride, phosphate, fumarate, oxalate, tartrate, benzenesulfonate, tosylate, glycolate, ketoglutarate, malate, saccharinate or succinate salt of 5-MeO-DMT. In an embodiment, the composition does not comprises a crystalline form of the hydrochloride, phosphate, fumarate, oxalate, tartrate, benzenesulfonate, tosylate, glycolate, ketoglutarate, malate, saccharinate or succinate salt of 5-MeO-DMT.

In an embodiment, the 5-MeO-DMT is administered as the free base. In an embodiment, the 5-MeO-DMT is administered as a salt. In an embodiment, the 5-MeO-DMT is not administered as a crystalline salt. In an embodiment, the 5-MeO-DMT is not administered as a polymorphic salt form. In an embodiment, the 5-MeO-DMT is not administered as a polymorph of a 5-MeO-DMT salt. In an embodiment, the 5-MeO-DMT is administered as the benzoate, fumarate, citrate, acetate, succinate, halide, fluoride, chloride, bromide, iodide, oxalate, or triflate salt. In an embodiment, the 5-MeO-DMT is administered as the benzoate salt. In an embodiment, the 5-MeO-DMT is administered as the hydrochloride salt. In an embodiment, the 5-MeO-DMT is administered as the hydrobromide salt. In an embodiment, the 5-MeO-DMT salt is administered in an amorphous form. In an embodiment, the 5-MeO-DMT salt is not administered in a crystalline form.

In an embodiment, the 5-MeO-DMT is not administered as a crystalline form of the benzoate salt. Crystalline forms of the benzoate salt are disclosed in WO2021250434 and are incorporated herein by reference.

Crystalline forms of the hydrochloride salt are also disclosed in WO2021250434 and are incorporated herein by reference. In an embodiment, crystalline 5-MeO-DMT hydrochloride is characterised by peaks in an X-ray powder diffraction (XRPD) diffractogram at 2θ values of 9.2°±0.1°, 12.2°±0.1°, 14.1°±0.1°, 15.0°±0.1°, 18.5° 0.1°, and 19.5°±0.1°, as measured using an X-ray wavelength of 1.5406 Å.

In an embodiment, the salt anion is an aryl carboxylate. In an embodiment, the aryl carboxylate is substituted with one to three R groups. In an embodiment the one or more R groups are independently selected from: alkynyl, carbonyl, aldehyde, haloformyl, alkyl, halide, hydroxy, alkoxy, carbonate ester, carboxylate, carboxyl, carboalkoxy, methoxy, hydroperoxy, peroxy, ether, hemiacetal, hemiketal, acetal, ketal, orthoester, methylenedioxy, orthocarbonate ester, carboxylic anhydride, carboxamide, secondary, tertiary or quaternary amine, primary or secondary ketimine, primary or secondary aldimine, imide, azide, azo, cyanate, isocyanate, nitrate, nitrile, isonitrile, nitrosooxy, nitro, nitroso, oxime, pyridyl, carbamate, sulfhydryl, sulfide, disulfide, sulfinyl, sulfonyl, sulfino, sulfo, thiocyanate, isothiocyanate, carbonothioyl, carbothioic S-acid, carbothioic O-acid, thiolester, thionoester, carbodithioic acid, carbodithio, phosphino, phosphono, phosphate, borono, boronate, borino or borinate. In an embodiment the one or more R groups are independently selected from: $C_1$-$C_6$ alkyl, $C_1$-$C_6$ alkoxy, $C_1$-$C_6$ alkenyl or $C_1$-$C_6$ alkynyl, and where each of these may be optionally substituted with one to three R groups as previously described.

In an embodiment, the 5-MeO-DMT or the pharmaceutical composition comprising 5-MeO-DMT and one or more pharmaceutically acceptable carriers or excipients, is for use in a method of one or more of: treating mental disorders, in particular treatment resistant depression, major depressive disorder, persistent depressive disorder, alcohol use disorder, anxiety disorder, post-traumatic stress disorder (PTSD), body dysmorphic disorder, obsessive-compulsive disorder, eating disorder and psychoactive substance abuse.

Pharmacokinetics

In an embodiment, there is provided a salt of 5-MeO-DMT with dose-proportional pharmacokinetics, optionally for use in the methods disclosed herein. In an embodiment, the salt of 5-MeO-DMT with dose-proportional pharmacokinetics is the benzoate or HBr salt, optionally the benzoate salt. A double-blind, randomized, Phase 1, single ascending dose study to evaluate the safety, tolerability and pharmacokinetic profile of a liquid intranasal 5-MeO-DMT HCl (5-MeO-DMT HCl, HPMC, water for injection (WFI) and a sodium hydroxide solution to adjust pH) formulation in healthy subjects was performed. The mean (+/−SD) 5-MeO-DMT plasma log concentration-time plot is shown in FIG. 1. It can be seen that 5-MeO-DMT HCl does not display dose-proportional pharmacokinetics, with the mean concentration profiles displayed for 5 mg, 8 mg, 10 mg, 11 mg and 14 mg all being substantially similar.

A double-blind, randomized, Phase 1, single ascending dose study to evaluate the safety, tolerability and pharmacokinetic profile of intranasal 5-MeO-DMT benzoate in healthy subjects was performed. The mean (+/−SD) 5-MeO-DMT plasma linear concentration-time plot and plasma log concentration-time plot are shown in FIGS. 2 and 3, respectively. The pharmacokinetics were shown to be approximately dose linear. No dose exceeded the maximum exposure limits defined by previous preclinical work in dogs: Cmax: 421 ng/mL or AUC 220 h·ng/mL. The mean (+/−SD) 5-MeO-DMT plasma linear concentration-time plot and plasma log concentration-time plot are shown in FIGS. 9 and 10, respectively. The mean Cmax was 29 ng/mL for the 12 mg dosage. The mean Tmax was 9.5 minutes whilst the mean half-life (T1/2) was 21 minutes. Bufotenin, the O-demethylated metabolite of 5-MeO-DMT, was only detected at very low levels at the 6 mg dose level after the 16 minutes timepoint.

It will be understood that references to '5-MeO-DMT' herein mean 5-MeO-DMT free base, or a pharmaceutically acceptable salt, prodrug, hydrate, ester, co-crystal or deuterated form thereof, or a pharmaceutical composition comprising the aforementioned.

Definitions

As used herein, the term "free flowing" refers to the ability of the plurality of solid particles to move in unbroken continuity, similar to a fluid (e.g., the individual solid particles within a plurality of solid units do not significantly adhere or stick to one another), to permit insufflation into a nasal cavity.

As used herein, "stable" refers to the ability of the therapeutic agent (e.g., a 5-MeO-DMT) to maintain its therapeutic efficacy (e.g., all or the majority of its intended biological activity and/or physiochemical integrity) over extended periods of time. Stable formulations exhibit physical integrity and biological activity and a reduced susceptibility to chemical transformation (e.g., oxidation) prior to administration into a patient. Stable drug formulations have a shelf life at about 5° C. and/or at about 25° C. of equal to or greater than 3, 6, 12, 18, or 24 months.

As used herein, "state-stable" refers to the ability of the therapeutic agent (e.g., amorphous 5-MeO-DMT) to substantially maintain its amorphous state over an extended period of time. For example, a state-stable amorphous solid maintains at least 75%, 85%, 90%, or 95% (w/w) of its amorphous form (i.e., resisting crystallization) under storage conditions of between 2° C. and 25° C. and a relative humidity of 60% RH or below for a period of 1, 3, 6, or 12 months The term "extended-release" refers to a drug formulation that provides for gradual release of a drug over an extended period of time, e.g., 2-20 minutes or more, compared to an immediate release formulation of the same drug, such that the active agent (e.g., a 5-MeO-DMT, or a pharmaceutically acceptable salt thereof) formulated in a unit dosage form has a dissolution release profile in which at least 10-80% (e.g., 10-60%, 10-40%, 10-20%, 20-80%, 40-80%, or 60-80%) of the agent is released within the 20 minutes of testing. Preferably, although not necessarily, extended release results in substantially constant blood levels of a drug over an extended time period that are within the therapeutic range for the disease being treated. Preferably an extended release formulation of a 5-MeO-DMT yields plasma 5-MeO-DMT levels that fall within a concentration range that is between, for example, 5-45 ng/mL, 5-40 ng/mL, 5-35 ng/mL, 5-30 ng/mL, 5-25 ng/mL, 5-20 ng/mL, 10-50 ng/mL, 15-50 ng/mL, 20-50 ng/mL, 25-50 ng/mL, 30-50 ng/mL, 35-50 ng/mL, 40-50 ng/mL, 10-40 ng/mL, or 10-30 ng/mL.

By "immediate release" is meant a mode of releasing the active agent (e.g., a 5-MeO-DMT, or a pharmaceutically acceptable salt thereof) formulated in a unit dosage form that has a dissolution release profile in which at least 80%, 85%, 90%, 95%, or 99% of the agent is released within the first two minutes of testing.

As used herein, the term "residence time" refers to a time period during which a compound, such 5-MeO-DMT, is present in nasal cavity, for example along the nasal cilia and mucus layer The residence time of the compound (e.g., 5-MeO-DMT) may be formulated to have an extended residence time of at least 10 minutes, 15 minutes, 20 minutes, 25 minutes, or 30 minutes compared to an immediate release formulation which has a residence time of fewer than 10 minutes, 8 minutes, 6 minutes, 5 minutes, or 2 minutes.

As used herein, the term "treating" refers to administering the dry powder formulation for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease (e.g., depression and/or alcohol use disorder) to ameliorate the disease and improve the patient's condition. The term "treating" also includes treating a patient to delay progression of a disease or its symptoms. Thus, in the claims and embodiments, treating is the administration to a patient either for therapeutic or prophylactic purposes.

As used herein, the term "amount sufficient to" refers to a quantity of the dry formulation sufficient to, when administered to the subject, including a mammal, for example a human, effect beneficial or desired results, such as clinical results. For example, in the context of treating depression, described herein, these terms refer to an amount of the composition sufficient to achieve a treatment response as compared to the response obtained without administration of the composition. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like. An "amount sufficient to," or the like, of a composition of the present disclosure, also include an amount that results in a beneficial or desired result in a subject as compared to a control (e.g., a decrease in the score on the Montgomery-Asberg Depression Rating Scale).

EXAMPLES

Example 1: Spray Drying of 5-MeO-DMT Hydrobromide Salt with HPMC

Spray drying 5-MeO-DMT hydrobromide and HPMC (Pharmacoat 606) in water produced a 50% wt:wt API to excipient spray dried dispersion (SDD). The spray drying parameters were as below:

| Feed Solution | |
|---|---|
| Sample Reference | 30130-01-01 |
| HPMC (as Pharmacoat 606) | 1.01 g |
| 5-MeO-DMT hydrobromide | 1.05 g |
| Water (deionized) | 40.12 g |
| Spray Drying Parameters | |
| Instrument | Procept |
| Nozzle | 2 fluid nozzle |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Gas Pressure (bar) | 1.2 |
| Yield | |
| Mass of SDD Produced (g) | 1.54 |
| Yield (%) | 75 |

Figure 1:
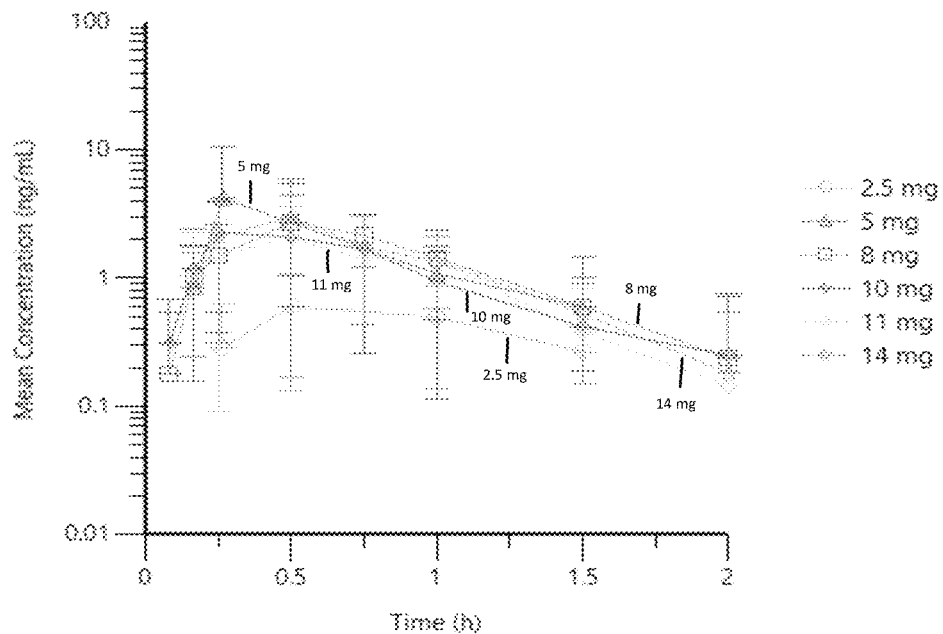
FIG. 1 shows the mean (+/−SD) 5-MeO-DMT HCl plasma log concentration-time plot.
Figure 2:
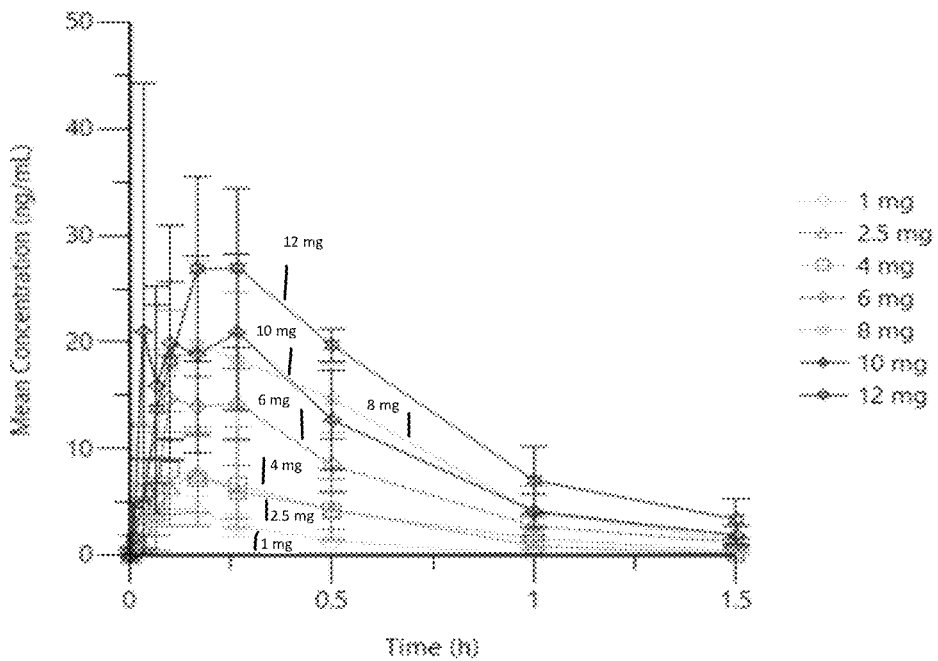
FIG. 2 shows the mean (+/−SD) 5-MeO-DMT benzoate plasma linear concentration-time plot.
Figure 3:
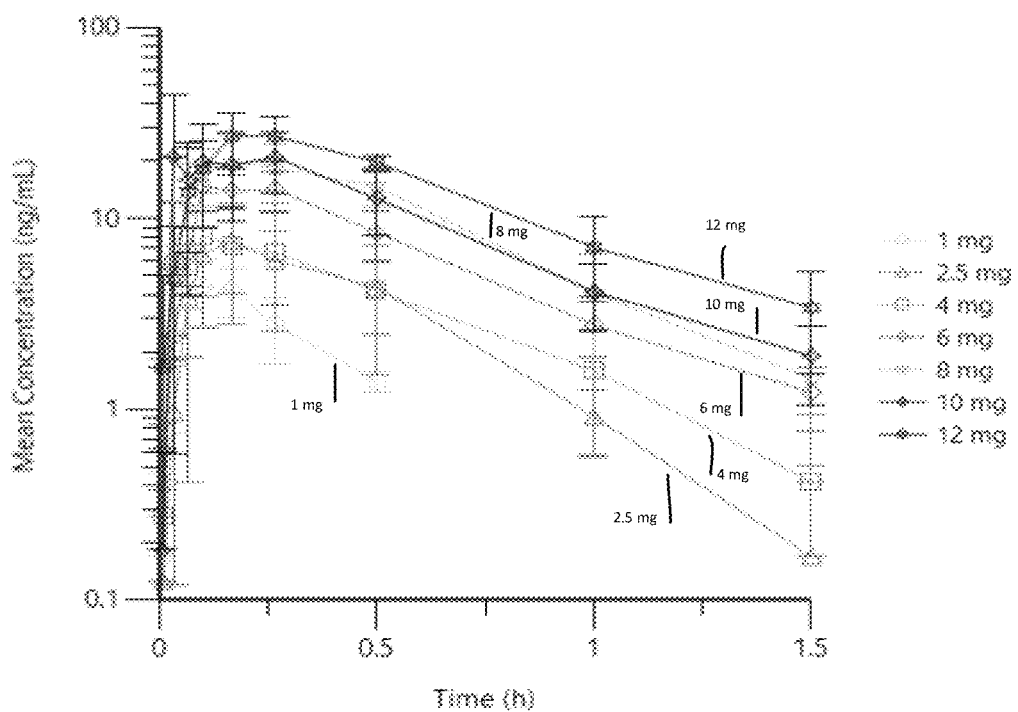
FIG. 3 shows the mean (+/−SD) 5-MeO-DMT benzoate plasma log concentration-time plot.
Figure 4:
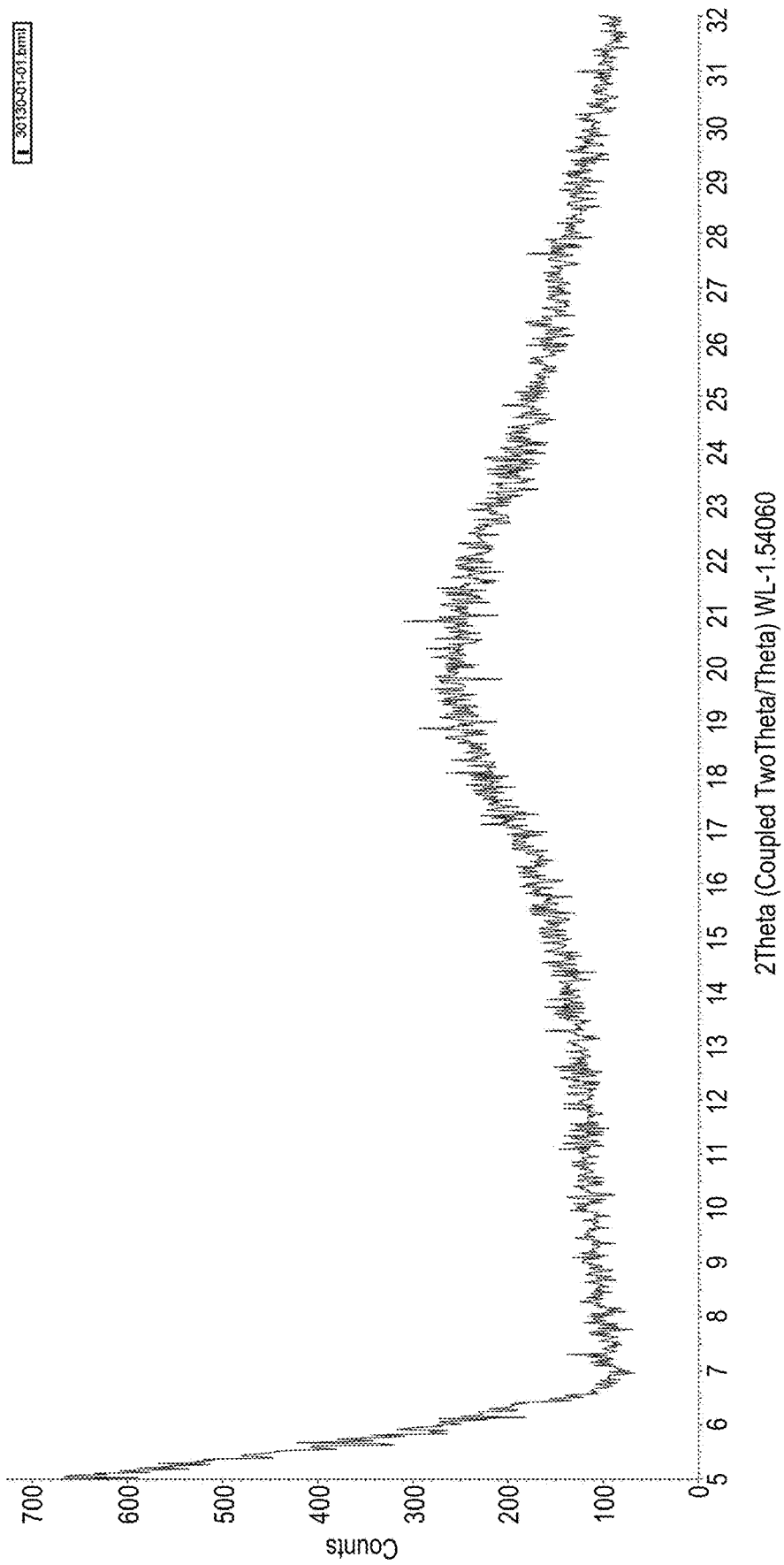
FIG. 4 shows an XRPD for the spray dried dispersion (SDD) of Example 1.
Figure 5:
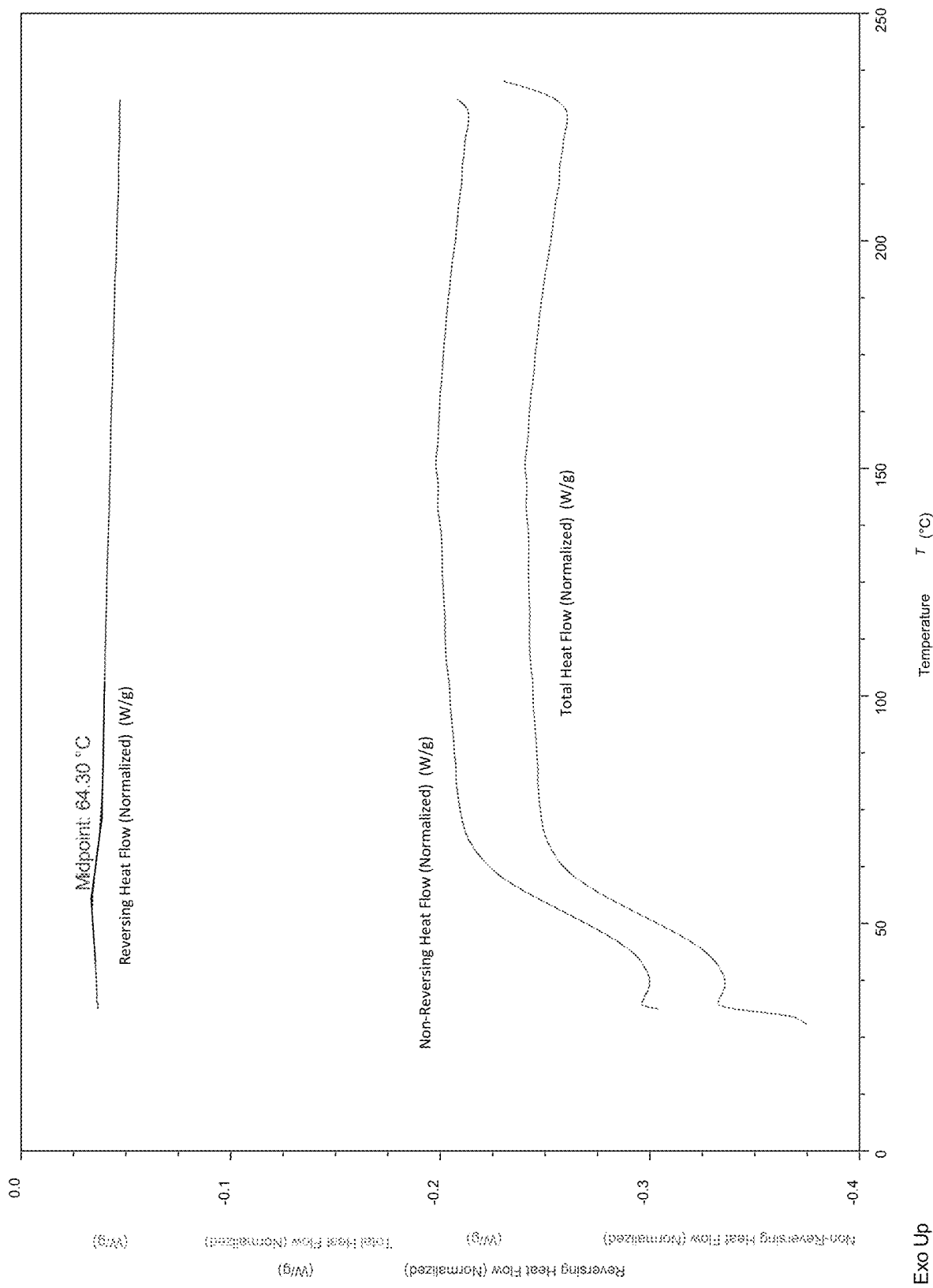
FIG. 5 shows a DSC thermogram for the SDD of Example 1.

The SDD produced was amorphous, as shown by X-ray powder diffractogram (XRPD) analysis (FIG. 4), and the absence of an enthalpy of melting when the SDD was examined by differential scanning calorimetry (DSC) (FIG. 5).

Example 2: Spray Drying of 5-MeO-DMT Oxalate Salt with HPMC

Spray drying 5-MeO-DMT oxalate and HPMC (Pharmacoat 606) in water produced a 50% wt:wt API to excipient SDD. The spray drying parameters were as below:

| Feed Solution | |
|---|---|
| Sample Reference | 31030-02-01 |
| HPMC (as Pharmacoat 606) | 1.02 g |
| 5-MeO-DMT Oxalate | 1.01 g |
| Water (deionized) | 40.01 g |
| Spray Drying Parameters | |
| Instrument | Procept |
| Nozzle | 2 fluid nozzle |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Gas Pressure (bar) | 1.2 |
| Yield | |
| Mass of SDD Produced (g) | 1.32 |
| Yield (%) | 65 |

Figure 6:
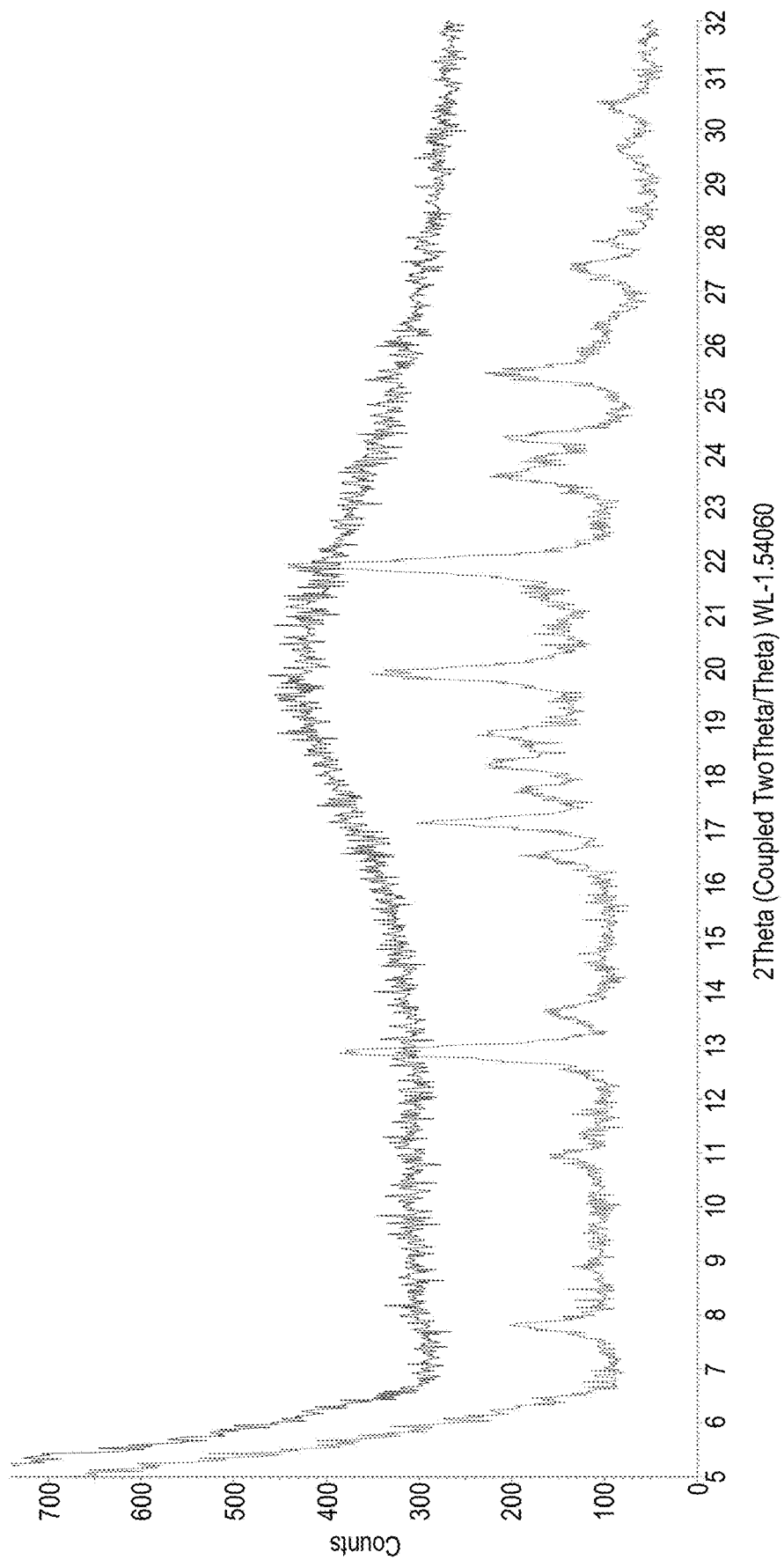
FIG. 6 shows an XRPD for the SDD of Example 2, pre and post dynamic vapour sorption (DVS).
Figure 7:
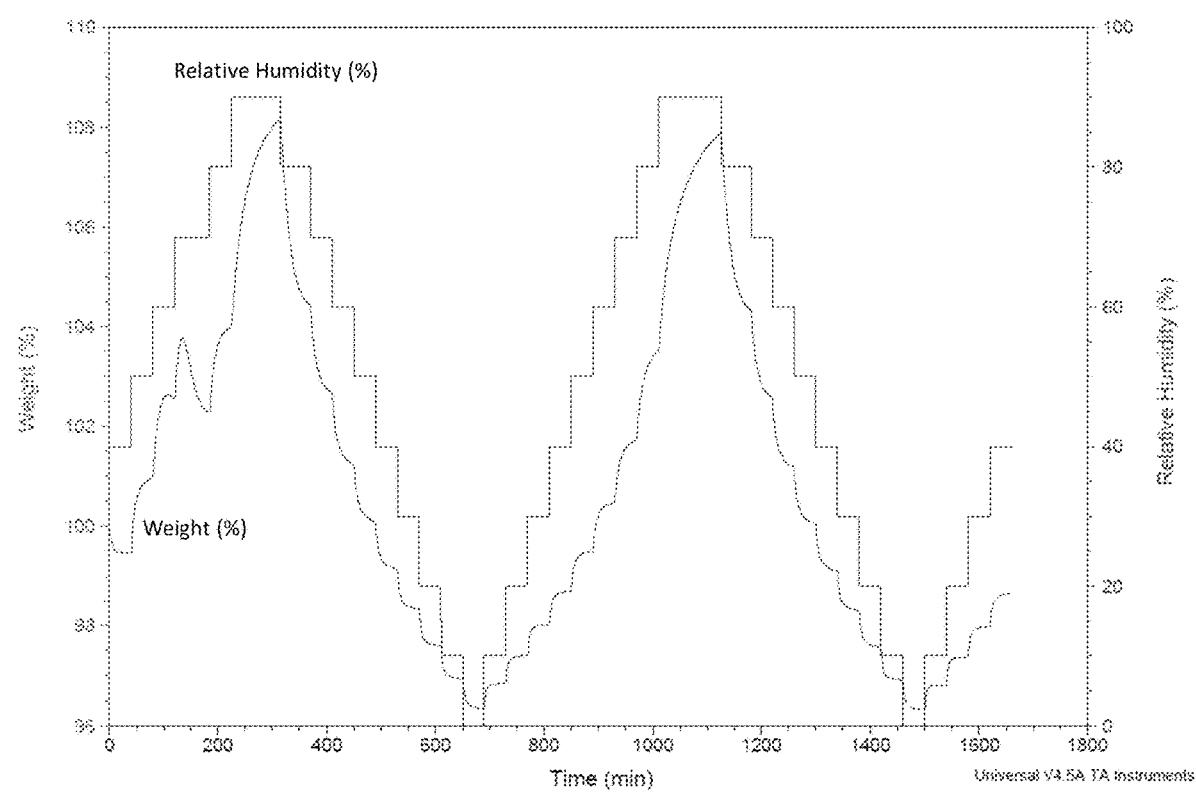
FIG. 7 shows a DVS isotherm for the SDD of Example 2.
Figure 8:
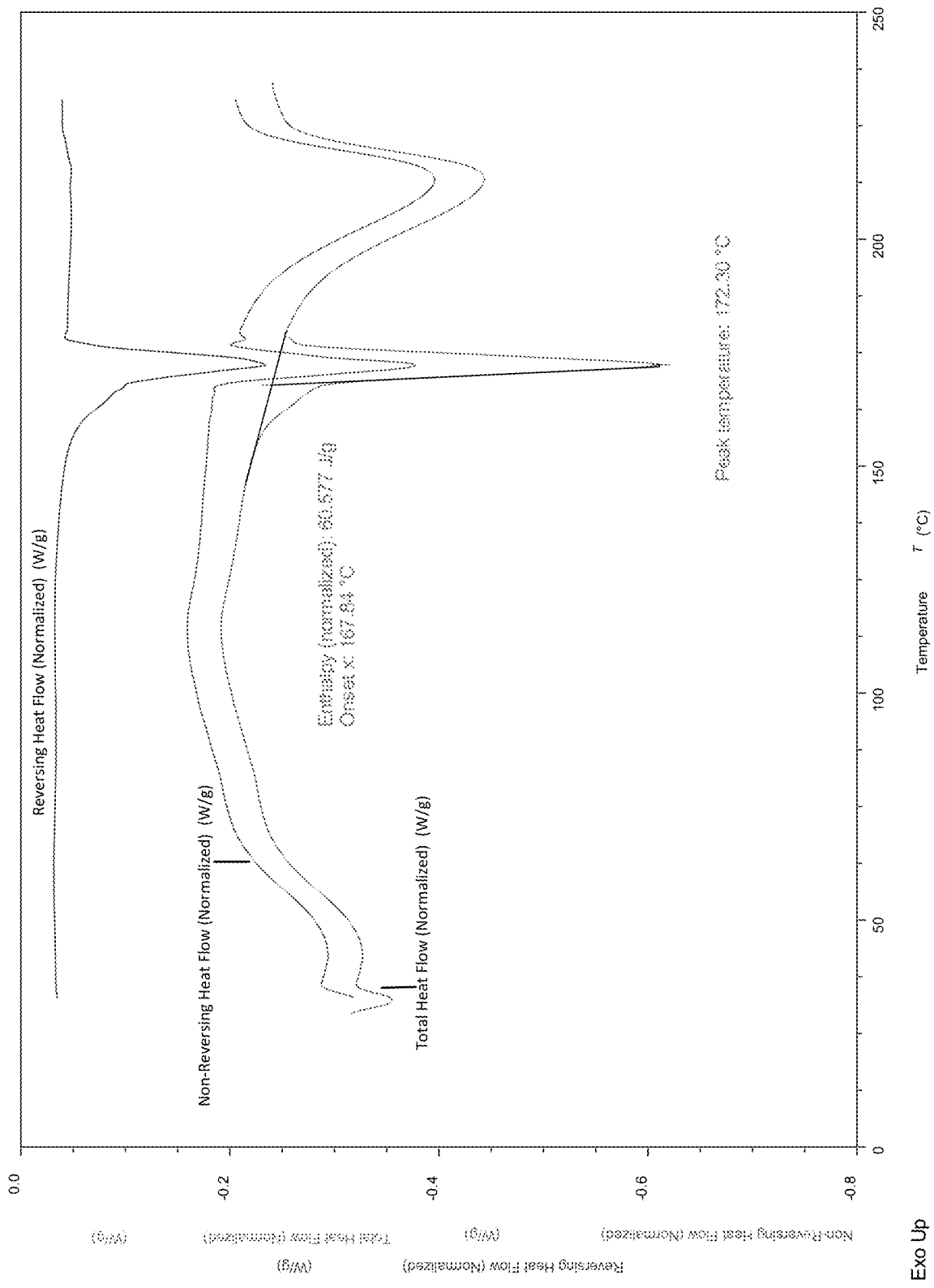
FIG. 8 shows a DSC thermogram for the SDD of Example 2.

The SDD produced was a physically state-unstable amorphous SDD that underwent recrystallization at a relative humidity of above ~60%, as shown by dynamic vapour sorption (DVS) analysis. The XRPD analysis of the SDD pre and post DVS are shown in FIG. 6, the SDD is amorphous pre DVS and partially crystalline post DVS. The DVS isotherm is shown in FIG. 7 and the DSC thermogram is shown in FIG. 8.

Example 3: Spray Drying of 5-MeO-DMT Hydrobromide Salt with PVP

Spray drying 5-MeO-DMT hydrobromide and polyvinylpyrrolidone (PVP) in water produced a 50% wt:wt API to excipient SDD. The spray drying parameters were as below:

| Feed Solution | |
|---|---|
| Sample Reference | 31030-05-01 |
| PVP K30 | 0.253 g |
| 5-MeO-DMT Hydrobromide | 0.250 g |
| Water (deionized) | 10.221 g |

| Spray Drying Parameters | |
|---|---|
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |

| Yield | |
|---|---|
| Mass of SDD Produced (g) | 0.36 |
| Yield (%) | 65 |

Figure 9:
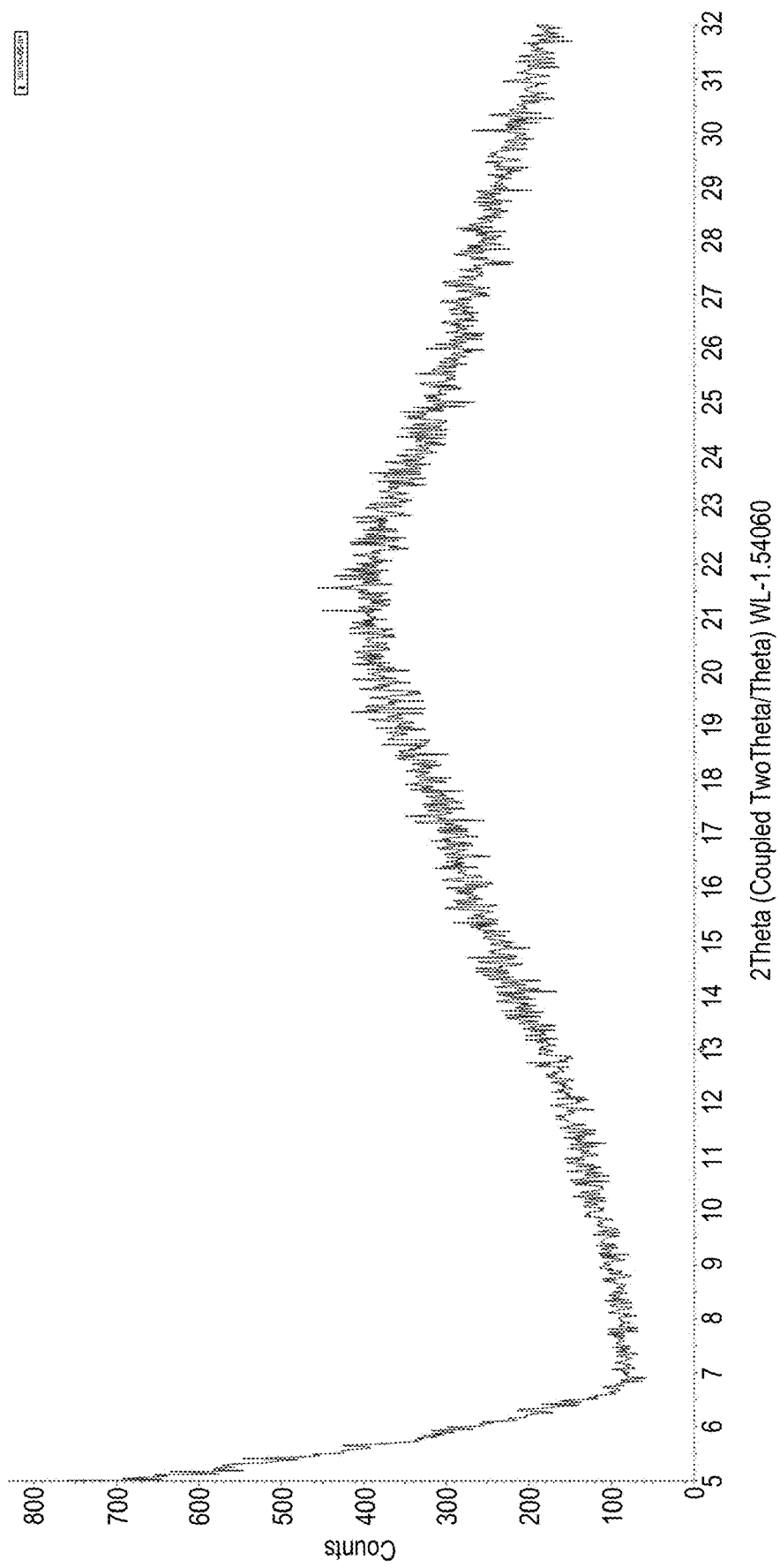
FIG. 9 shows an XRPD for the SDD of Example 3.
Figure 10:
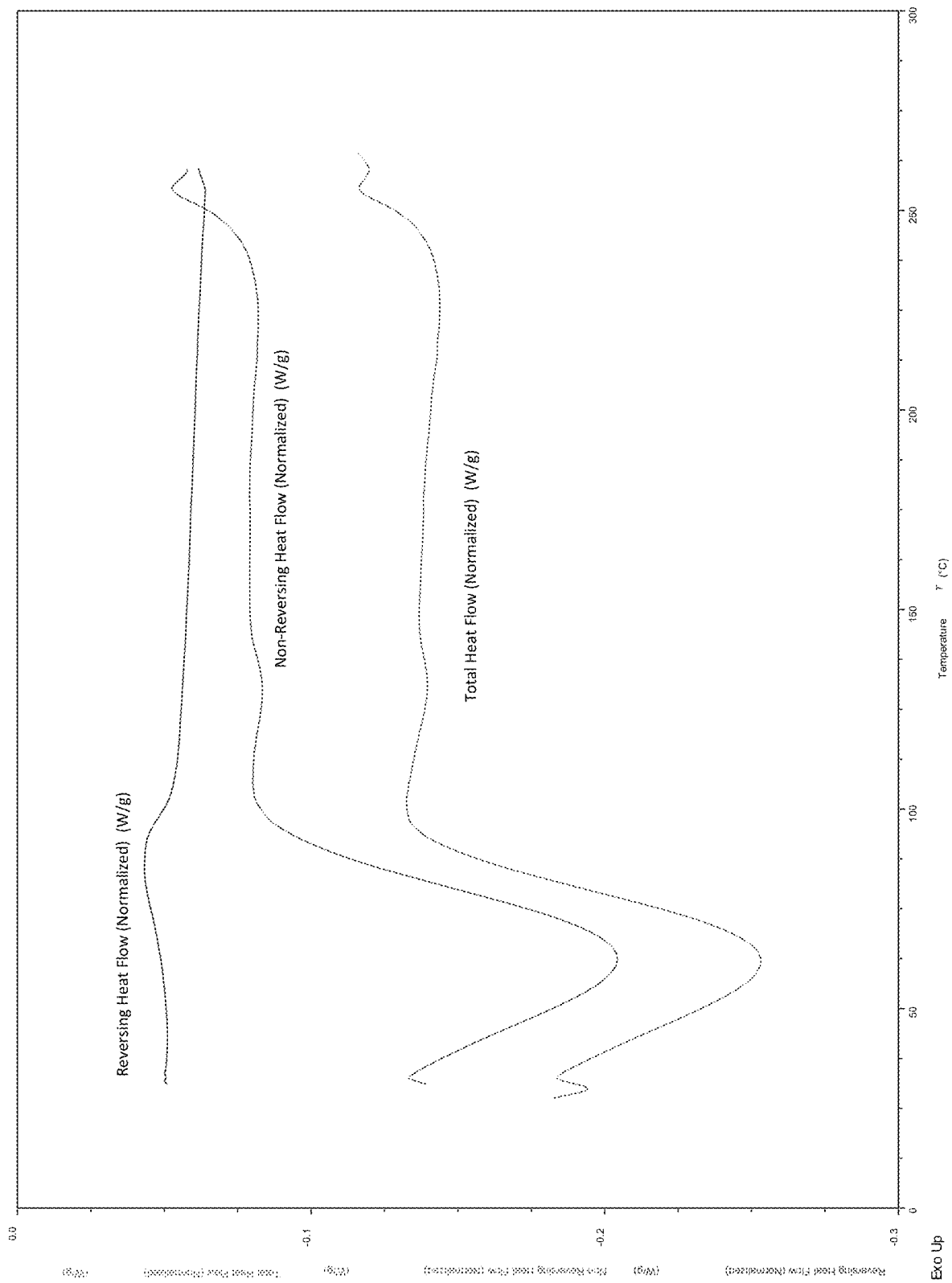
FIG. 10 shows a DSC thermogram for the SDD of Example 3.

The SDD produced was amorphous, as shown by XRPD analysis (FIG. 9), and the absence of an enthalpy of melting when the SDD was examined by DSC (FIG. 10).

Example 4: Spray Drying of 5-MeO-DMT Benzoate Salt with Trehalose

Spray drying 5-MeO-DMT benzoate and trehalose in water produced a 50% wt:wt API to excipient SDD. The spray drying parameters were as below:

| Feed Solution | |
|---|---|
| Sample Reference | 31030-07-01 |
| Trehalose | 0.253 g |
| 5MeO DMT Benzoate | 0.249 g |
| Water (de ionized) | 10.001 g |

| Spray Drying Parameters | |
|---|---|
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |

| Yield | |
|---|---|
| Mass of SDD Produced (g) | 0.222 |
| Yield (%) | 44 |

Figure 11:
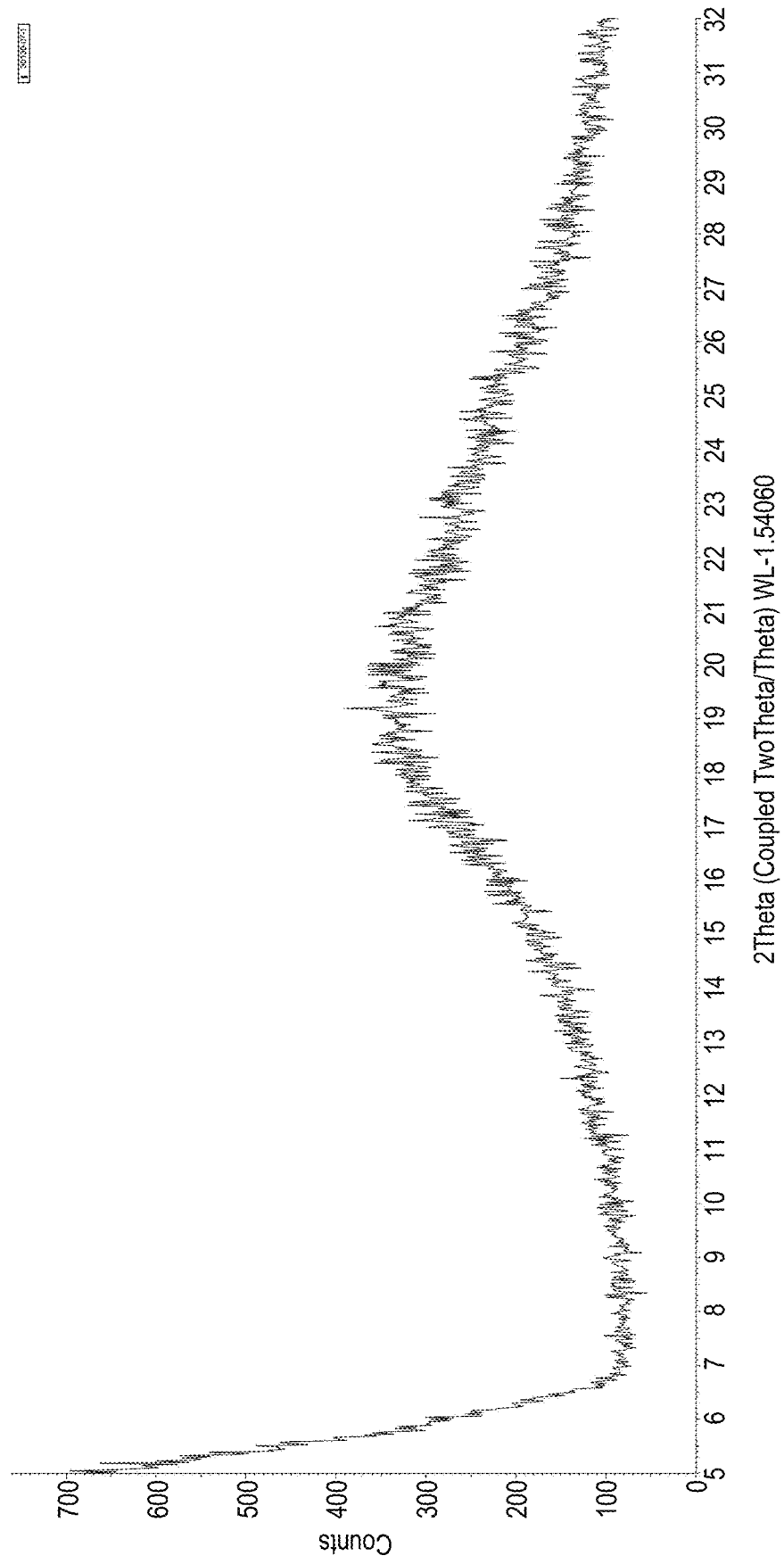
FIG. 11 shows an XRPD for the SDD of Example 4.
Figure 12:
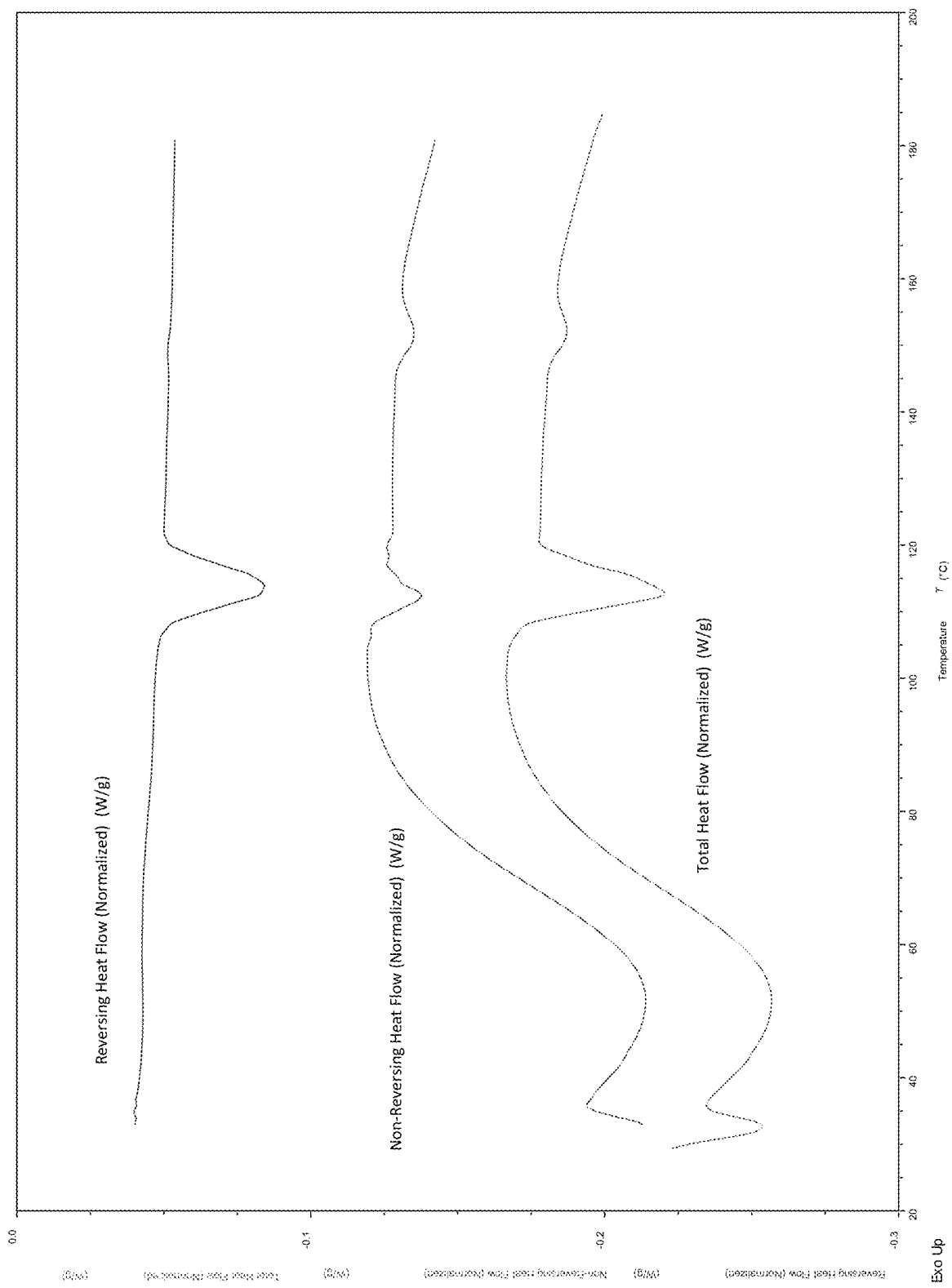
FIG. 12 shows a DSC thermogram for the SDD of Example 4.

The SDD produced was predominantly amorphous by XRPD (FIG. 11), however, there was evidence of partially crystalline material in the XRPD and an enthalpy of melting observed in the DSC (FIG. 12) indicating possible physical instability of the SDD.

Example 5: Spray Drying of 5-MeO-DMT Benzoate Salt with HPMC Mixtures

Spray drying of 5-MeO-DMT benzoate with a mixture of HPMC 2910 in water produced a 50% wt:wt API to excipient SDD. The spray drying parameters were as below:

| Feed Solution | |
|---|---|
| Sample Reference | 30130-08-01 |
| Pharmacoat 606 | 1.19 g |
| Metolose 60SH50 | 1.19 g |
| 5-MeO-DMT Benzoate | 2.38 g |
| Water (deionized) | 95.24 g |

| Spray Drying Parameters | |
|---|---|
| Instrument | Procept |
| Nozzle | Ultrasonic |
| Inlet Flow (m³/min) | 0.7 |
| Inlet Temperature (°C) | 125 |
| Cyclone Gas Pressure (bar) | 0.5 |
| Pump Speed (RPM) | 60 (2 g per minute) |
| Nozzle Power % | 98% |

| Yield | |
|---|---|
| Yield (%) | 34.7 |

The process for producing the feed solution was as follows: the required mass of water was weighed into a 50 mL vial. The required mass of HPMC (Pharmacoat 606) and metolose were added to the water whilst stirring and allowed to fully dissolve. Once dissolved the required mass of API was transferred into the solution and allowed to dissolve. Once dissolved the feed solution was spray dried immediately.

Figure 13:
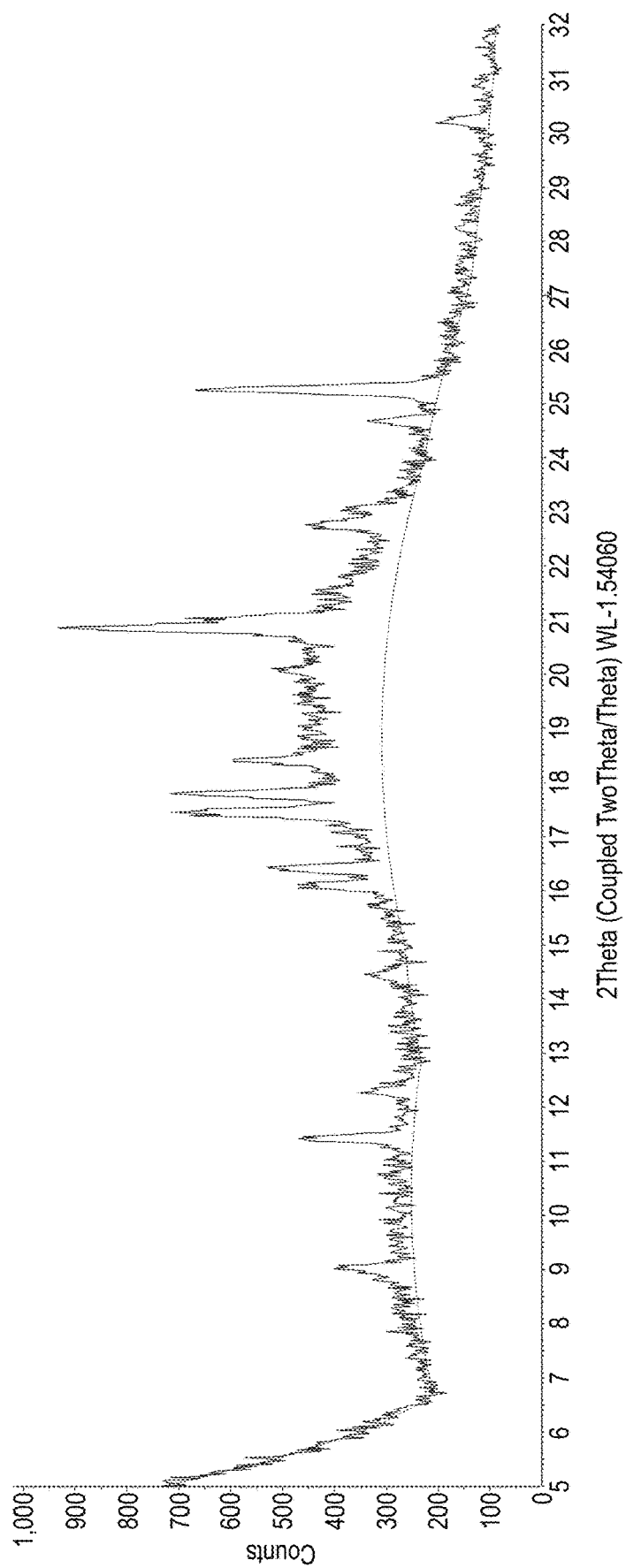
FIG. 13 shows an XRPD for the SDD of Example 5.

The SDD produced was partially crystalline (FIG. 13) and furthermore, at 25% loading of metolose, the yield was quite low.

Example 6: Spray Drying of 5-MeO-DMT Benzoate Salt with HPMC Mixtures

Spray drying of 5-MeO-DMT benzoate with a mixture of HPMC 2910 in water produced a 50% wt:wt API to excipient SDD. The spray drying parameters were as below:

| Feed Solution | |
|---|---|
| Sample Reference | 30130-08-02 |
| Pharmacoat 606 | 1.785 g |
| Metolose 60SH50 | 0.595 g |
| 5-MeO-DMT Benzoate | 2.38 g |
| Water (deionized) | 95.24 g |

| Spray Drying Parameters | |
|---|---|
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |

| Yield | |
|---|---|
| Yield (%) | 62.7 |

Figure 14:
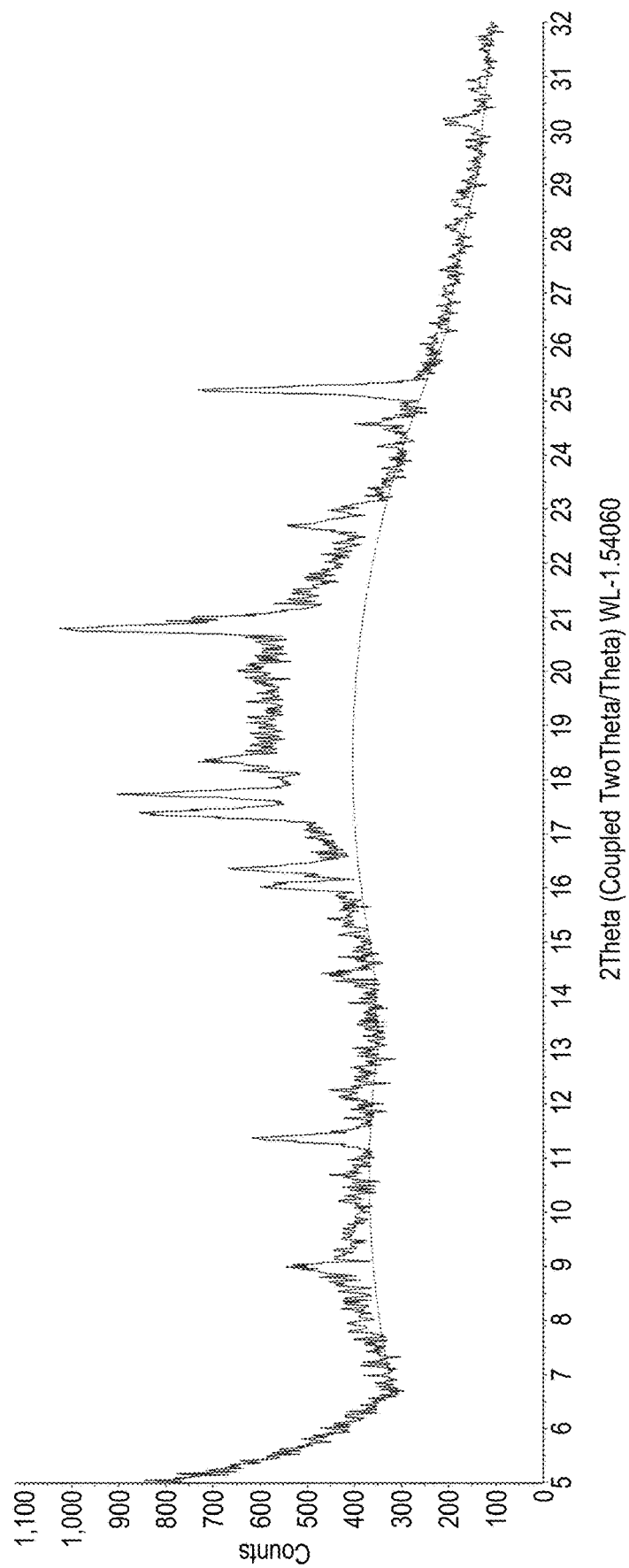
FIG. 14 shows an XRPD for the SDD of Example 6.

The process for producing the feed solution was as described in Example 5. The SDD produced was partially crystalline (FIG. 14), however, surprisingly the use of 12.5% total loading of metolose led to a significant improvement in yield over the SDD produced in Example 5 (25% metolose).

Figure 15:
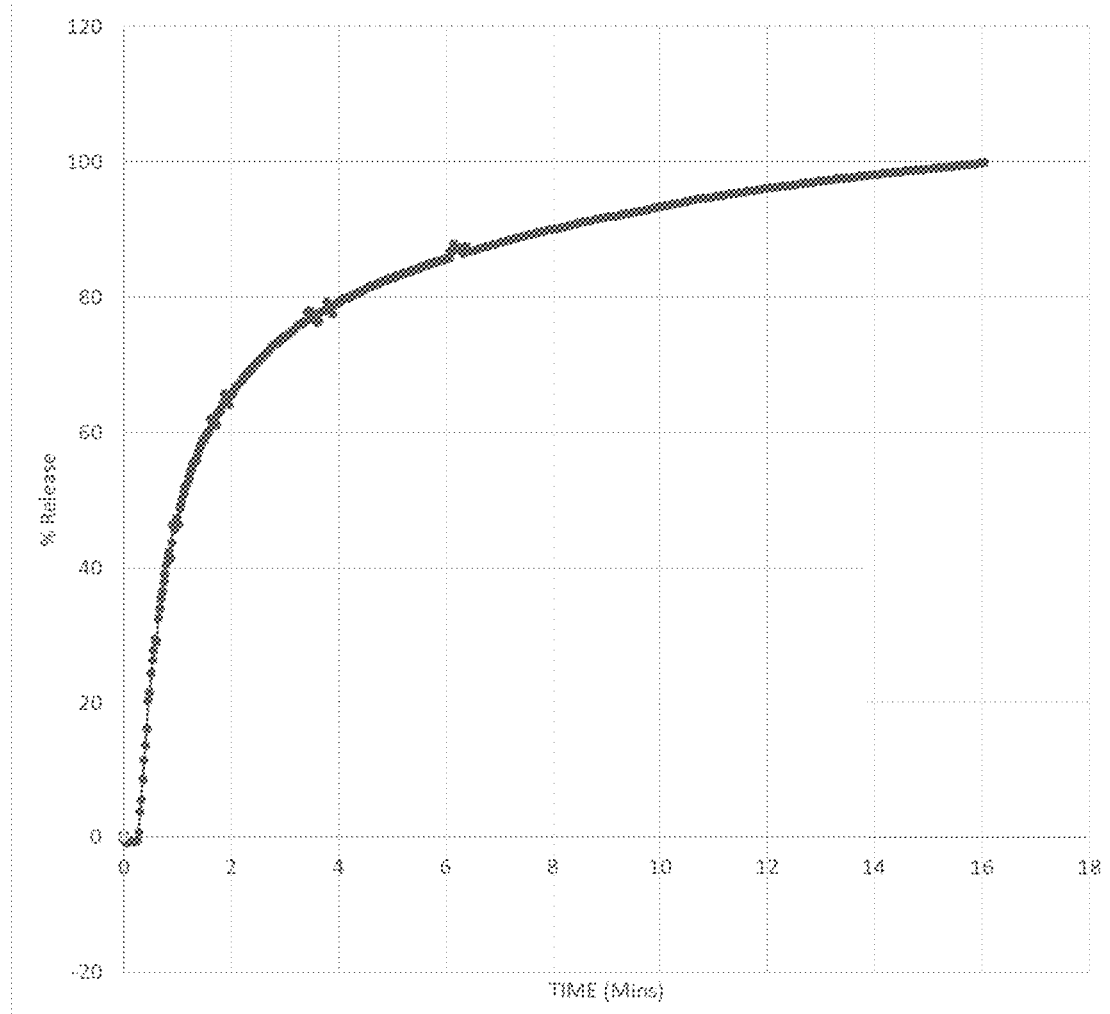
FIG. 15 shows the dissolution profile of the SDD of Example 6.

The dissolution profile for the SDD produced can be seen in FIG. 15, this shows that ~80% release has occurred by ~4 minutes.

Example 7: Spray Drying of 5-MeO-DMT Benzoate Salt with HPMCAS

Spray drying of 5-MeO-DMT benzoate with hydroxypropyl methylcellulose acetate succinate (HPMCAS) M produced a 50% wt:wt API to excipient SDD. HPMCAS is produced in three substitution grades: L, M and H. The spray drying parameters were as below:

| Feed Solution | |
|---|---|
| Sample Reference | 30120-08-03 |
| HPMCAS M | 2.38 g |
| 5-MeO-DMT Benzoate | 2.38 g |
| Water (deionized) | 47.62 g |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 96% |
| Yield | |
| Yield (%) | 44.7 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by API and the vial was then stirred until the API dissolved. Once dissolved the feed solution was spray dried immediately.

Figure 16:
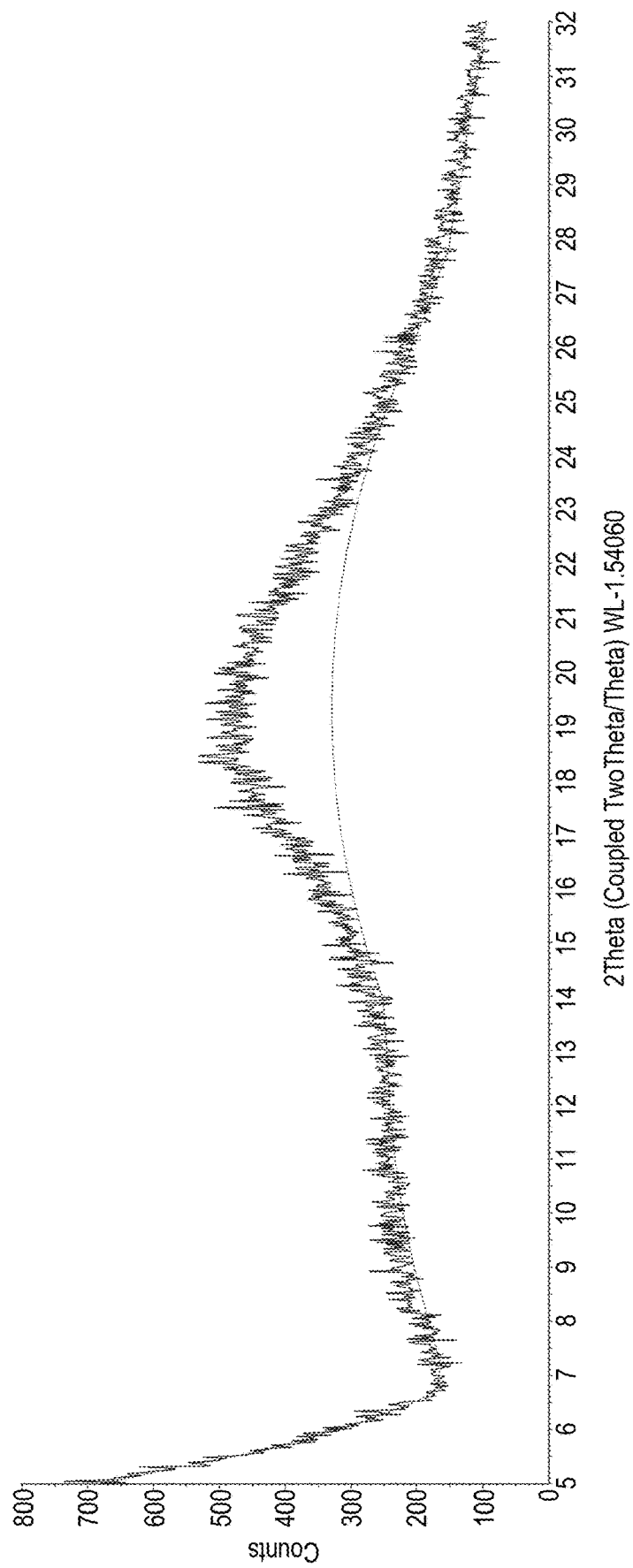
FIG. 16 shows an XRPD for the SDD of Example 7.

The SDD produced was state-stable and amorphous (FIG. 16).

Example 8: Spray Drying of 5-MeO-DMT Benzoate Salt with HPMCAS/Metolose

Spray drying of 5-MeO-DMT benzoate with HPMCAS M and Metolose 60SH50 in water produced a 50% wt:wt API to excipient SDD. The spray drying parameters were as below:

| Feed Solution | |
|---|---|
| HPMCAS M | 1.19 g |
| Metolose 60SH50 | 1.19 g |
| 5-MeO-DMT Benzoate | 2.38 g |
| Water (deionized) | 47.62 g |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Nozzle Power % | 96% |
| Yield | |
| Yield (%) | 29.2 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by HPMC, the vial was stirred over night to dissolve. Once dissolved the API was added and stirred, once dissolved the feed solution was spray dried immediately.

Figure 17:
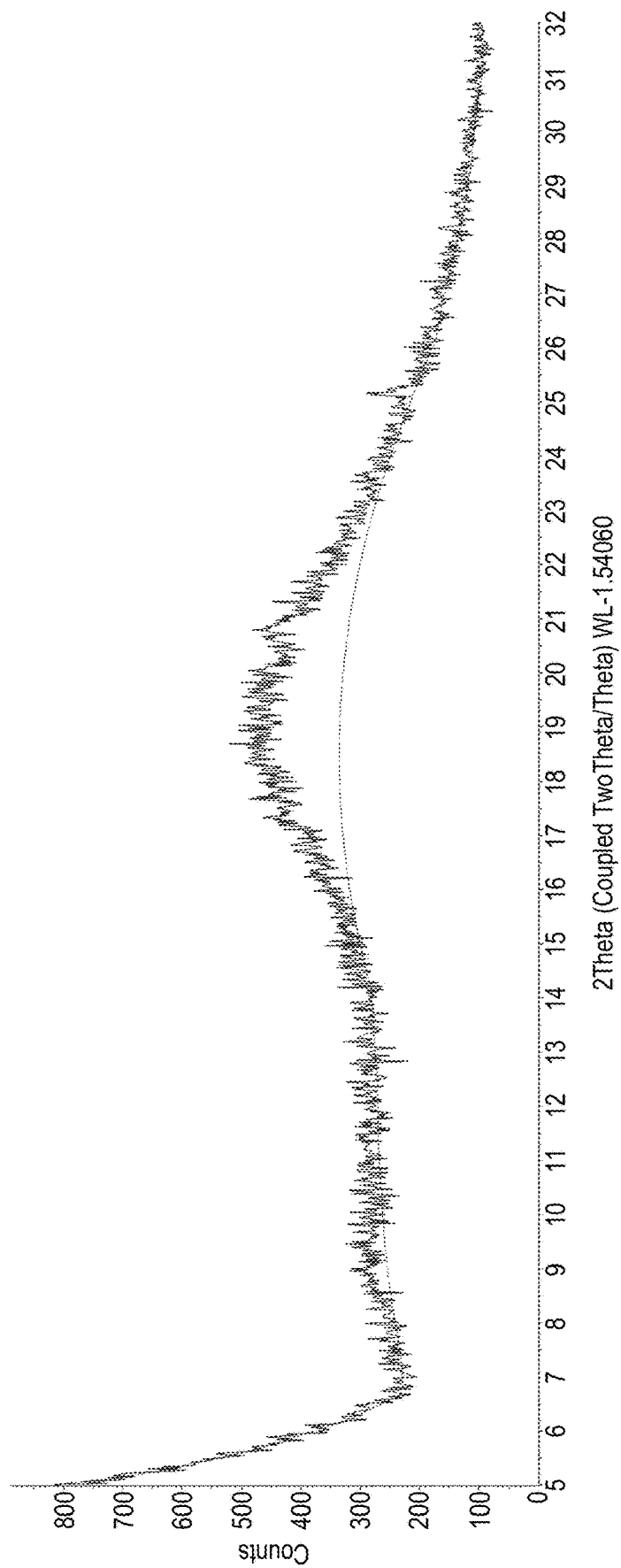
FIG. 17 shows an XRPD for the SDD of Example 8.

The SDD produced was predominantly amorphous (FIG. 17), however, there was some difficulty in spray drying viscous solutions containing HPMC-AS.

Example 9: Spray Drying of 5-MeO-DMT Benzoate Salt with HPMCAS/Metolose

Spray drying of 5-MeO-DMT benzoate with HPMCAS M and Metolose 60SH50 in water produced a 50% wt:wt API to excipient SDD. The spray drying parameters were as below:

| Feed Solution | |
|---|---|
| HPMCAS M | 1.785 g |
| Metolose 60SH50 | 1.595 g |
| 5-MeO—DMT benzoate | 2.38 g |
| Water (deionized) | 47.62 gg |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Nozzle Power % | 96% |
| Yield | |
| Yield (%) | 27.2 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by HPMC, the vial was stirred over night to dissolve. Once dissolved the API was added and stirred, once dissolved the feed solution was spray dried immediately.

Figure 18:
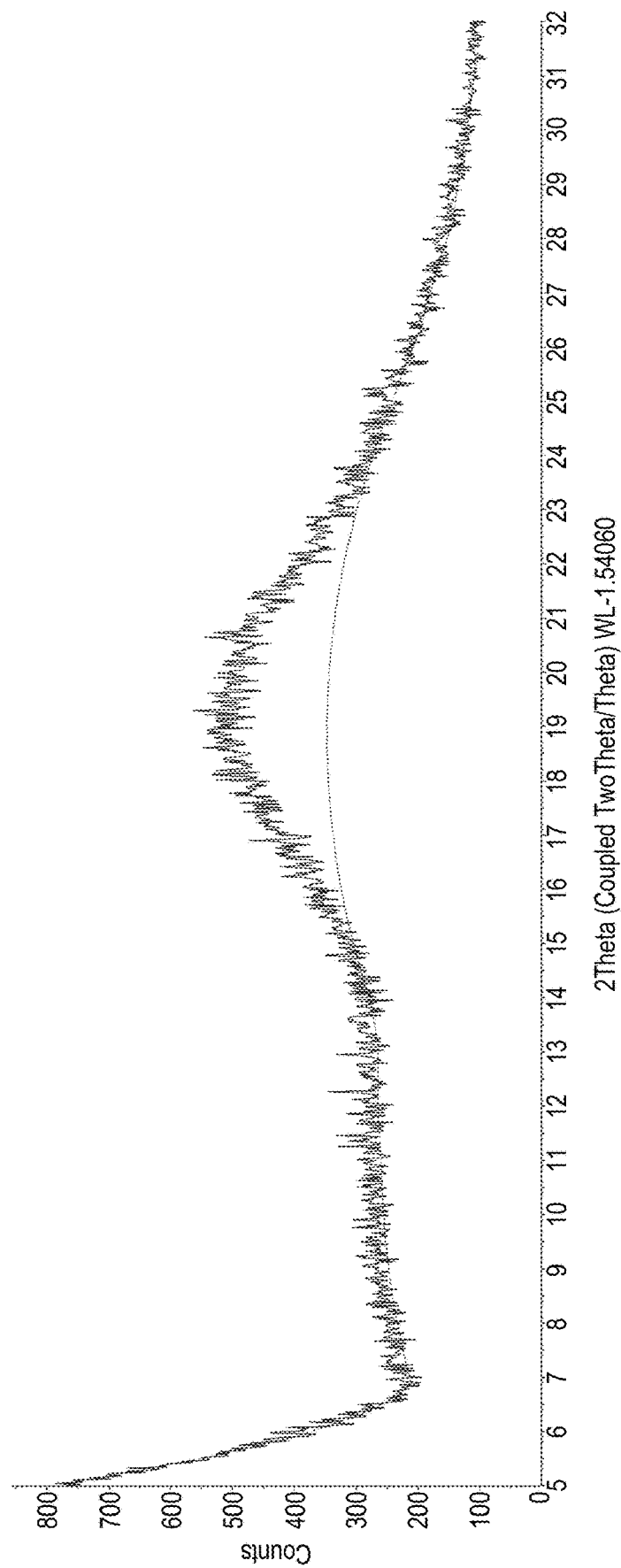
FIG. 18 shows an XRPD for the SDD of Example 9.

The SDD produced was predominantly amorphous (FIG. 18), however, there was some difficulty in spray drying viscous solutions containing HPMC-AS.

Example 10: Spray Drying of 5-MeO-DMT Benzoate Salt with HPMC Mixtures

Spray drying of 5-MeO-DMT benzoate with a mixture of HPMC 2910 in water produced a 10% wt:wt API to excipient SDD. The spray drying parameters were as below:

| SDD Composition | |
|---|---|
| Sample Reference | 3815-02-01 |
| Pharmacoat 606 | 67.5% |
| Metolose 60SH50 | 22.5% |
| 5-MeO—DMT Benzoate | 10% |
| Spray Drying Parameters | |
| Instrument | Procept |
| Nozzle | Ultrasonic |
| Inlet Flow (m³/min) | 0.7 |
| Inlet Temperature (° C.) | 125 |

| -continued | |
|---|---|
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 58% |

The process for spray drying the feed solution was as follows: the required mass of water was weighed into a 50 mL vial. The required mass of HPMC and Metolose were added to the water whilst stirring and allowed to fully dissolve. Once dissolved the required mass of API was transferred into the solution and allowed to dissolve. Once dissolved the feed solution was spray dried immediately.

Figure 19:
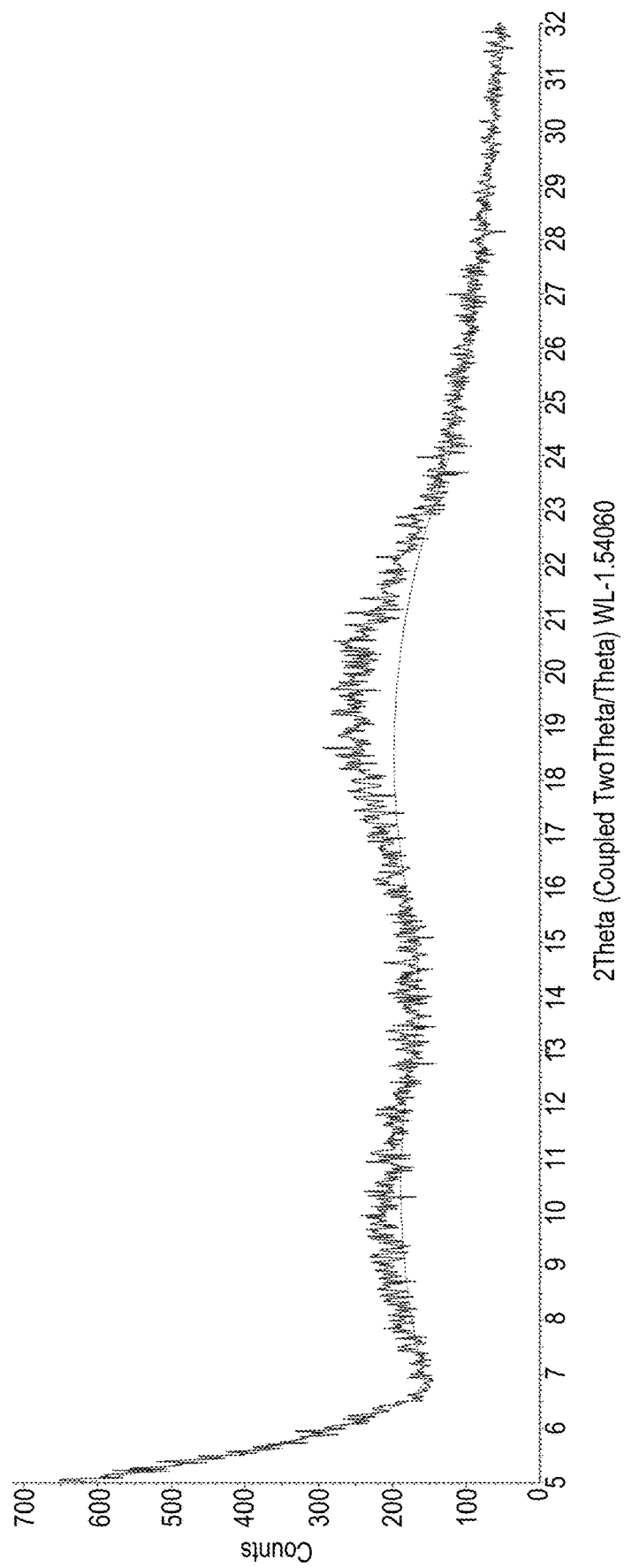
FIG. 19 shows an XRPD for the SDD of Example 10.
Figure 20:
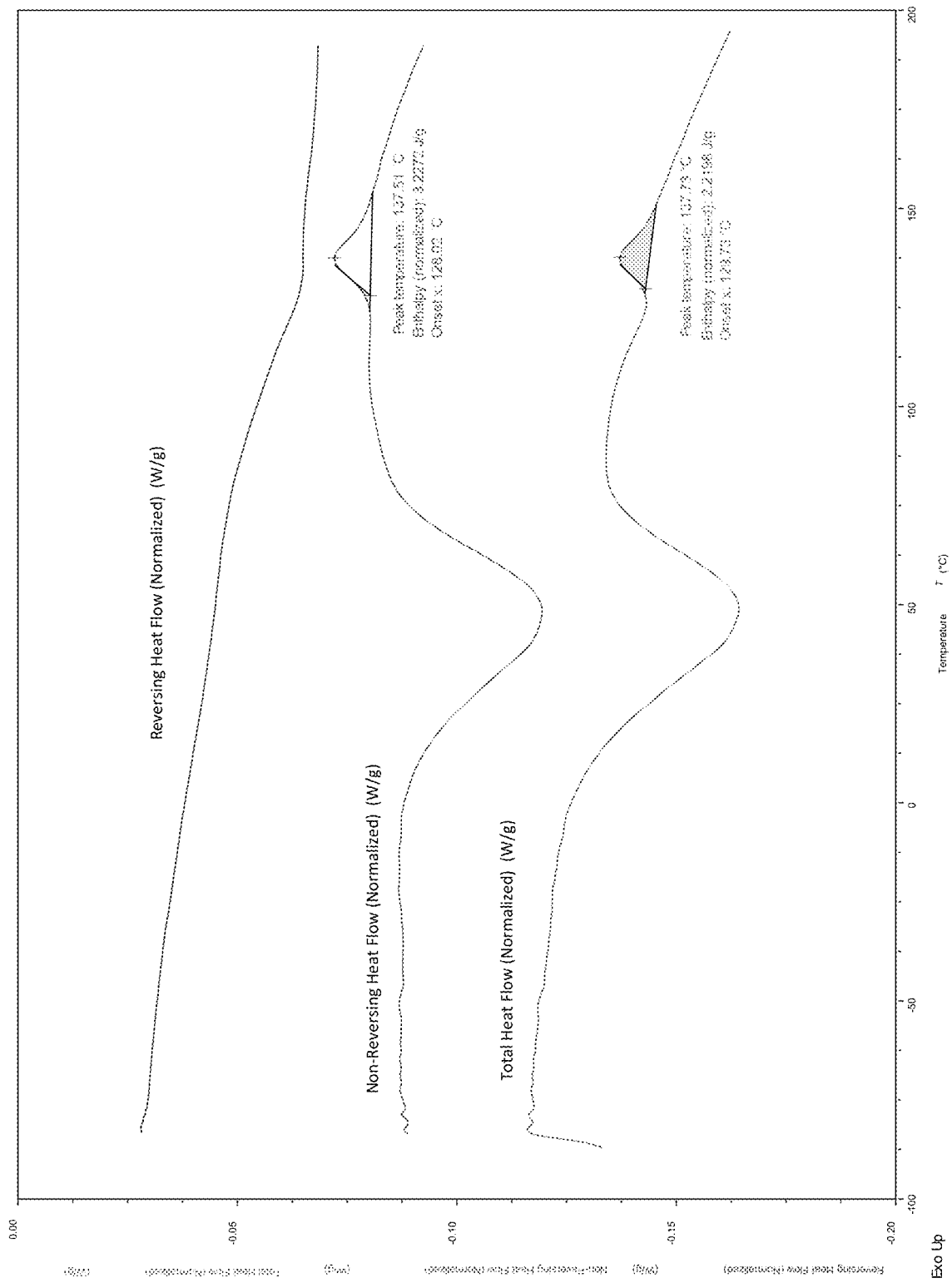
FIG. 20 shows a DSC thermogram for the SDD of Example 10.
Figure 21:
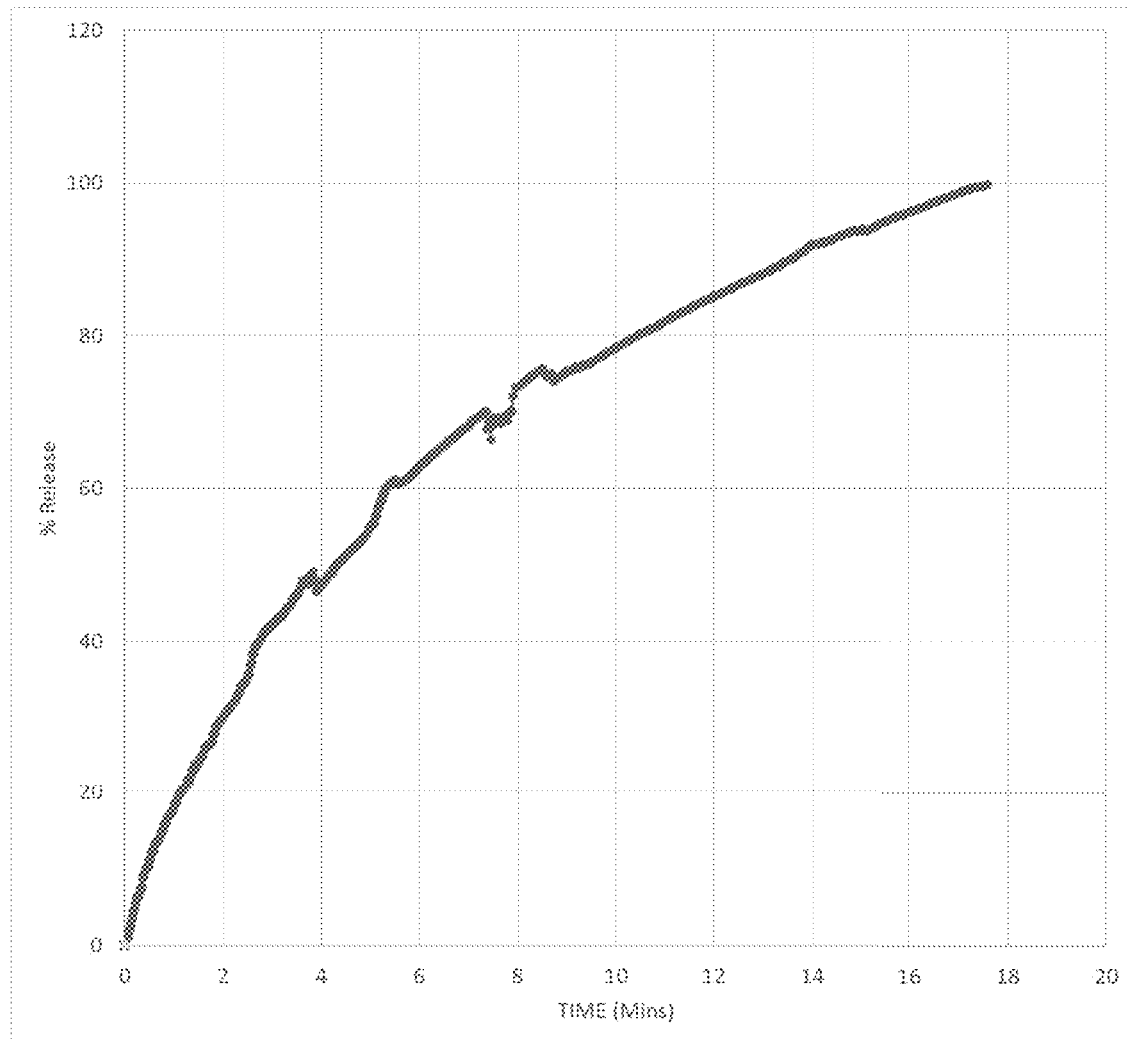
FIG. 21 shows the dissolution profile for the SDD of Example 10.

The SDD produced was stable and amorphous by XRPD (FIG. 19) and DSC (FIG. 20). The dissolution profile of the SDD (FIG. 21) shows that ~80% release has occurred by ~10 minutes, compared with the ~4 minutes for the SDD of Example 6.

Example 11: Spray Drying of 5-MeO-DMT Benzoate Salt with HPMC Mixtures

Spray drying of 5-MeO-DMT benzoate with a mixture of HPMC 2910 in water produced a 30% wt:wt API to excipient SDD. The spray drying parameters were as below:

| SDD Composition | |
|---|---|
| Sample Reference | 3815-02-02 |
| Pharmacoat 606 | 52.5% |
| Metolose 60SH50 | 17.5% |
| 5-MeO—DMT Benzoate | 30% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 60% |

The process for spray drying the feed solution was as follows: the required mass of water was weighed into a 50 mL vial. The required mass of HPMC and metolose were added to the water whilst stirring and allowed to fully dissolve. Once dissolved the required mass of API was transferred into the solution and allowed to dissolve. Once dissolved the feed solution was spray dried immediately.

Figure 22:
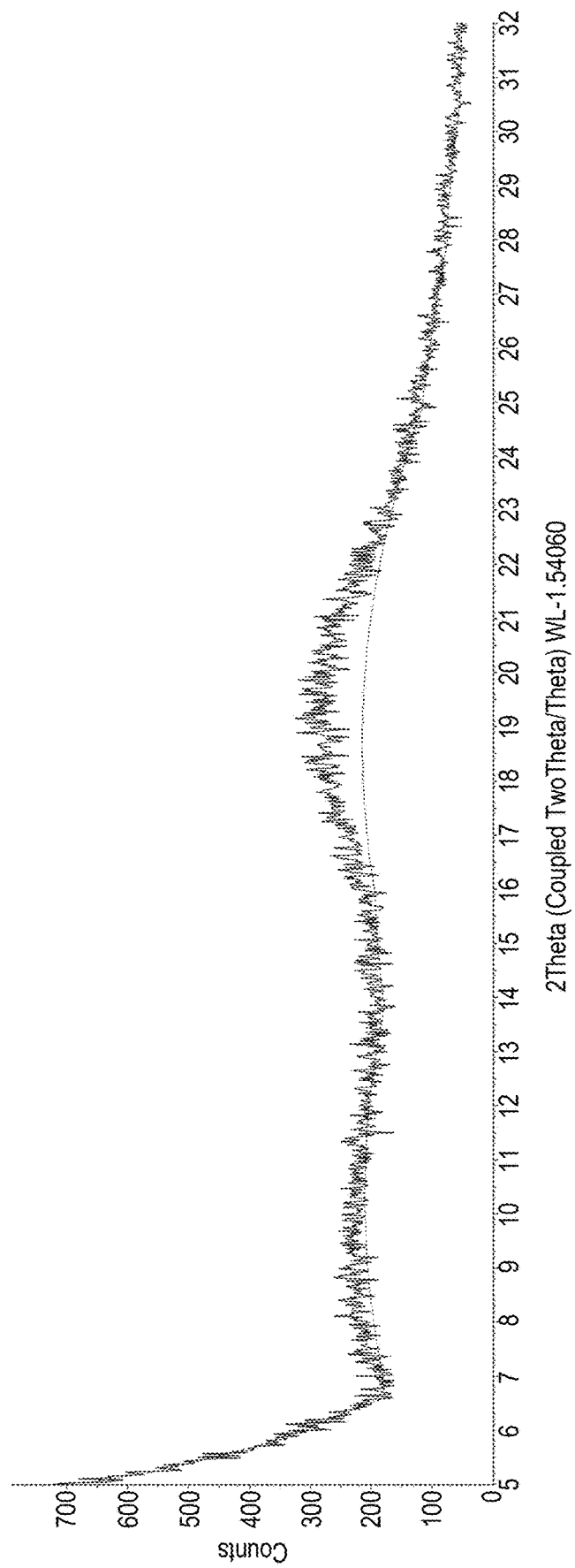
FIG. 22 shows an XRPD for the SDD of Example 11.
Figure 23:
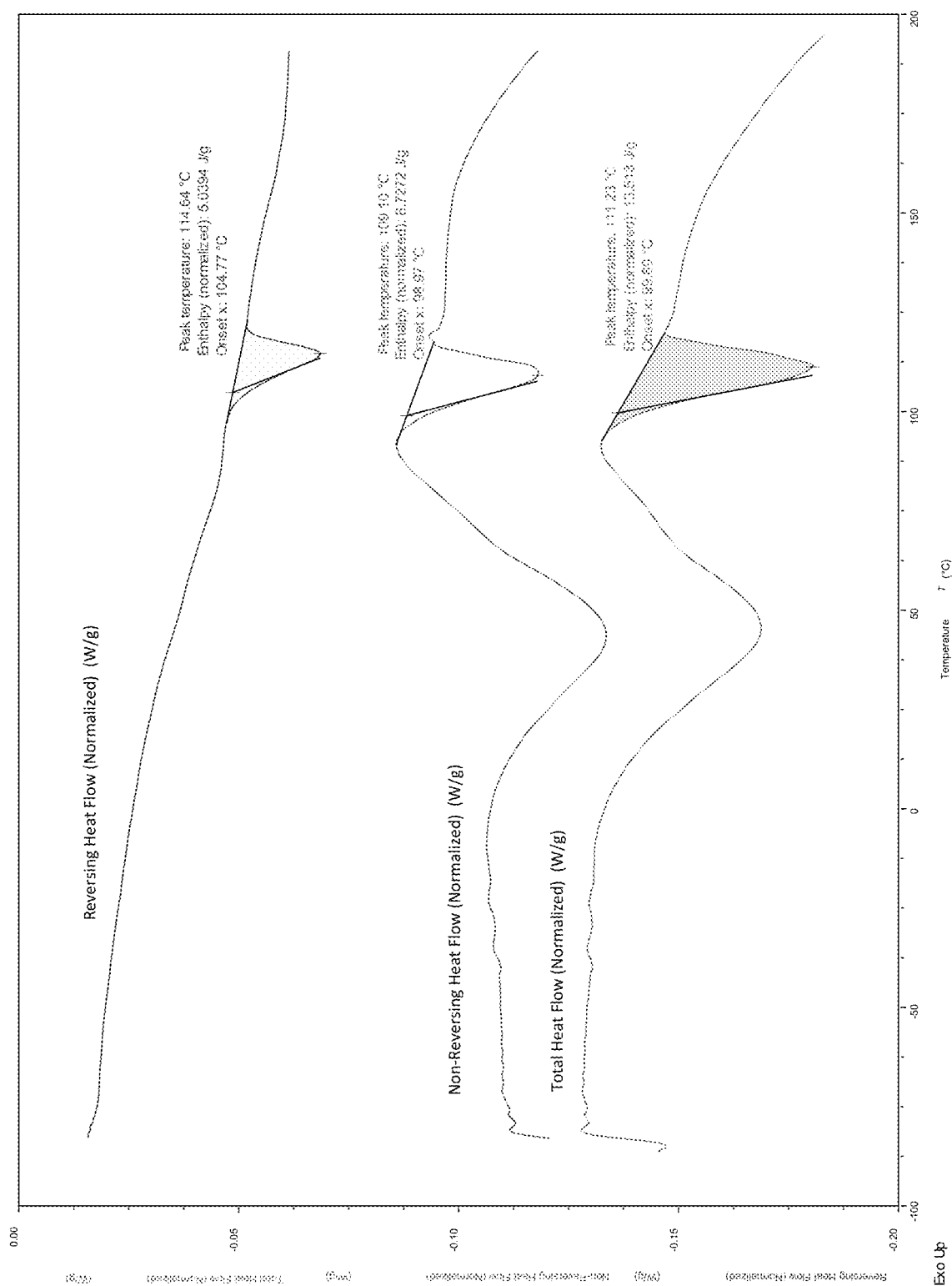
FIG. 23 shows a DSC thermogram for the SDD of Example 11.
Figure 24:
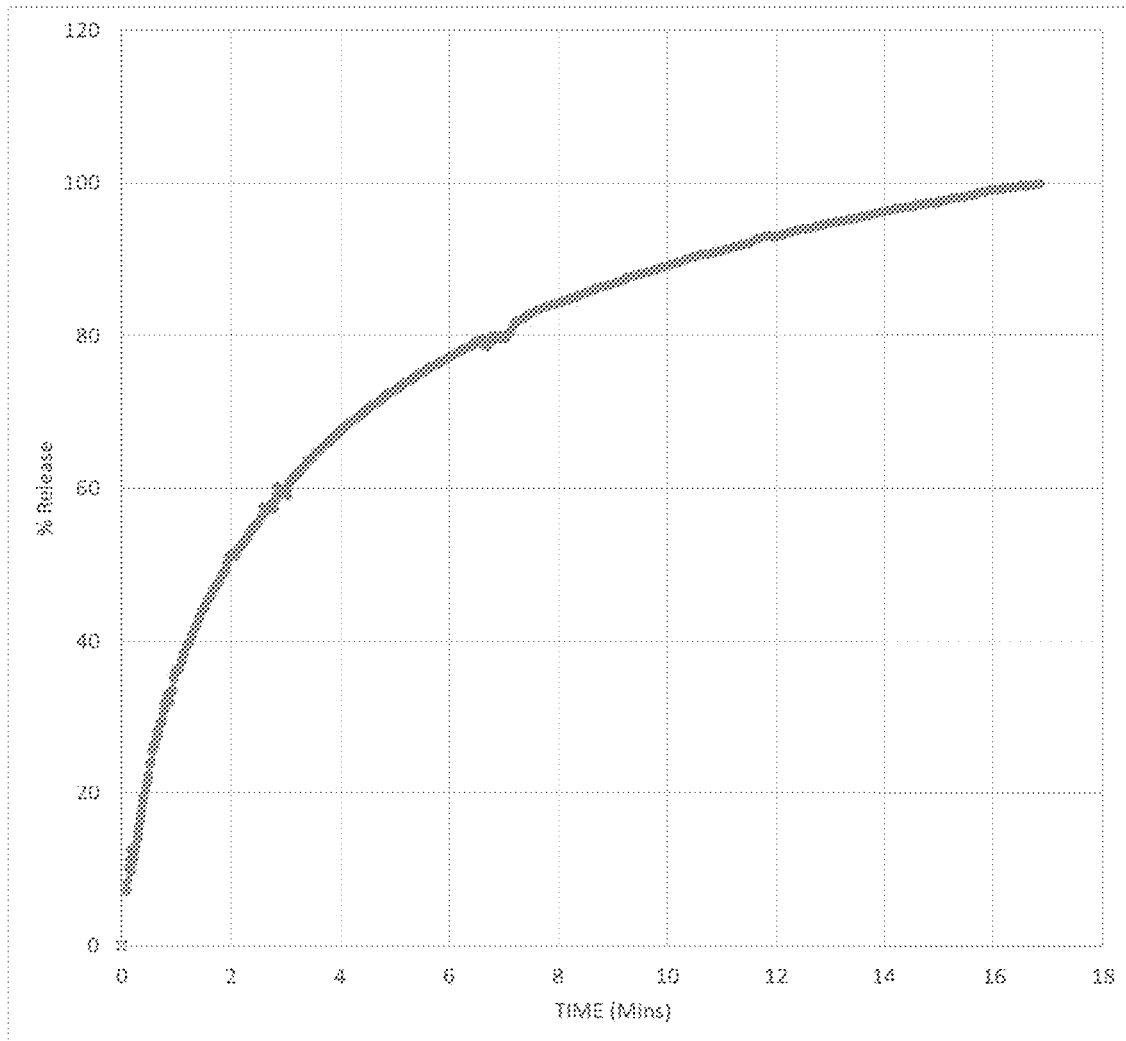
FIG. 24 shows the dissolution profile for the SDD of Example 11.

The SDD produced was stable and amorphous by XRPD (FIG. 22) and DSC (FIG. 23). The dissolution profile of the SDD (FIG. 24) shows that ~80% release has occurred by ~6.5 minutes, compared with ~4 minutes for the SDD of Example 6 and ~10 minutes for the SDD of Example 10.

Example 12: Spray Drying of 5-MeO-DMT Benzoate Salt with HPMC Mixtures

Spray drying of 5-MeO-DMT benzoate salt with a mixture of HPMC 2910 in water produced a 50% wt:wt API to excipient SDD. The spray drying parameters were as below:

| SDD Composition | |
|---|---|
| Example Reference | 3815-02-02 |
| Pharmacoat 606 | 37.5% |
| Metolose 60SH50 | 12.5% |
| 5-MeO—DMT Benzoate | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 52% |

The spray drying process was as follows: the required mass of water was weighed into a 50 mL vial. The required mass of HPMC and metolose were added to the water whilst stirring and allowed to fully dissolve. Once dissolved the required mass of API was transferred into the solution and allowed to dissolve. Once dissolved the feed solution was spray dried immediately.

Figure 25:
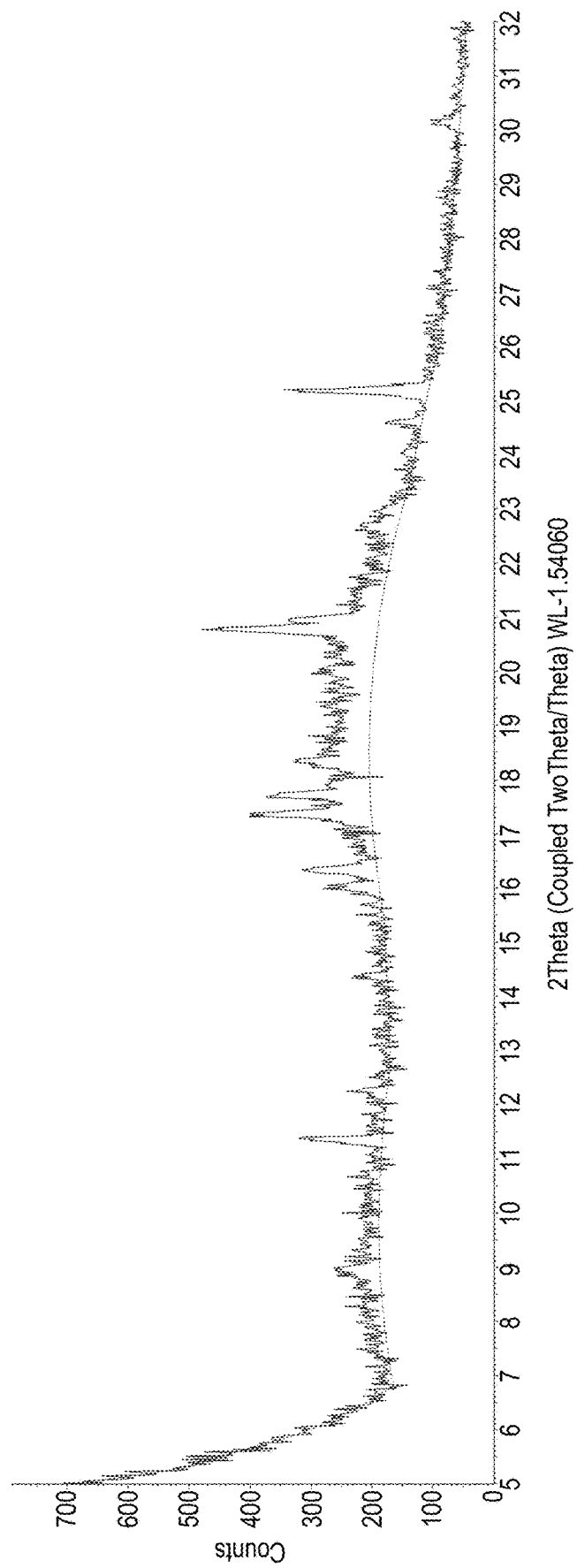
FIG. 25 shows an XRPD for the SDD of Example 12.
Figure 26:
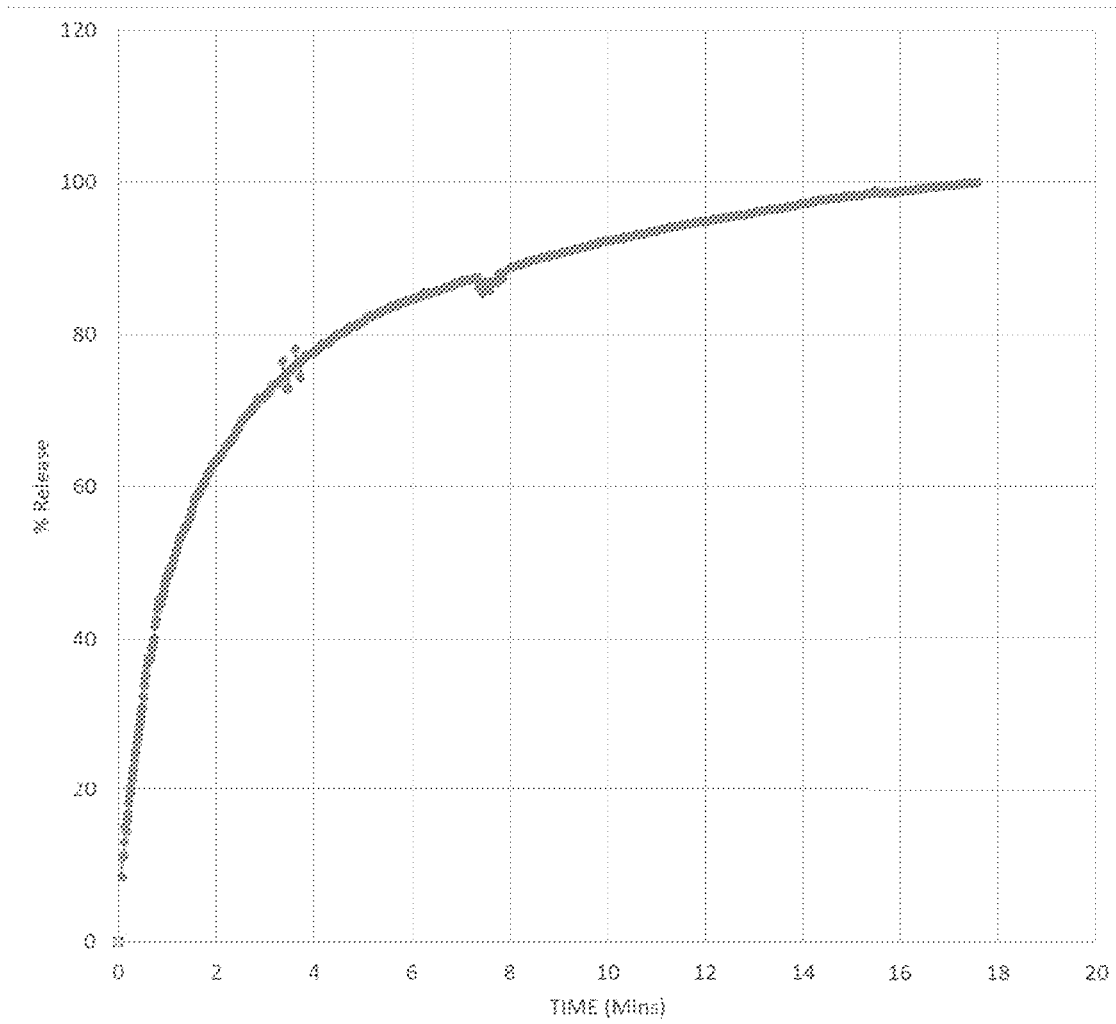
FIG. 26 shows the dissolution profile for the SDD of Example 12.

The SDD produced was partially crystalline (FIG. 25) with a dissolution profile (FIG. 26) that shows that ~80% release has occurred by ~4.5 minutes, compared with ~4 minutes for the SDD of Example 6, ~10 minutes for the SDD of Example 10 and ~6.5 minutes for the SDD of Example 11.

Figure 27:
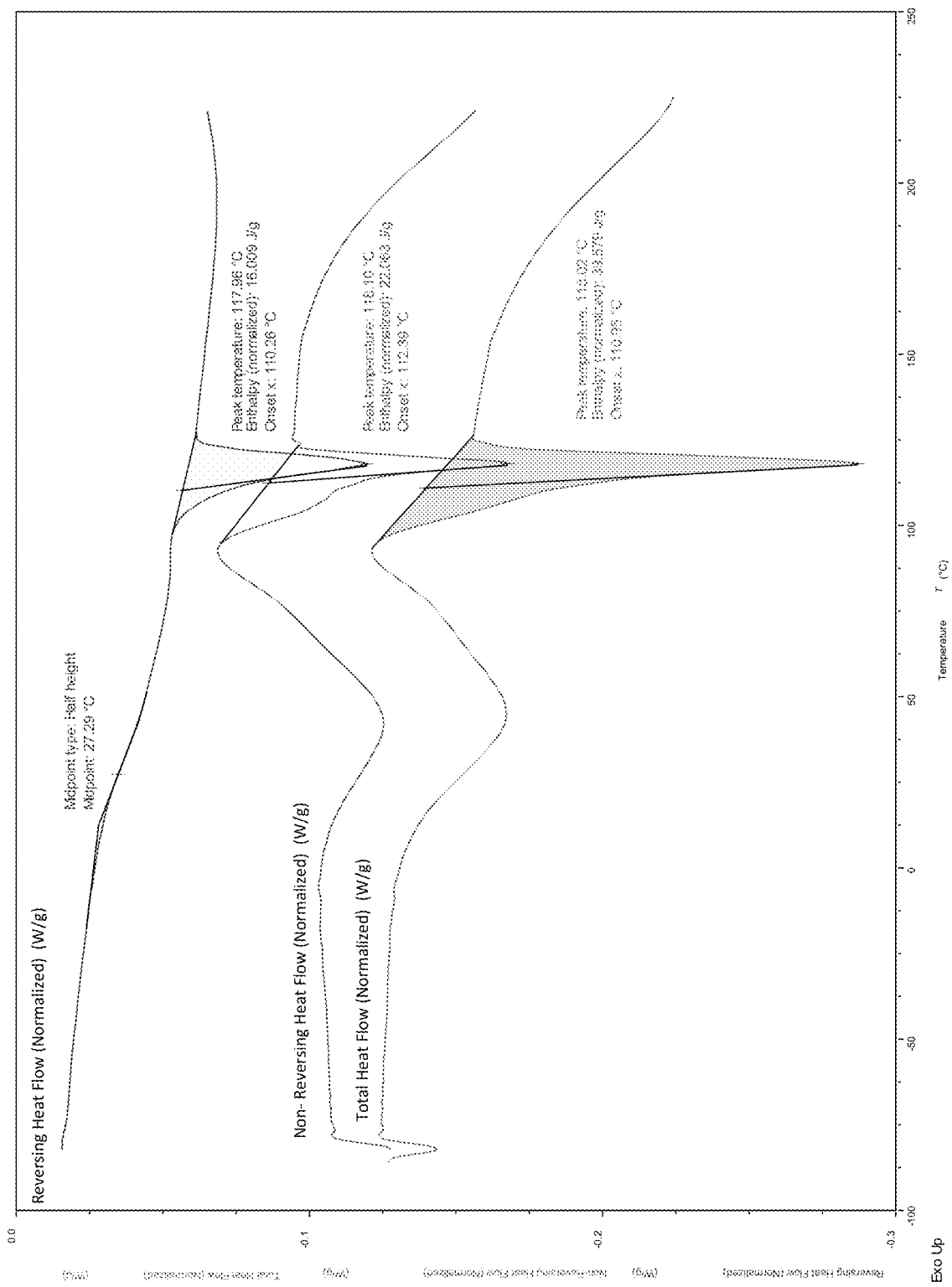
FIG. 27 shows a DSC thermogram for the SDD of Example 12.

The DSC thermogram for the SDD (FIG. 27) shows a small peak at ~140° C. indicating the presence of crystalline API. Such a peak is not seen in the equivalent HBr or HCl salt formulations.

Example 13: Spray Drying of 5-MeO-DMT Benzoate Salt with HPMC Mixtures

Spray drying of 5-MeO-DMT benzoate salt with a mixture of HPMC 2910 and sorbitol in water produced a 10% wt:wt API to excipient SDD. The spray drying parameters were as below:

| SDD Composition | |
|---|---|
| Sample Reference | 3815-02-04 |
| Pharmacoat 606 | 65.25% |
| Metolose 60SH50 | 21.75% |
| Sorbitol M | 3% |
| 5-MeO—DMT Benzoate | 10% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 61% |

The spray drying process was as follows: the required mass of water was weighed into a 50 mL vial. The required mass of HPMC and metolose were added to the water whilst stirring and allowed to fully dissolve. Once dissolved the required mass of API and sorbitol were transferred into the solution and allowed to dissolve. Once dissolved the feed solution was spray dried immediately.

Figure 28:
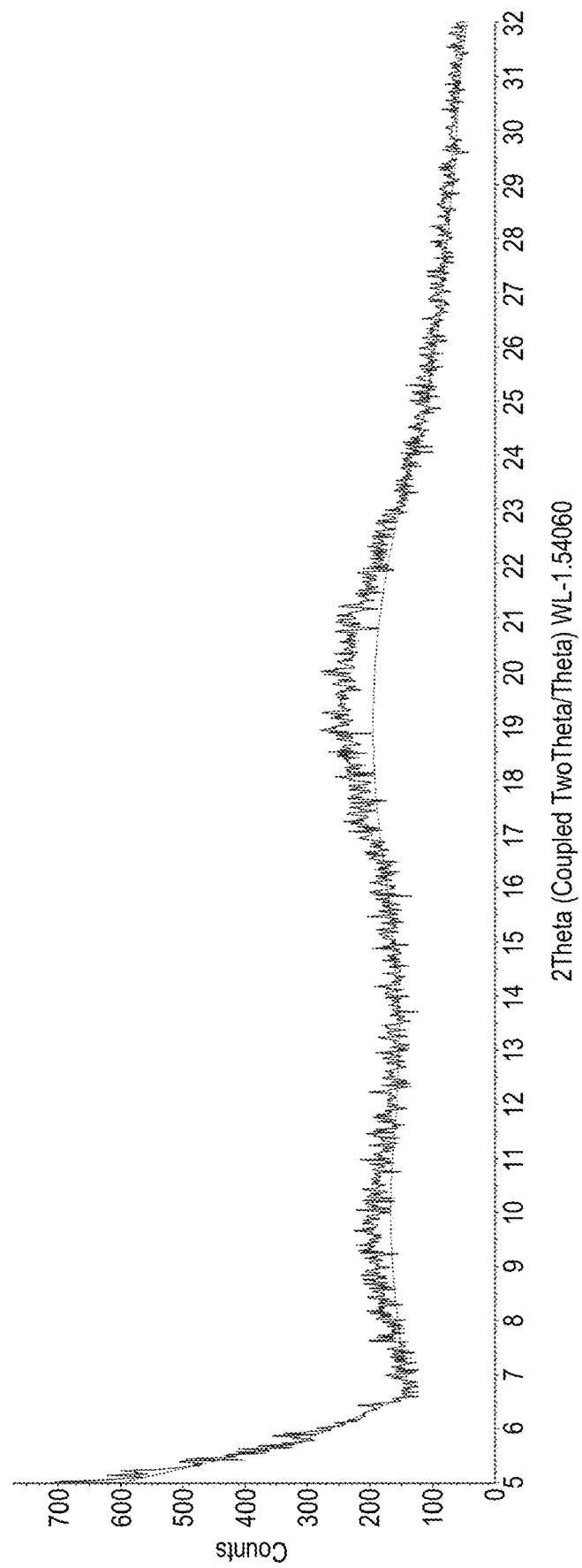
FIG. 28 shows an XRPD for the SDD of Example 13.
Figure 29:
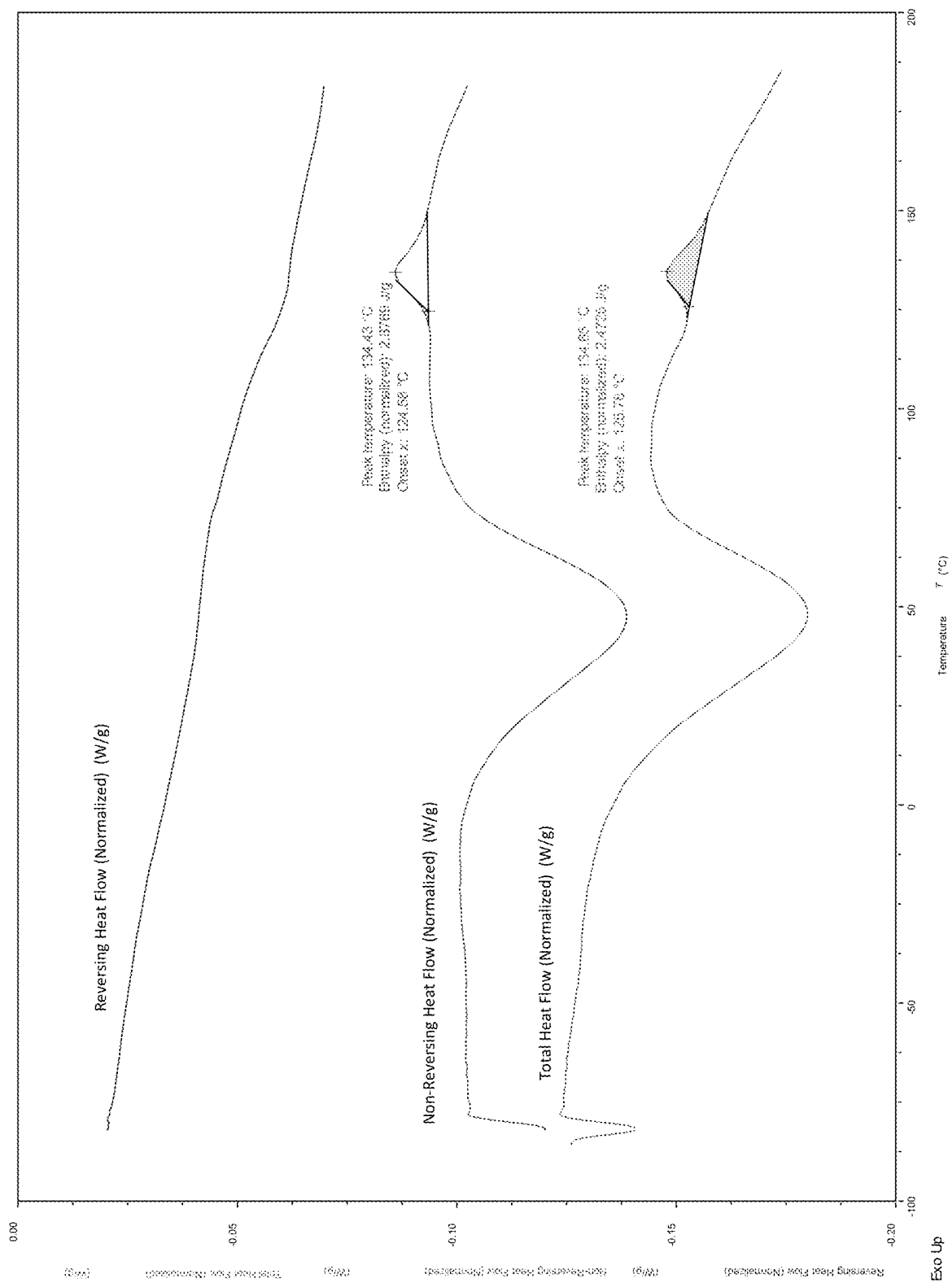
FIG. 29 shows a DSC thermogram for the SDD of Example 13.
Figure 30:
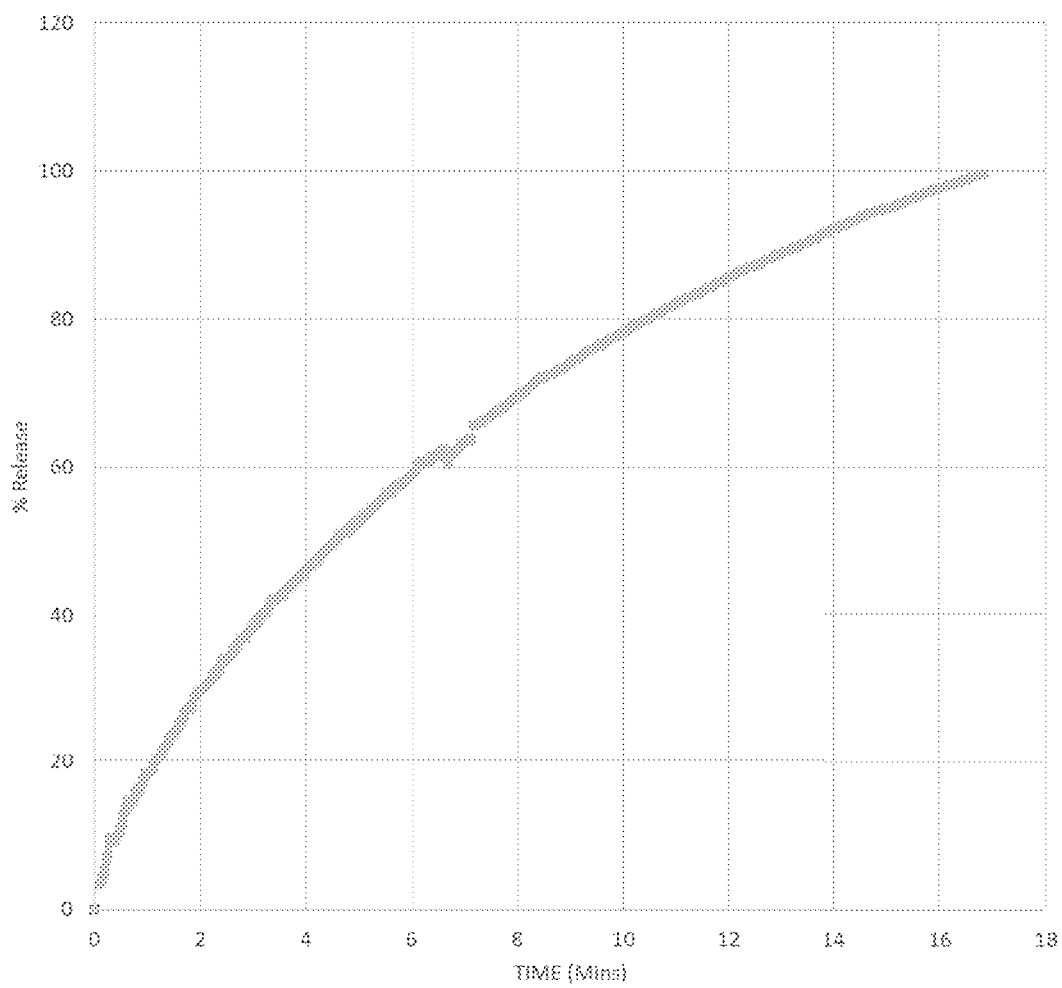
FIG. 30 shows the dissolution profile for the SDD of Example 13.

The SDD produced was stable and amorphous, as shown in FIGS. 28 and 29, and the yield had improved over that which was observed for the SDD of Example 12. The dissolution profile (FIG. 30) shows that ~80% release has occurred by ~10 minutes compared with ~4 minutes for the SDD of Example 6, ~10 minutes for the SDD of Example 10, ~6.5 minutes for the SDD of Example 11 and ~4.5 minutes for Example 12.

Example 14: Spray Drying of 5-MeO-DMT Benzoate Salt with HPMC Mixtures

Spray drying of 5-MeO-DMT benzoate salt with a mixture of HPMC 2910 and sorbitol in water produced a 30% wt:wt API to excipient SDD. The spray drying parameters were as below:

| SDD Composition | |
| --- | --- |
| Sample Reference | 3815-02-05 |
| Pharmacoat 606 | 50.25% |
| Metolose 60SH50 | 16.75% |
| Sorbitol M | 3% |
| 5-MeO—DMT Benzoate | 30% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 3.1 |
| Yield | |
| Yield (%) | 78% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

Figure 31:
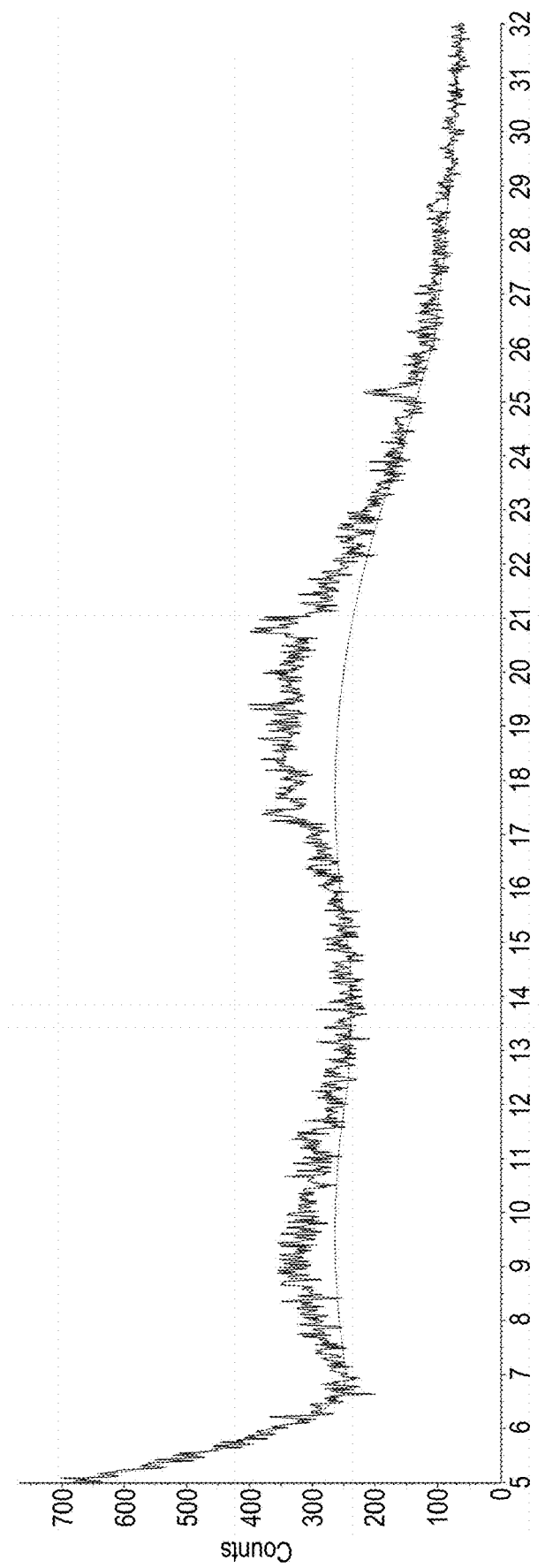
FIG. 31 shows an XRPD of the SDD of Example 14.
Figure 32:
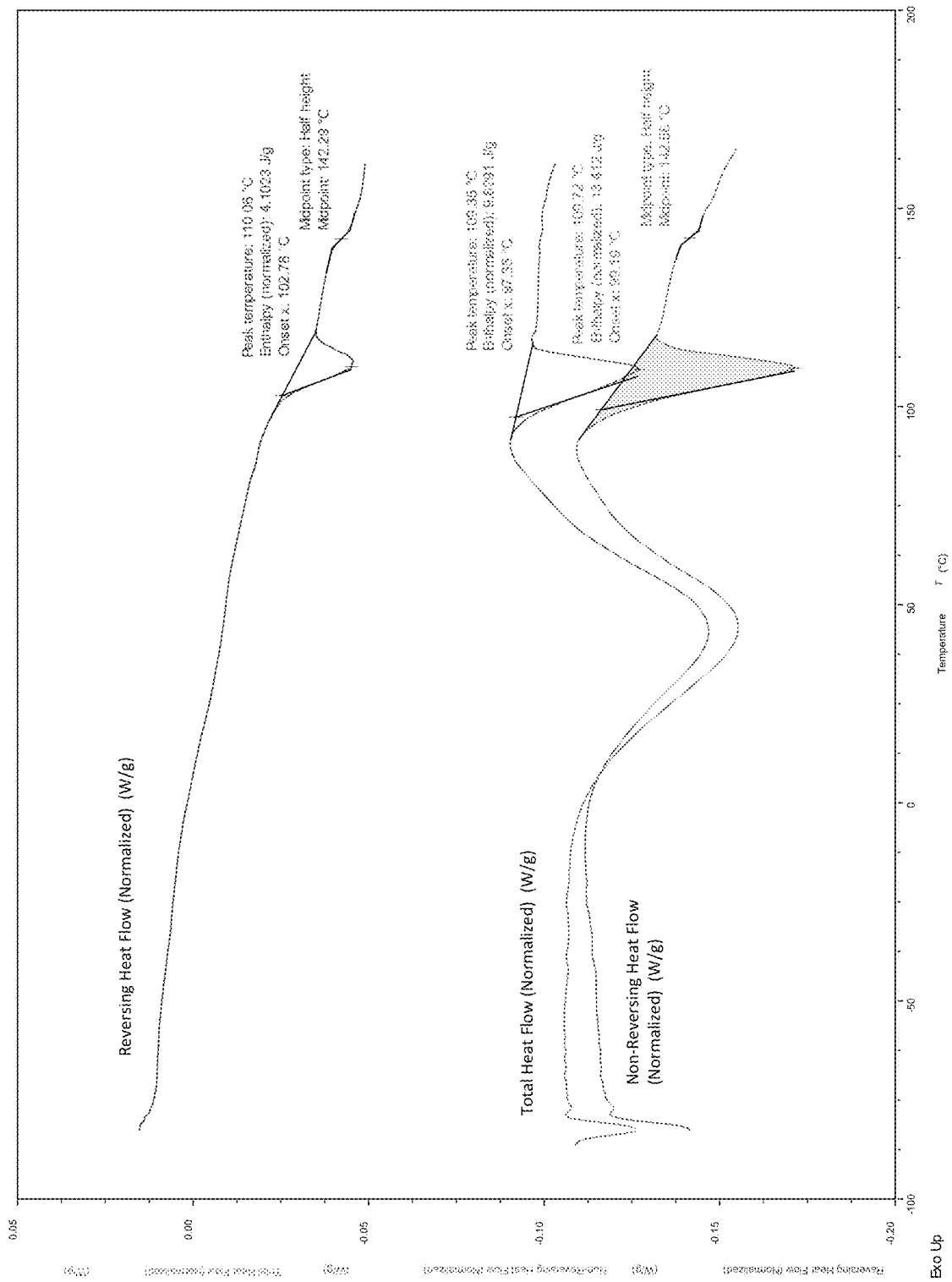
FIG. 32 shows a DSC thermogram for the SDD of Example 14.

The SDD produced was amorphous (FIG. 31) and similar to that produced in Example 12, however, the yield was significantly improved, 52% vs 78%. The DSC thermogram shown in FIG. 32.

Figure 33:
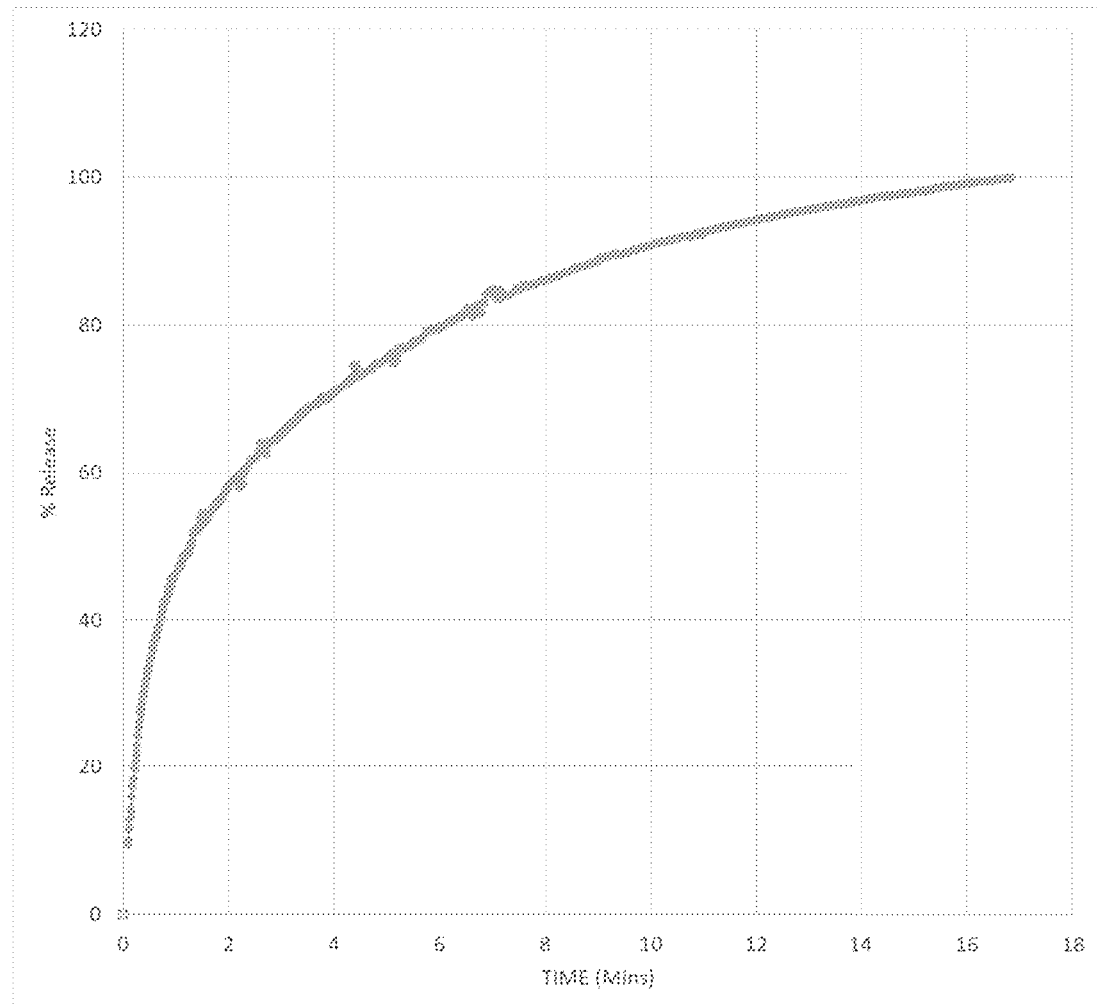
FIG. 33 shows the dissolution profile for the SDD of Example 14.

The dissolution profile, shown in FIG. 33, shows that for the SDD of Example 14 ~80% release has occurred by ~6 minutes, compared with ~4 minutes for the SDD of Example 6, ~10 minutes for the SDD of Example 10, ~6.5 minutes for the SDD of Example 11, ~4.5 minutes for Example 12 and ~10 minutes for the SDD of Example 13.

The inclusion of sorbitol results in an improved yield with no impact on the dissolution rate or stability.

Example 15: Spray Drying of 5-MeO-DMT Benzoate Salt with HPMC Mixtures

Spray drying of 5-MeO-DMT benzoate salt with a mixture of HPMC 2910 and sorbitol in water produced a 50% wt:wt API to excipient SDD. The spray drying parameters were as below:

| SDD Composition | |
| --- | --- |
| Sample Reference | 3815-02-06 |
| Pharmacoat 606 | 35.25% |
| Metolose 60SH50 | 11.75% |
| Sorbitol M | 3% |
| 5-MeO—DMT Benzoate | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 70% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

Figure 34:
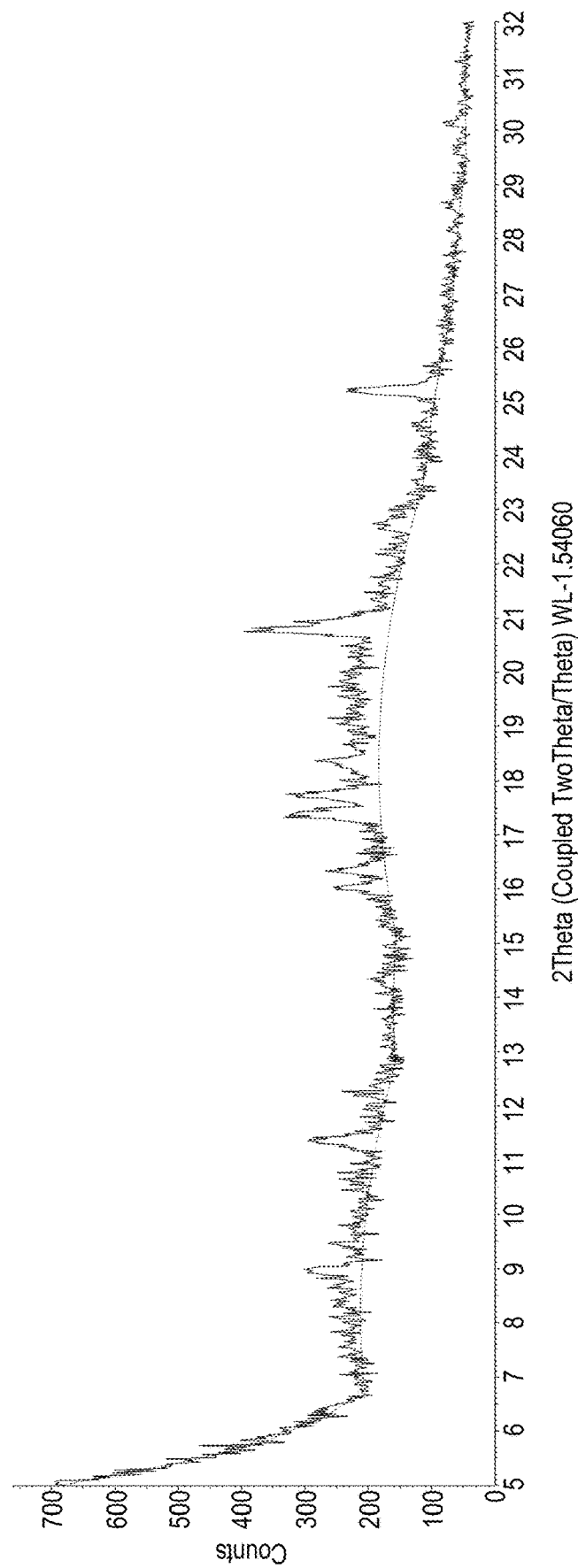
FIG. 34 shows an XRPD of the SDD of Example 15.
Figure 35:
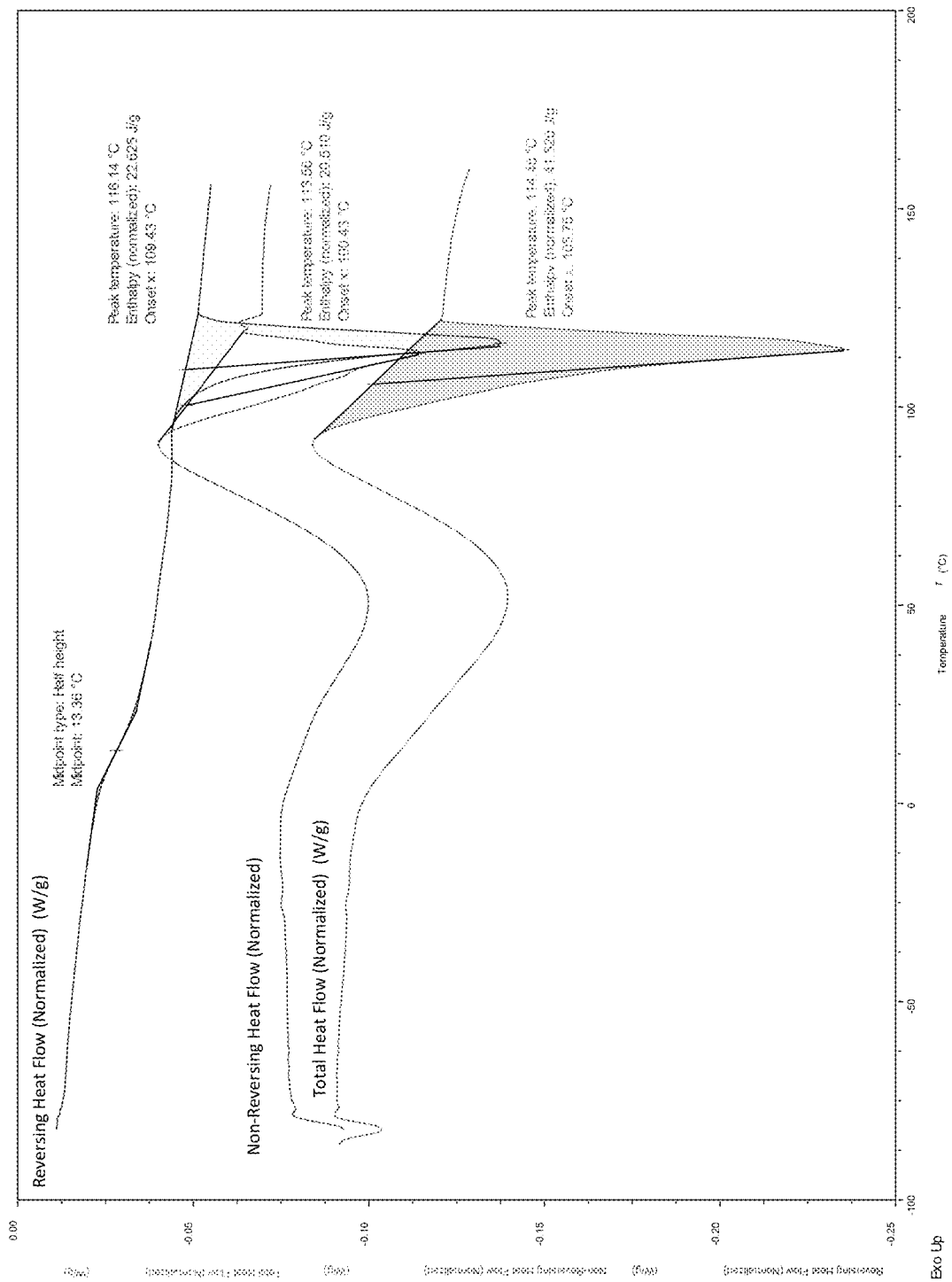
FIG. 35 shows a DSC thermogram for the SDD of Example 15.
Figure 36:
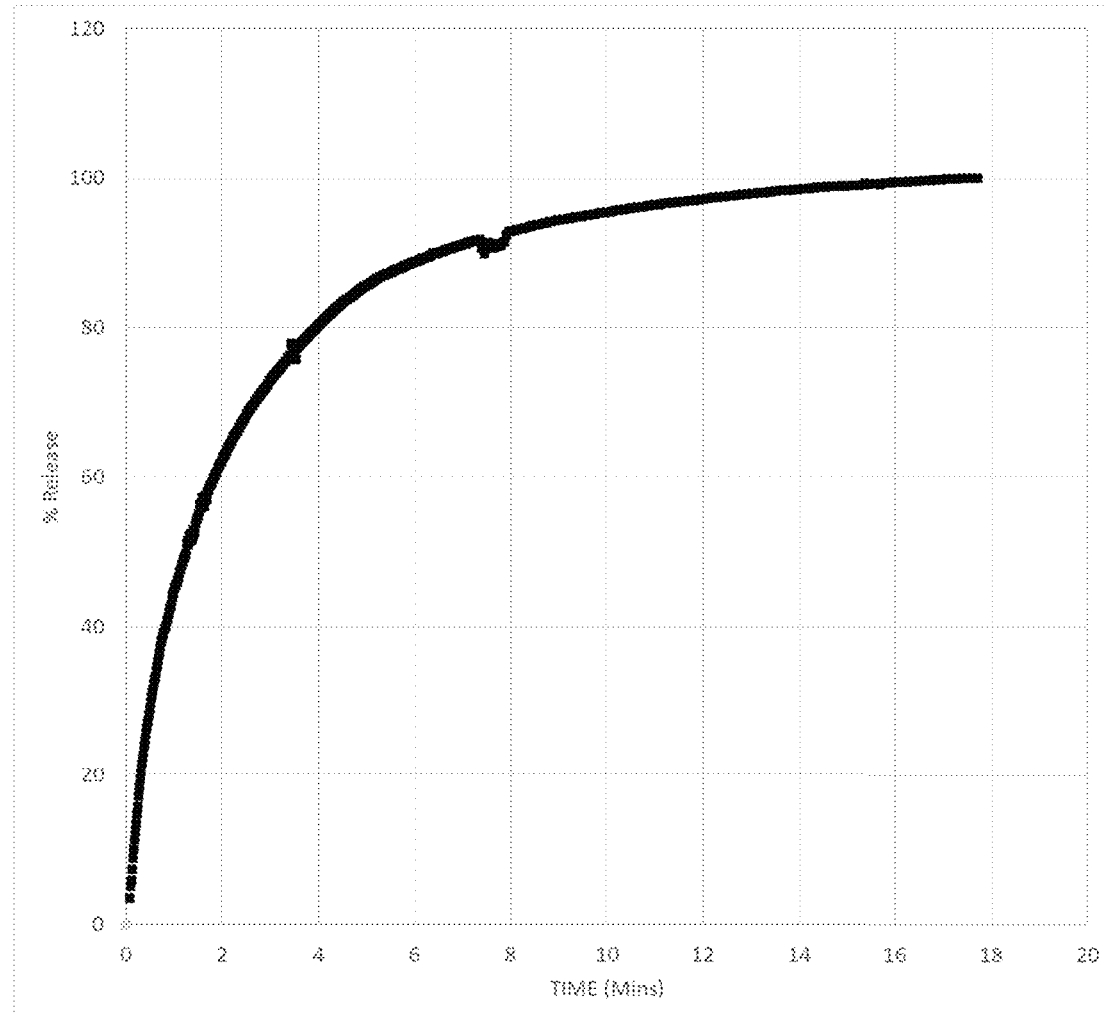
FIG. 36 shows the dissolution profile for the SDD of Example 15.

The SDD produced was partially crystalline (FIG. 34) and the DSC thermogram and dissolution profile of this SDD can be seen in FIGS. 35 and 36. The dissolution profile, shown in FIG. 33, shows that for the SDD of Example 15 ~80% release has occurred by ~4 minutes, compared with ~4 minutes for the SDD of Example 6, ~10 minutes for the SDD of Example 10, ~6.5 minutes for the SDD of Example 11, ~4.5 minutes for Example 12, ~10 minutes for the SDD of Example 13 and ~6 minutes for the SDD of Example 14.

Example 16: Spray Drying of 5-MeO-DMT Hydrobromide Salt with HPMC Mixtures

Spray drying of 5-MeO-DMT hydrobromide salt with a mixture of HPMC 2910 and sorbitol in water produced a 50% wt:wt API to excipient SDD. The spray drying parameters were as below:

| SDD Composition | |
| --- | --- |
| Sample Reference | 3815-37-01 |
| Pharmacoat 606 | 35.25% |
| Metolose 60SH50 | 11.75% |
| Sorbitol M | 3% |
| 5-MeO—DMT hydrobromide | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 81.75% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

The SDD produced was stable and amorphous, unlike that of Example 15, with a dissolution profile similar to that of Example 15. Additionally, the yield for this SDD was higher than that of the SDD of Example 15.

Example 17: Spray Drying of 5-MeO-DMT Hydrochloride Salt with HPMC Mixtures

Spray drying of 5-MeO-DMT hydrochloride salt with a mixture of HPMC 2910 and sorbitol in water produced a 50% wt:wt API to excipient SDD. The spray drying parameters were as below:

| SDD Composition | |
| --- | --- |
| Sample Reference | 3815-37-02 |
| Pharmacoat 606 | 35.25% |
| Metolose 60SH50 | 11.75% |
| Sorbitol M | 3% |
| 5-MeO—DMT hydrochloride | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 78.4%% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

The SDD produced was stable and amorphous, unlike the SDD produced in Example 15. The dissolution profile was similar to the SDD of Example 15.

Example 18: Lyophilisation of HBr Salt with PVP

Lyophilisation of Hydrobromide salt with PVP in water to produce a 50% wt:wt API lyophilized dispersion.

| Feed Solution | |
| --- | --- |
| Sample Reference | |
| PVP | 250 mg |
| 5-MeO—DMT HBr | 250 mg |
| Water (de ionized) | 10 ml |
| Lyophilsation Profile | | | |

| Temp | Ramp | Hold | Vacuum |
| --- | --- | --- | --- |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 37:
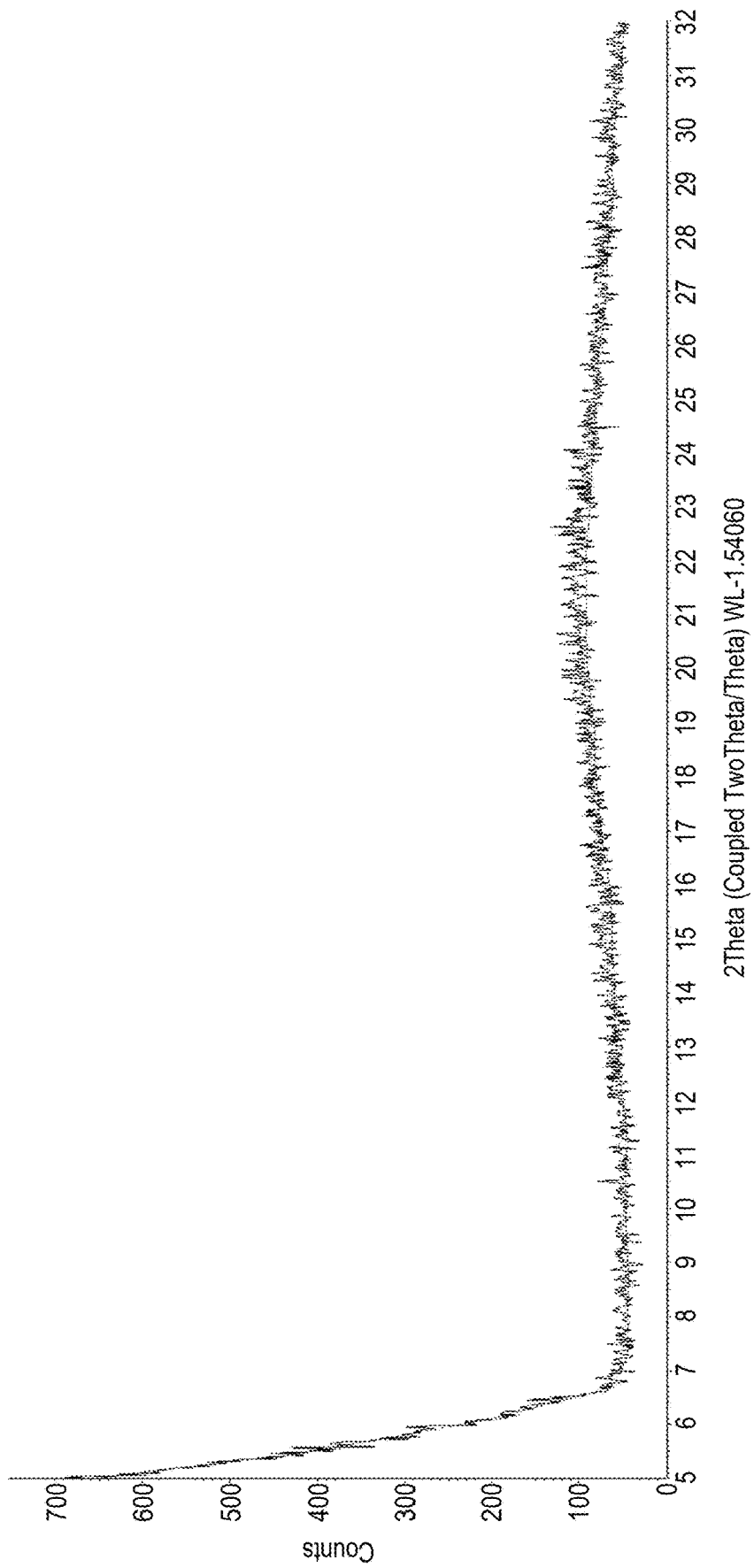
FIG. 37 shows an XRPD of the lyophilized dispersion of Example 18.
Figure 38:
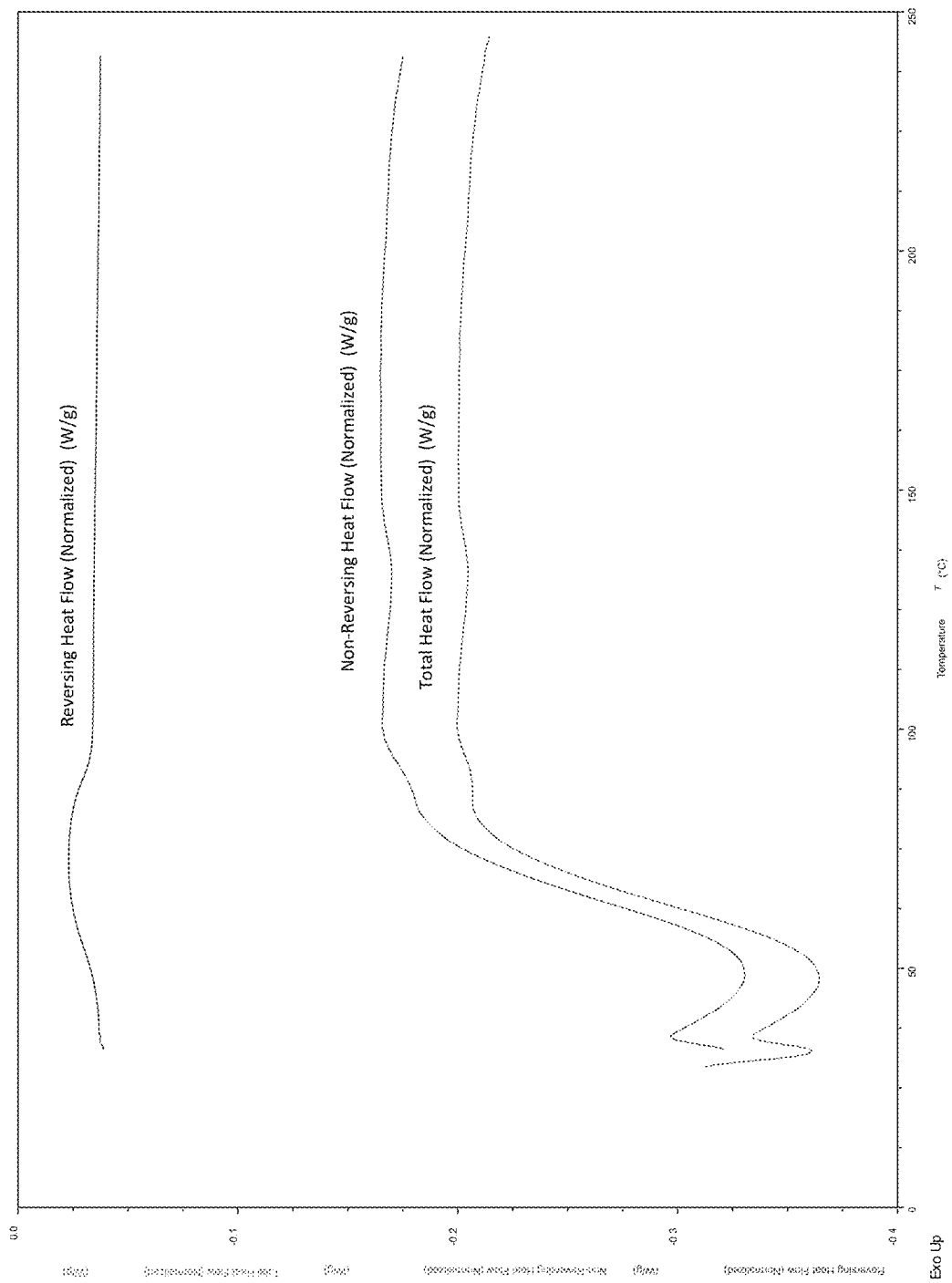
FIG. 38 shows a DSC thermogram for the lyophilized dispersion of Example 18.

Demonstrates that the HBr at 50% loading in PVP will produce an amorphous lyophilized product. FIG. 37 shows an XRPD of the lyophilized dispersion of Example 18. FIG. 38 shows a DSC thermogram for the lyophilized dispersion of Example 18.

Example 19: Lyophilisation of HBr Salt with Lactose Monohydrate

Lyophilisation of Hydrobromide salt with lactose monohydrate in water to produce a 50% wt:wt API lyophilized dispersion.

| Feed Solution | |
| --- | --- |
| Sample Reference | 30130-04-3 |
| Lactose monohydrate | 250 mg |
| 5-MeO—DMT HBr | 250 mg |
| Water (de ionized) | 10 ml |
| Lyophilisation Profile | | | |

| Temp | Ramp | Hold | Vacuum |
| --- | --- | --- | --- |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 39:
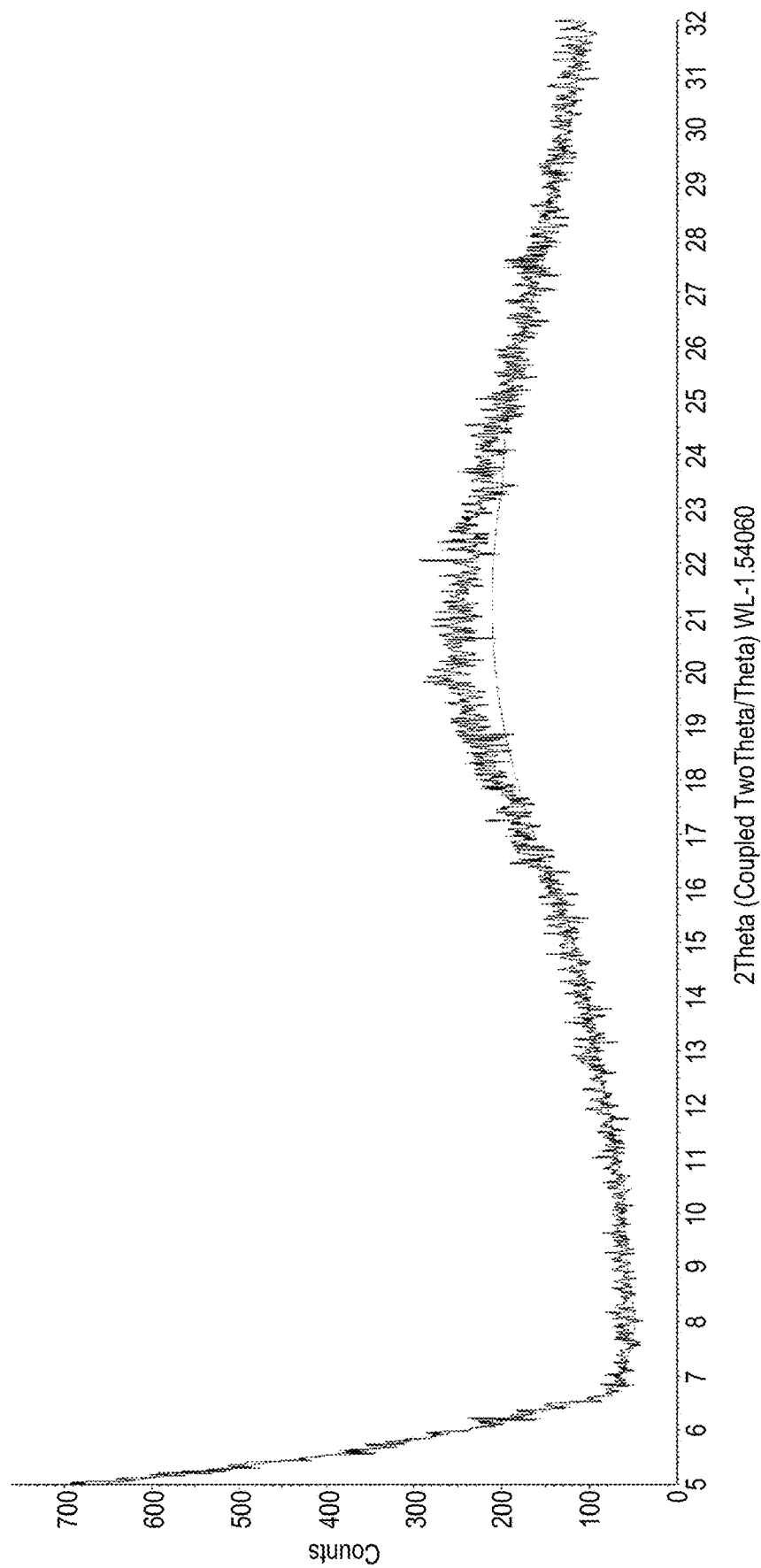
FIG. 39 shows an XRPD of the lyophilized dispersion of Example 19.
Figure 40:
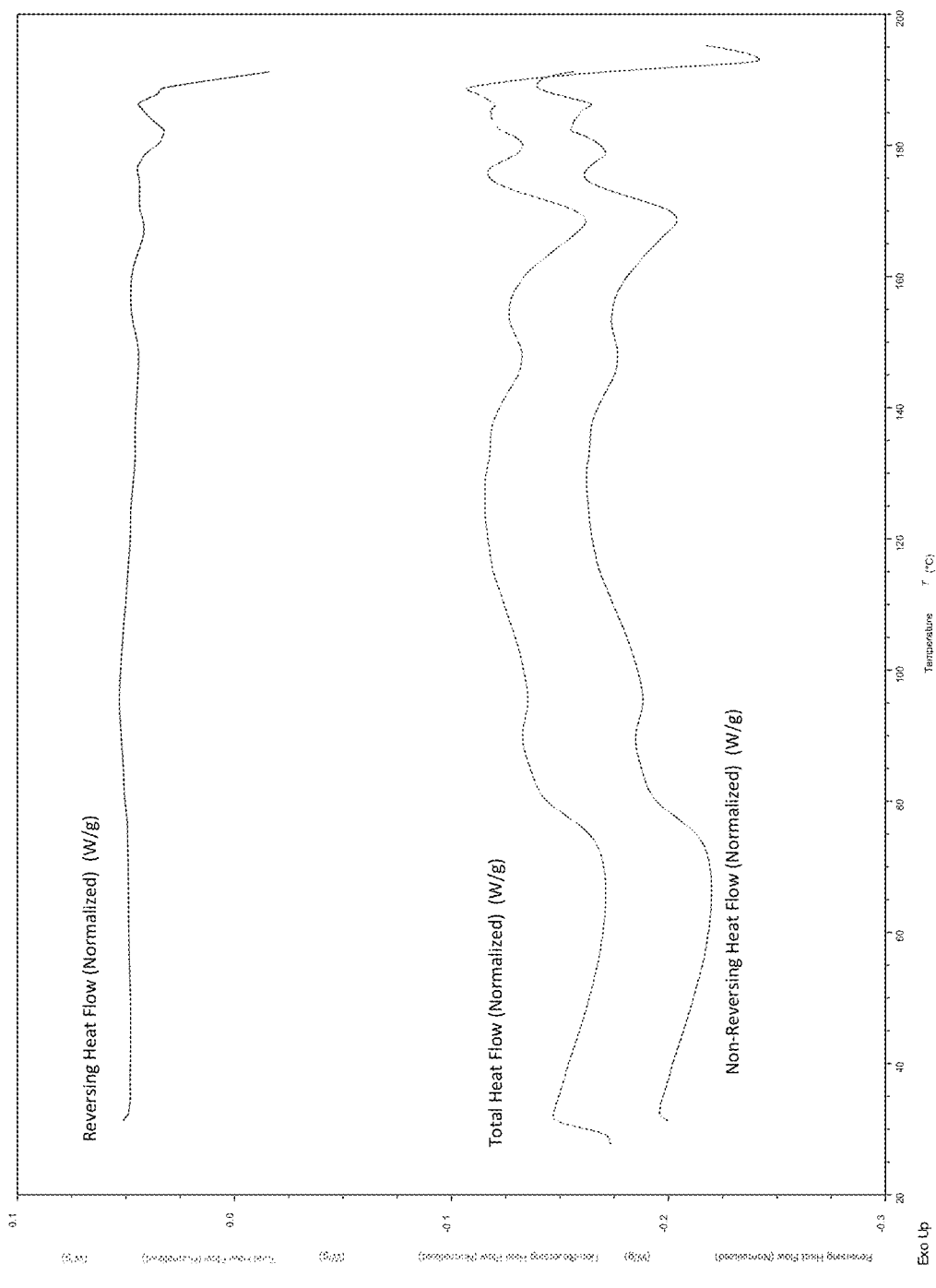
FIG. 40 shows a DSC thermogram for the lyophilized dispersion of Example 19.

Demonstrates that the HBr at 50% loading in lactose monohydrate will produce an amorphous lyophilized product. FIG. 39 shows an XRPD of the lyophilized dispersion of Example 19. FIG. 40 shows a DSC thermogram for the lyophilized dispersion of Example 19.

Example 20: Lyophilisation of HBr Salt with Trehalose

Lyophilisation of Hydrobromide salt with lactose trehalose in water to produce a 50% wt:wt API lyophilized dispersion.

| Feed Solution | |
| --- | --- |
| Sample Reference | 30130-04-4 |
| trehalose | 250 mg |
| 5-MeO—DMT HBr | 250 mg |
| Water (de ionized) | 10 ml |
| Lyophilisation Profile | | | |

| Temp | Ramp | Hold | Vacuum |
| --- | --- | --- | --- |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 41:
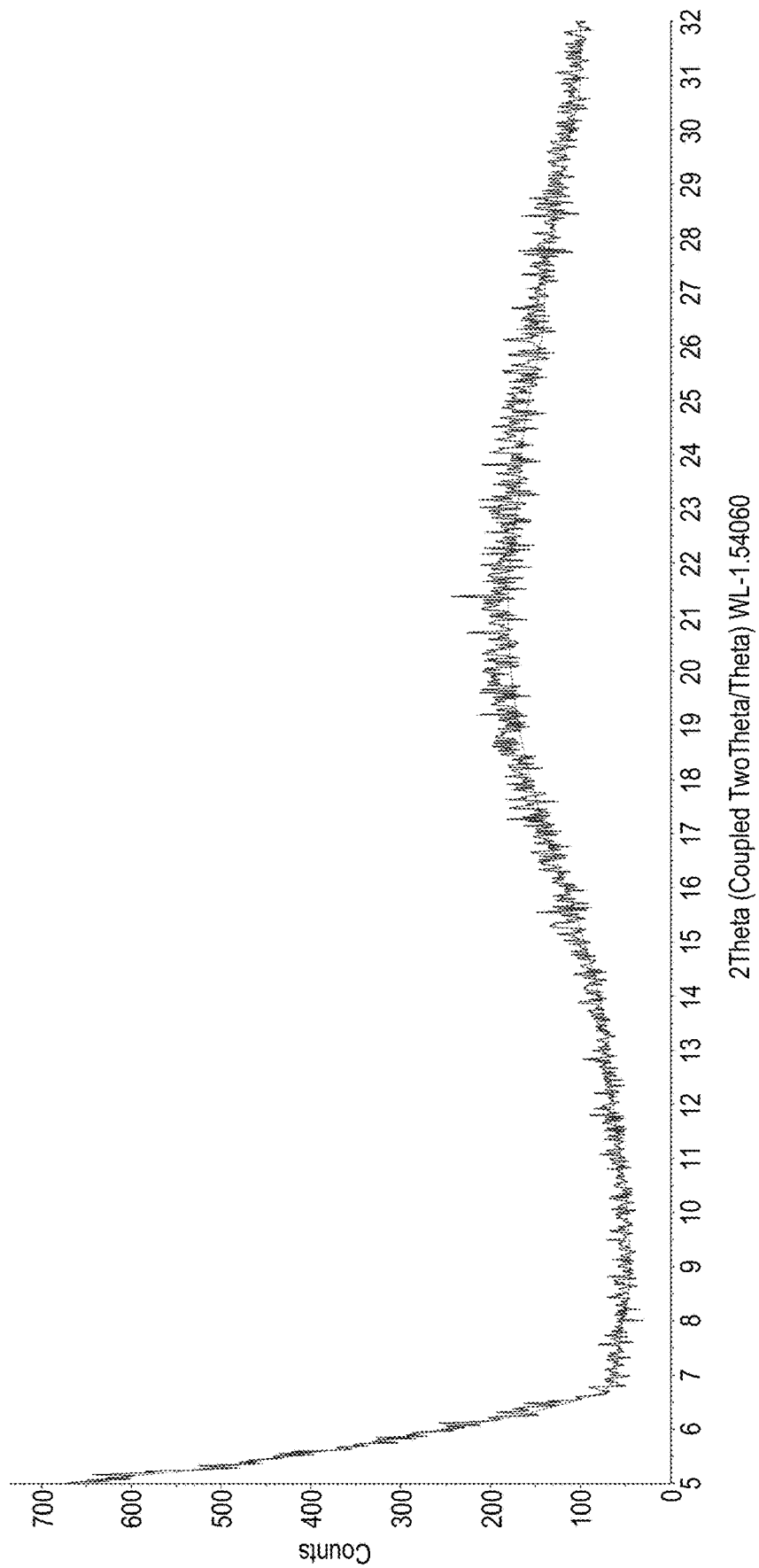
FIG. 41 shows an XRPD of the lyophilized dispersion of Example 20.
Figure 42:
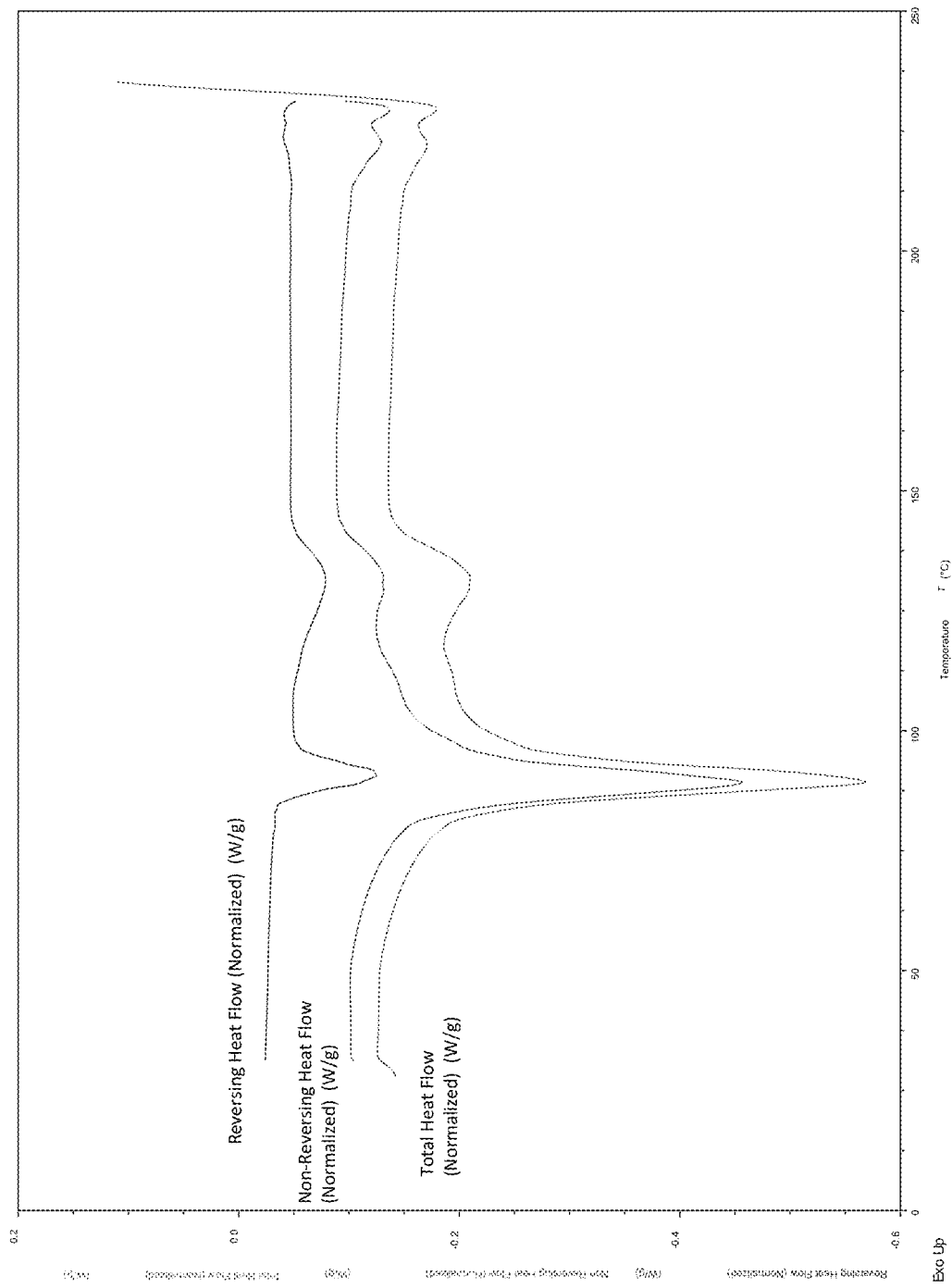
FIG. 42 shows a DSC thermogram for the lyophilized dispersion of Example 20.

Demonstrates that the HBr at 50% loading in trehalose will produce an amorphous lyophilized product. FIG. 41 shows an XRPD of the lyophilized dispersion of Example 20. FIG. 42 shows a DSC thermogram for the lyophilized dispersion of Example 20.

Example 21: Lyophilisation of Oxalate Salt with Trehalose

Lyophilisation of Oxalate salt with lactose trehalose in water to produce a 50% wt:wt API lyophilized dispersion.

| Feed Solution | |
|---|---|
| Sample Reference | 30130-04-5 |
| Trehalose | 250 mg |
| 5-MeO—DMT oxalate | 250 mg |
| Water (de ionized) | 10 ml |

| Lyophilisation Profile | | | |
|---|---|---|---|
| Temp | Ramp | Hold | Vacuum |
| +20° C. | — | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 43:
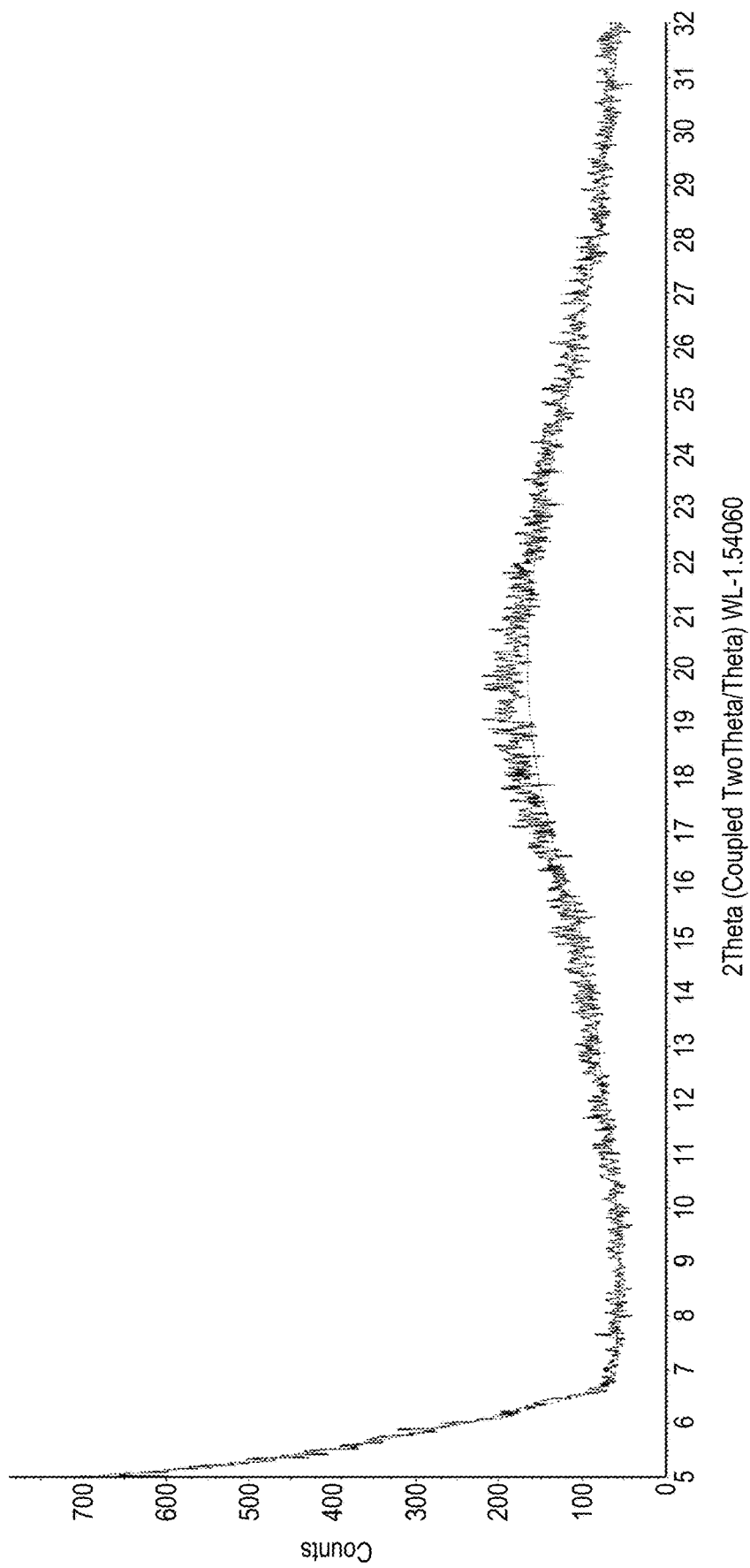
FIG. 43 shows an XRPD of the lyophilized dispersion of Example 21.
Figure 44:
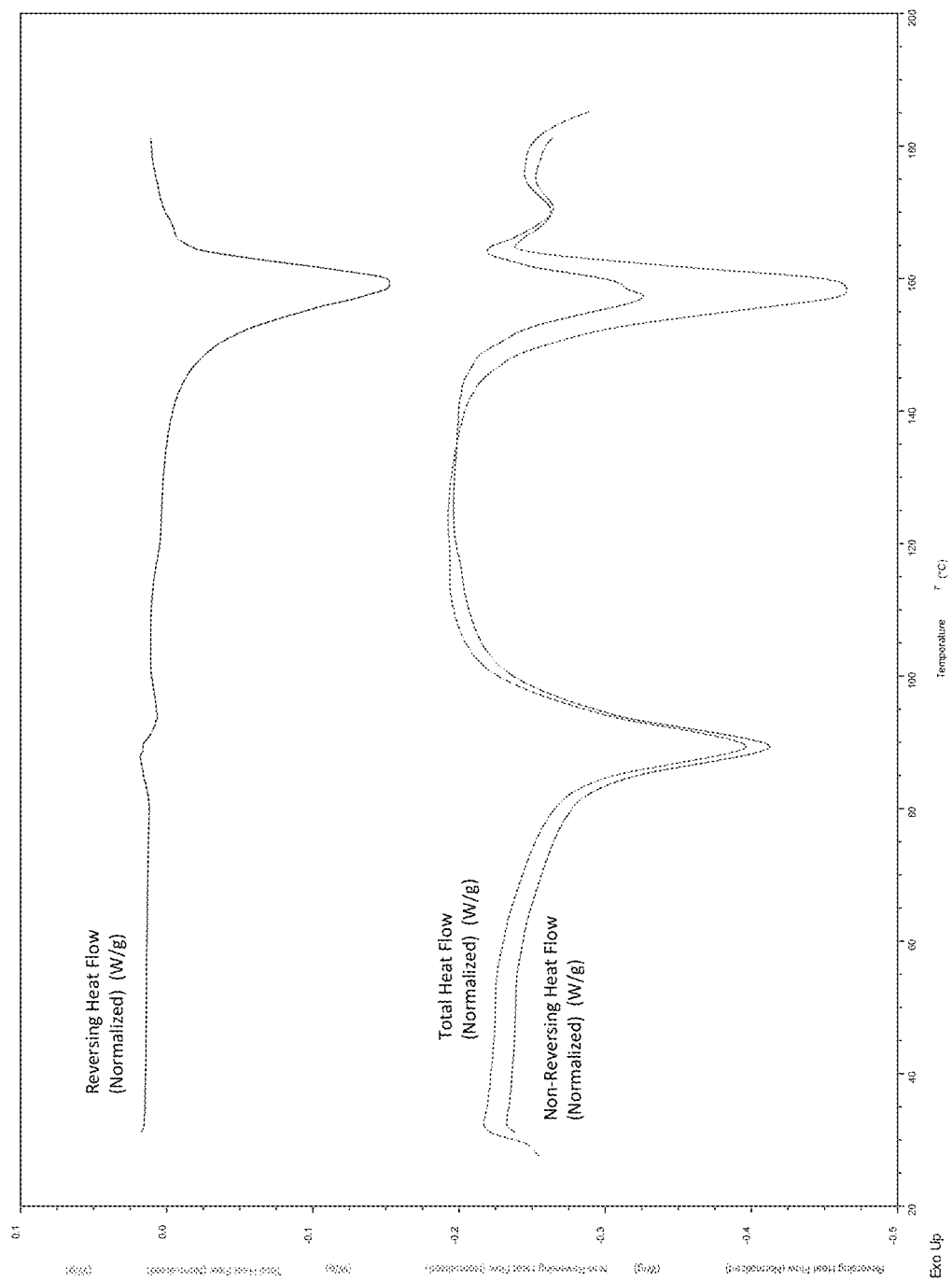
FIG. 44 shows a DSC thermogram for the lyophilized dispersion of Example 21.

Demonstrates that the Oxalate at 50% loading in trehalose will produce an amorphous lyophilized product. FIG. 43 shows an XRPD of the lyophilized dispersion of Example 21. FIG. 44 shows a DSC thermogram for the lyophilized dispersion of Example 21.

Example 22: Lyophilisation of HBr Salt with Mannitol and Trehalose

Lyophilisation of HBr salt with mannitol/trehalose in water to produce a 50% wt:wt API lyophilized dispersion.

| Feed Solution | |
|---|---|
| Sample Reference | 3815-24-02 |
| Mannitol | 150 mg |
| Trehalose | 50 mg |
| 5-MeO—DMT HBr | 200 mg |
| Water (de ionized) | 10 ml |

| Lyophilisation Profile | | | |
|---|---|---|---|
| Temp | Ramp | Hold | Vacuum |
| +20° C. | — | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 45:
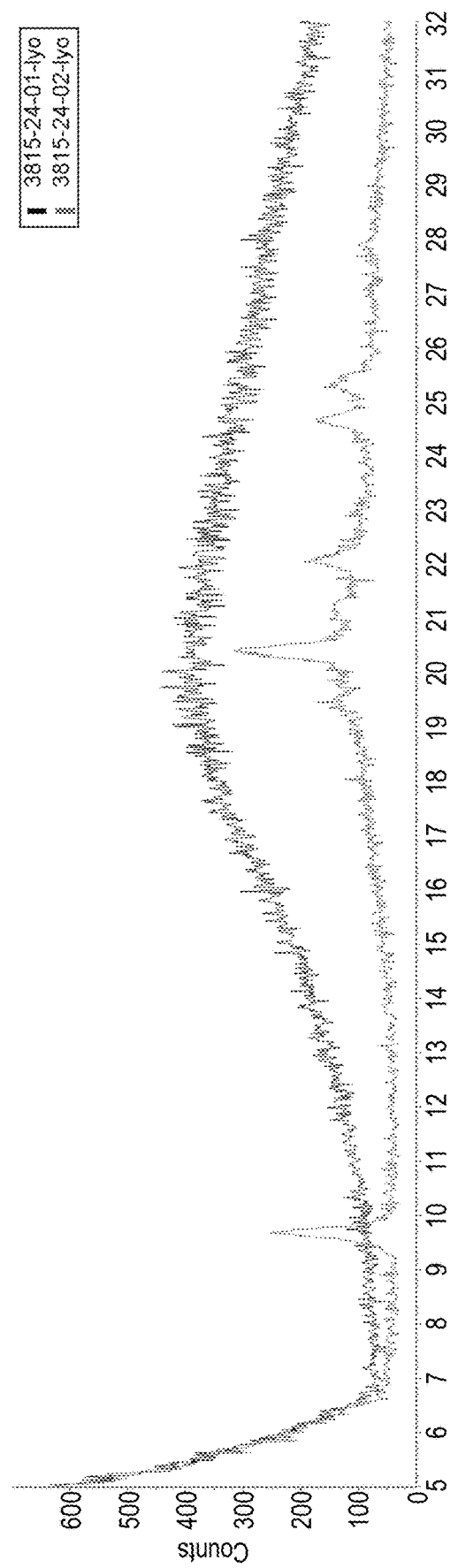
FIG. 45 shows an XRPD of the lyophilized dispersion of Example 22.
Figure 46:
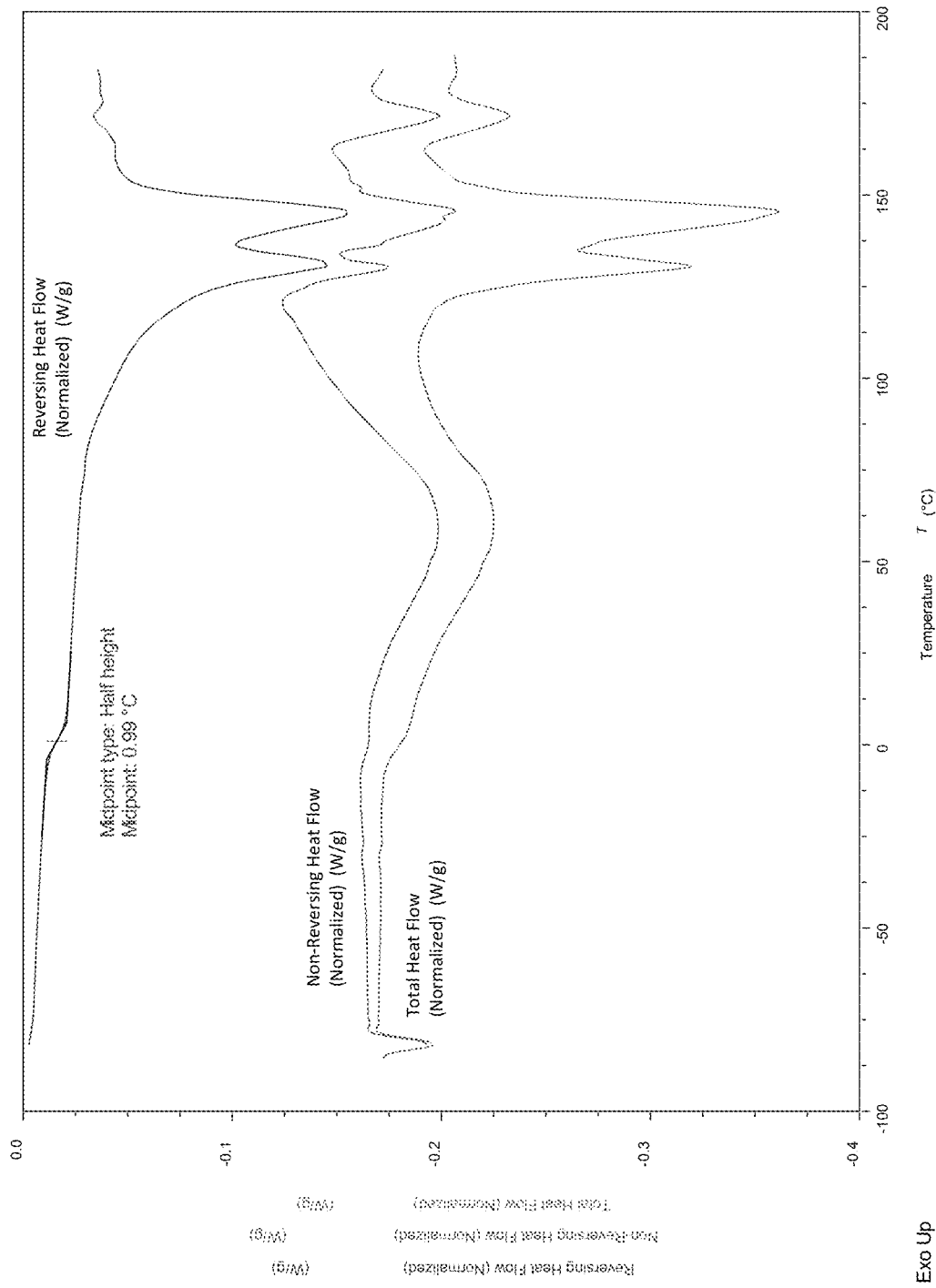
FIG. 46 shows a DSC thermogram for the lyophilized dispersion of Example 22.

Demonstrates that the HBr at 50% loading in mannitol/trehalose does not produce an amorphous lyophilized product. FIG. 45 shows an XRPD of the lyophilized dispersion of Example 22. FIG. 46 shows a DSC thermogram for the lyophilized dispersion of Example 22.

Example 23: Lyophilisation of HBr Salt with Mannitol and Trehalose

Lyophilisation of HBr salt with mannitol/trehalose in water to produce a 50% wt:wt API lyophilized dispersion.

| Feed Solution | |
|---|---|
| Sample Reference | 3815-24-02 |
| Mannitol | 150 mg |
| Trehalose | 50 mg |
| 5MeO DMT HBr | 200 mg |
| Water (de ionized) | 10 ml |

| Lyophilisation Profile | | | |
|---|---|---|---|
| Temp | Ramp | Hold | Vacuum |
| +20° C. | — | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 47:
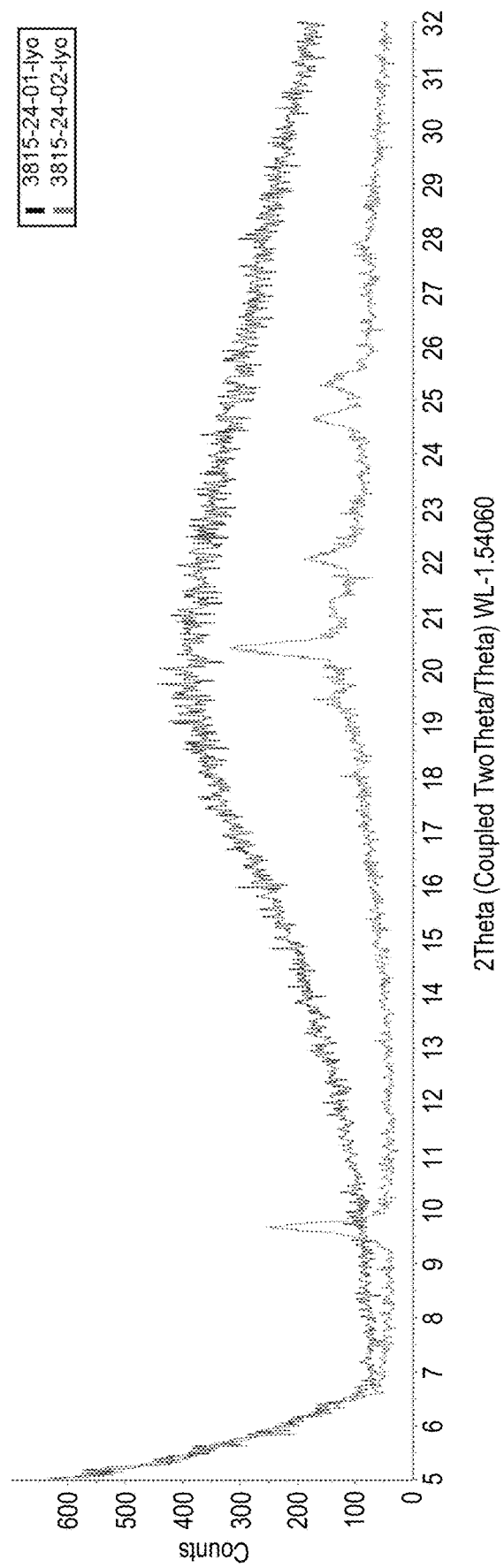
FIG. 47 shows an XRPD of the lyophilized dispersion of Example 23.
Figure 48:
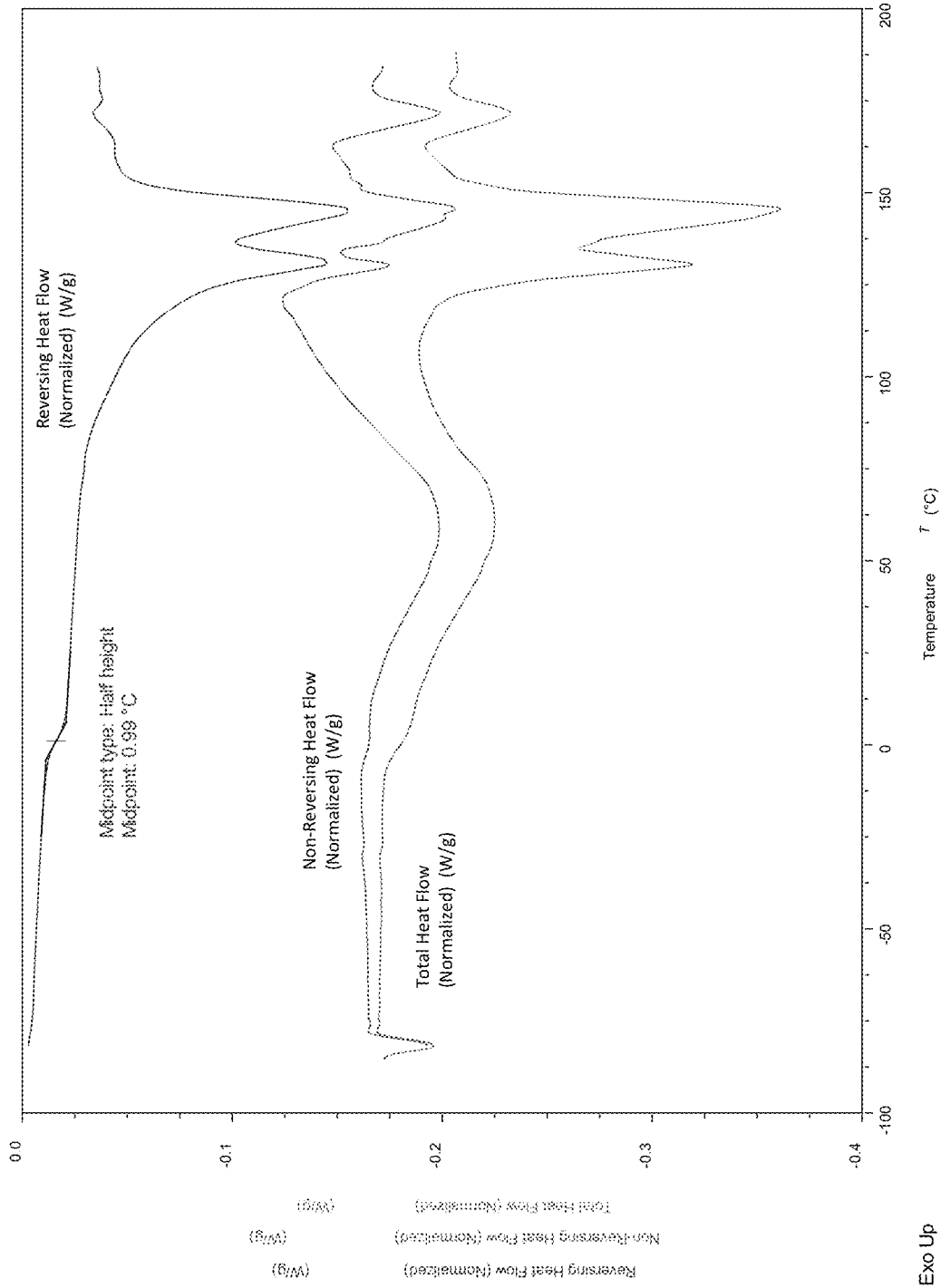
FIG. 48 shows a DSC thermogram for the lyophilized dispersion of Example 23.

Demonstrates that the HBr at 50% loading in mannitol/trehalose does not produce an amorphous lyophilized product. FIG. 47 shows an XRPD of the lyophilized dispersion of Example 23. FIG. 48 shows a DSC thermogram for the lyophilized dispersion of Example 23.

Example 24: Stable Amorphous Formulations of 5-MeO-DMT HBr and HCl

The formulations of 5-MeO-DMT HBr and HCl as described in Examples 16 and 17 were stored for 1 month at (i) 25° C./60% RH or (ii) 2-8° C. The formulations comprised 50% by weight of either 5-MeO-DMT HBr or HCl, a 3:1 ratio of HPMC 606: Metolose 60SH 50 and 3% sorbitol.

Figure 49:
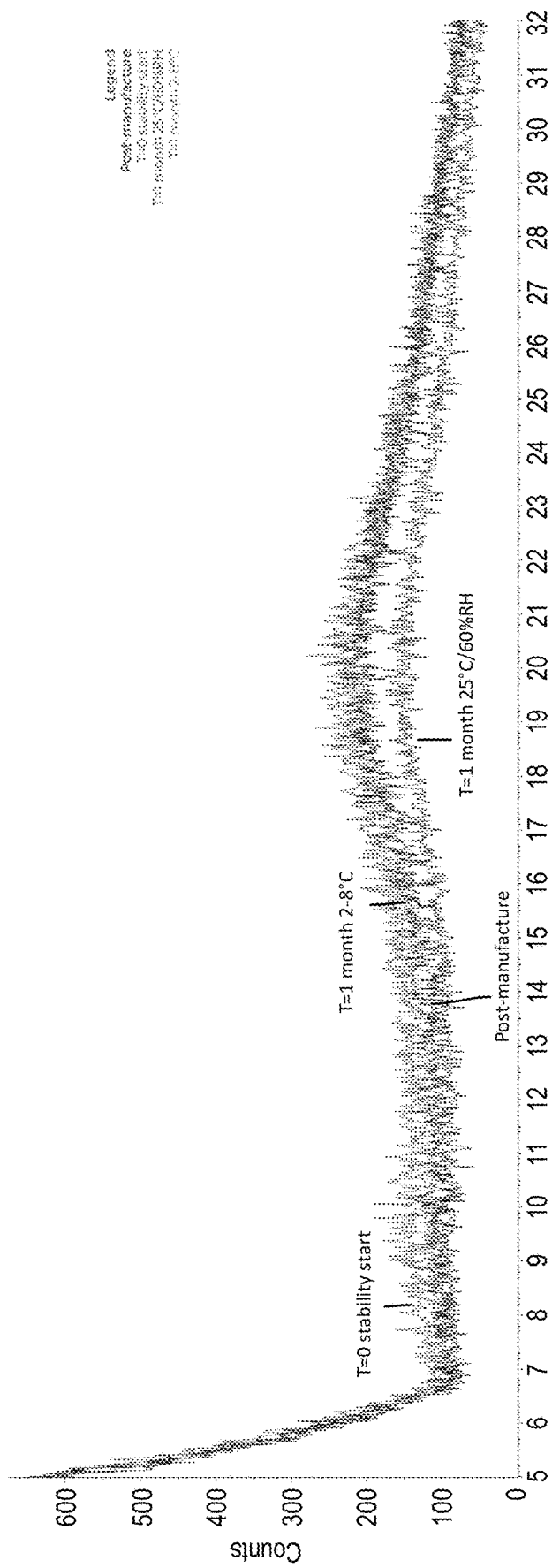
FIG. 49 shows an XRPD diffractogram for the HBr formulation of Example 16 at T=0, T=1 month post storage at 25° C./60% RH and T=1 month post storage at 2-8° C.

A formulation of 5-MeO-DMT HBr stored for 1 month at (i) 25° C./60% RH or (ii) 2-8° C. remained amorphous. FIG. 49 shows an XRPD diffractogram for the HBr formulation of Example 16 at T=0, T=1 month post storage at 25° C./60% RH and T=1 month post storage at 2-8° C. The XRPD showed that the formulation remained amorphous. Analysis by TGA, mDSC, HPLC and scanning electron microscope (SEM) imaging further confirmed that the formulation remained amorphous.

Figure 50:
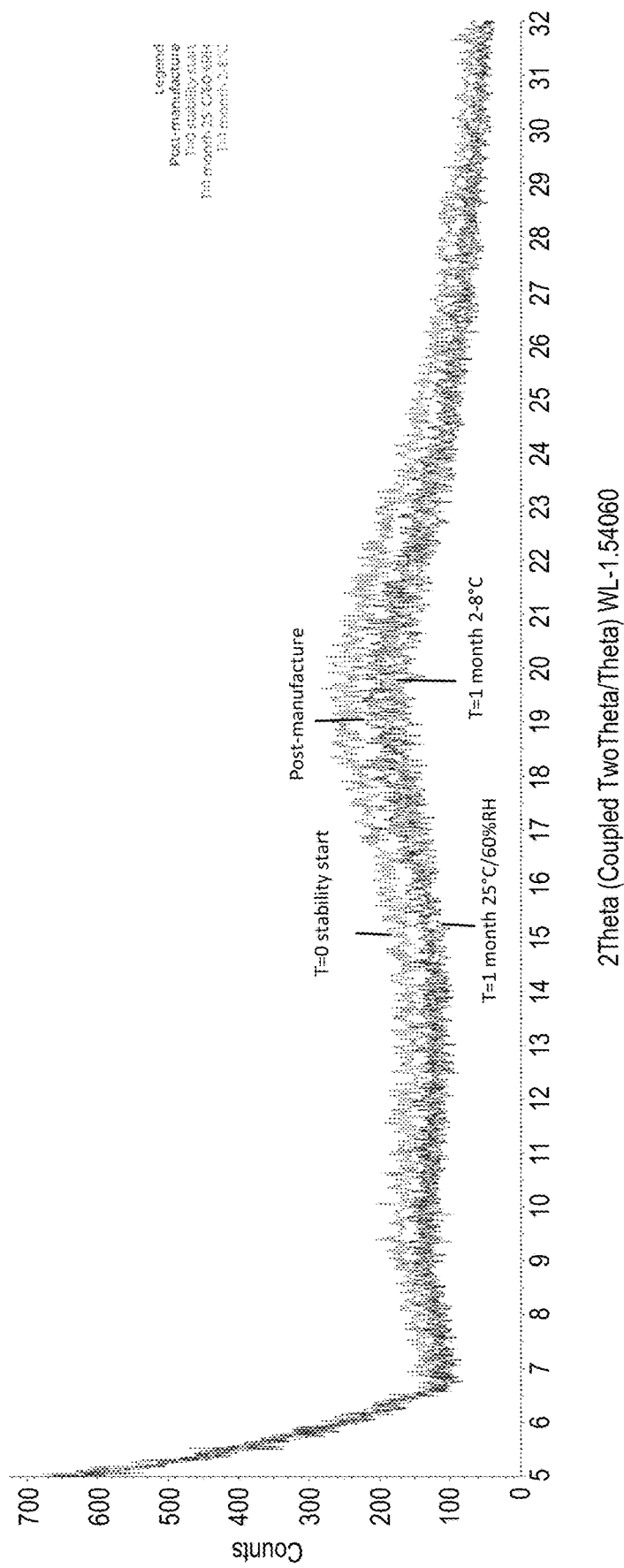
FIG. 50 shows an XRPD diffractogram for the HCl formulation of Example 17 at T=0, T=1 month post storage at 25° C./60% RH and T=1 month post storage at 2-8° C.

A formulation of 5-MeO-DMT HCl stored for 1 month at (i) 25° C./60% RH or (ii) 2-8° C. remained amorphous. FIG. 50 shows an XRPD diffractogram for the HCl formulation of Example 17 at T=0, T=1 month post storage at 25° C./60% RH and T=1 month post storage at 2-8° C. The XRPD showed that the formulation remained amorphous. Analysis by TGA, mDSC, HPLC and scanning electron microscope (SEM) imaging further confirmed that the formulation remained amorphous. There is therefore provided, in an embodiment, a state-stable amorphous formulation of 5-MeO-DMT suitable for storage at, at least, 25° C./60% RH for at least 1, 2, 3, 4, 5, 6, 7, 8, 9, 10, 11 or 12 months, wherein the formulation comprises 5-MeO-DMT HBr or 5-MeO-DMT HCl.

In an embodiment, there is provided a stable amorphous formulation of 5-MeO-DMT. In an embodiment, there is provided a state-stable amorphous formulation of 5-MeO-DMT. In an embodiment, there is provided a stable amorphous formulation of 5-MeO-DMT suitable for storage at, at least, 25° C./60% RH for at least 1, 2, 3, 4, 5, 6, 7, 8, 9, 10, 11, 12 or 24 months. In an embodiment, there is provided an amorphous 5-MeO-DMT HBr formulation. In an embodiment, there is provided a method for producing a stable amorphous formulation of 5-MeO-DMT, as described herein. In an embodiment, there is provided a method for producing a state-stable formulation of 5-MeO-DMT, as described herein.

Example 25: Method for the Determination of Dissolution Rate

The dissolution rate of SDD was determined using a method comprising the use of a UV-fiber optic-based dissolution apparatus (one such suitable device is the Rainbow® Dynamic Dissolution Monitor by Pion Inc) and simulated nasal fluid. The simulated nasal fluid comprises 7.45 g/L NaCl, 1.29 g/L KCl, 0.32 g/L $CaCl_2 \times 2H_2O$ and deionised water.

The dissolution apparatus was set up with a 2 mm probe to measure the dissolution rate. 10 mg of the SDD (5 mg API) was transferred into 5 mL of simulated nasal fluid, heated to a constant temperature of 37° C. and stirred at 150 RPM using a crossed stirrer bar. Measurements were taken at 3 s intervals for 130 intervals followed by 60 measurements taken at 10 s intervals for a total time of 16 minutes and 30 s. Detection of dissolution is by UV absorbance.

Example 26: Method for the Determination of Crystalline Content

A method has been developed for the determination of the crystalline content of psychedelic formulations. Differential scanning calorimetry (DSC) is a thermoanalytical technique in which the difference in the amount of heat required to increase the temperature of a sample and reference is measured as a function of temperature. Both the sample and reference are maintained at nearly the same temperature throughout the experiment. Differential scanning calorimetry can be used to measure a number of characteristic properties of a sample. Using this technique it is possible to observe fusion and crystallization events as well as glass transition temperatures Tg.

The inventors have discovered that a heating rate of 10° C. per minute is not optimised for the determination of crystalline content in psychedelic formulations. The enthalpy obtained from the melt of crystalline 5-MeO-DMT in a formulation was reduced with increased heating rate indicating that a DSC heating rate of 10° C. per minute is not suitable.

Surprisingly, heating rates of above 10° C. per minute is required in order to evaluate the crystalline content of psychedelic formulations. The optimal heating rate has been discovered to be between 100 and 200° C. per minute, between 110 and 190° C. per minute, between 120 and 180° C. per minute, between 130 and 170° C. per minute or between 140 and 160° C. per minute. In an embodiment, the optimal heating rate for the determination of crystalline content of a psychedelic formulation by DSC is 150° C. per minute. In an embodiment, there is provided a method of determining the crystalline content of a 5-MeO-DMT formulation by DSC is 150° C. per minute. In an embodiment, there is provided a method of determining the crystalline content of a spray dried 5-MeO-DMT formulation by DSC is 150° C. per minute.

The invention claimed is:

1. A state-stable amorphous dry powder formulation comprising 5-MeO-DMT HBr and one or more pharmaceutically acceptable carriers or excipients, wherein greater than 70% (w/w) of the 5-MeO-DMT HBr in the formulation is in an amorphous form.

2. The formulation of claim 1, wherein the formulation is a spray dried formulation.

3. The formulation of claim 2, wherein the formulation is a free flowing formulation.

4. The formulation of claim 1, wherein the 5-MeO-DMT HBr is non-hygroscopic.

5. The formulation of claim 3, wherein the formulation comprises below about 5% moisture content by weight of the formulation.

6. The formulation of claim 5, wherein the formulation comprises at least about 10%, 20%, 30%, 40%, 50%, 60%, 70%, 80%, 90%, 95% or 99% by weight 5-MeO-DMT HBr.

7. The formulation of claim 6, wherein at least 95% of the particles of the formulation are larger than 10 microns in size.

8. The formulation of claim 1, wherein no more than 80% of the 5-MeO-DMT is released from the formulation by 4 minutes in water at 37° C.

9. The formulation of claim 1, wherein upon administration to a nasal cavity of a subject the formulation exhibits a residence time, the length of time a substance is present in nasal cavity, for example along the nasal cilia and mucus layer, in the nasal cavity of at least 10, 15, 20, 25 or 30 minutes.

10. The formulation of claim 2, wherein the formulation comprises a cellulose like/based excipient; optionally HPMC, further optionally a high viscosity HPMC.

11. The formulation of claim 10, wherein the formulation comprises a low viscosity HPMC and a high viscosity HPMC.

12. The formulation of claim 11, wherein the ratio of the low viscosity HPMC to high viscosity HPMC is in the ratio of 1:10 to 10:1, optionally 1:4 to 4:1 and further optionally 1:2 to 2:1.

13. The formulation of claim 12, wherein the ratio of the low viscosity HPMC to high viscosity HPMC is in the ratio of 50:50, 45:55, 40:60, 35:65, 30:70 or 25:75.

14. The formulation of claim 10, wherein the high viscosity HPMC has a viscosity greater or equal to about 20, 30, 40, 50 or 60 megaPascals, optionally where the HPMC is a HPMC containing about 7.0-12.0% hydroxypropyl content, about 28.0-30.0% methoxy content, and a viscosity of about 50 mPas.

15. The formulation of claim 10, wherein the low viscosity HPMC has a viscosity less than about 20, 15, 10, 5, 1 megaPascals, optionally where the HPMC is a HPMC containing about 7.0-12.0% hydroxypropyl content, about 28.0-30.0% methoxy content, and a viscosity of about 4.8-7.2 mPas.

16. The formulation of claim 2, wherein the formulation comprises a polyol, optionally the polyol is mannitol, xylitol, sorbitol, maltitol, erythritol, lactitol or isomalt, further optionally the polyol is sorbitol, wherein the formulation comprises about 1-10%, 2-5% or 3% polyol by weight, optionally about 3% sorbitol by weight.

* * * * *

UNITED STATES PATENT AND TRADEMARK OFFICE
CERTIFICATE OF CORRECTION

PATENT NO. : 11,980,605 B1
APPLICATION NO. : 18/229041
DATED : May 14, 2024
INVENTOR(S) : Jason Gray Page 1 of 1

It is certified that error appears in the above-identified patent and that said Letters Patent is hereby corrected as shown below:

In the Specification

Column 2, Line 58, replace "megaPascals" with --milliPascals-seconds (mPa•s)--;
    Line 61, replace "mPas" with --mPa•s--;
    Line 62, replace "megaPascals" with --milliPascal-seconds (mPa•s)--;
    Line 65, replace "mPas" with --mPa•s--;

Column 3, Line 32, replace "mPas" with --mPa•s--;
    Line 35, replace "mPas" with --mPa•s--;

Column 4, Line 14, replace "megaPascals" with --milliPascal-seconds (mPa•s)--;
    Line 17, replace "megaPascals" with --milliPascal-seconds (mPa•s)--;

Column 7, Line 23, replace "mPas" with --mPa•s--;
    Line 32, replace "mPas" with --mPa•s--;
    Line 35, replace "mPas" with --mPa•s--;
    Line 40, replace "mPas" with --mPa•s--;

In the Claims

Column 32, Claim 14, Line 47, replace "megaPascals" with --milliPascal-seconds (mPa•s)--;
    Claim 14, Line 50, replace "mPas" with --mPa•s--;
    Claim 15, Line 53, replace "megaPascals" with --milliPascal-seconds (mPa•s)--;
    Claim 15, Line 56, replace "mPas" with --mPa•s--.

Signed and Sealed this
Twenty-eighth Day of January, 2025

Coke Morgan Stewart
*Acting Director of the United States Patent and Trademark Office*